United States Patent [19]

Hashimoto et al.

[11] Patent Number: 4,968,341

[45] Date of Patent: Nov. 6, 1990

[54] SUBSTITUTED ARYLOXYUREAS, PROCESSES FOR PRODUCTION THEREOF AND USES THEREOF

[75] Inventors: Isao Hashimoto, Iwakuni; Tatsuyodihi Ishida, Ohtake; Kazutaka Tsuru, Iwakuni; Yuji Yamada, Shizuoka; Takeshige Miyazawa, Shizuoka; Yasuo Nakamura, Shizuoka; Susumu Katou, Shizuoka; Katsuya Takahashi, Otake, all of Japan

[73] Assignees: Kumiai Chemical Industry Co.; Mitsui Petrochemical Industries, Ltd., both of Tokyo, Japan

[21] Appl. No.: 232,634

[22] Filed: Aug. 16, 1988

Related U.S. Application Data

[63] Continuation of Ser. No. 800,031, Nov. 20, 1985, abandoned, and a continuation of Ser. No. 159,966, Feb. 17, 1988, abandoned, and a continuation of Ser. No. 151,516, Feb. 17, 1988, abandoned.

[30] Foreign Application Priority Data

| | | | |
|---|---|---|---|
| Nov. 26, 1984 | [JP] | Japan | 248040 |
| May 26, 1986 | [JP] | Japan | 119293 |
| May 26, 1986 | [JP] | Japan | 119294 |

[51] Int. Cl.[5] .................... A01N 43/36; A01N 43/40; A01N 43/44; A01N 43/46; A01N 47/38; C07D 211/06; C07D 233/02

[52] U.S. Cl. .................................... 71/88; 71/94; 71/95; 540/450; 540/477; 540/583; 540/597; 540/601; 540/607; 544/63; 544/88; 544/169; 544/130; 544/218; 544/219; 544/238; 544/239; 544/319; 544/408; 546/193; 546/266; 546/280; 546/291; 546/323; 548/215; 548/452; 548/515; 548/538; 548/953; 548/966; 560/19; 560/30; 564/47

[58] Field of Search .............. 71/94, 95, 88; 546/226, 546/323; 548/537, 953, 966, 538; 540/607, 450

[56] References Cited

U.S. PATENT DOCUMENTS 3,332,975 7/1967 Bauer et al. .................... 424/471 X

FOREIGN PATENT DOCUMENTS 179806 7/1988 Japan .

OTHER PUBLICATIONS

Bauer, et al., J. Med. Chem., 8, (1965), pp. 886–887.

*Primary Examiner*—Mukund J. Shah
*Assistant Examiner*—Philip Datlow
*Attorney, Agent, or Firm*—Oblon, Spivak, McClelland, Maier & Neustadt

[57] ABSTRACT

Novel substituted aryloxyureas, processes for their production, and herbicides comprising them as active ingredients are provided.

The substituted aryloxyureas exhibit an excellent herbicidal efficacy against weeds when applied, for example, to the weeds in a wide range of period from a preemergence stage to a growth stage.

The substituted aryloxyureas of the invention have the excellent advantage of maintaining high safety on crops or crop plants in spite of their herbicidal efficacy.

7 Claims, No Drawings

SUBSTITUTED ARYLOXYUREAS, PROCESSES FOR PRODUCTION THEREOF AND USES THEREOF

This is a continuation of Ser. No. 06/800,031, filed Nov. 20, 1985, now abandoned; Ser. No. 07/159,966, filed Feb. 17, 1988, now abandoned; and Ser. No. 07/151,516, filed Feb. 17, 1988, now abandoned.

TECHNOLOGICAL FIELD

This invention relates to a novel substituted aryloxyurea, processes for its production, and to a herbicide comprising it as an active ingredient.

BACKGROUND TECHNOLOGY

Many herbicides have been used to secure quantities of crops harvested. Urea-series compounds, for example DCMU widely used as a herbicide for upland farms, have the defect that they cannot be used in paddies because of their strong phytotoxicity.

U.S. Pat. No. 3,332,975 discloses that m-chlorophenoxyureas which differ in chemical structure from the compounds of this invention can be used as medicines. As will be stated hereinafter, however, these compounds do not exhibit a herbicidal efficacy, and even if they do, their herbicidal efficacy is very weak.

Japanese Patent Publication No. 5254/1966 describes substituted ureas or thioureas represented by the following formula:

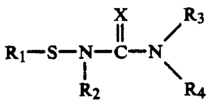

wherein $R_1$ represents a phenyl or halophenyl group, or a group of the formula

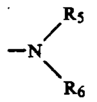

in which $R_5$ and $R_6$ are the same alkyl or aralkyl groups, or may form a piperidino or morpholino group together with the nitrogen atom to which they are bonded; $R_2$ represents a lower aliphatic hydrocarbon group, a phenyl group, or a phenyl group substituted by at least one of halogen, alkylmercapto, nitro and alkoxy; $R_3$ and $R_4$ are the same alkyl or aralkyl groups, or may form a piperidino or morpholino group together with the nitrogen atom to which they are bonded; and X is oxygen or sulfur.

It also describes that these compounds are herbicides, although it discloses no biological data.

Japanese Patent Publication No. 6999/1971 discloses that compounds of the following formula

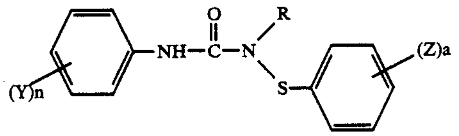

wherein R is a $C_1$–$C_4$ alkyl group; Y is F, Cl, Br or I, a $C_1$–$C_4$ alkyl group, or a $C_1$–$C_4$ alkoxy group; n is 0, or an integer of 1 to 3 when Y is the halogen atom, or 1 when Y is the alkyl or alkoxy group; Z is F, Cl, Br or I or a $C_1$–$C_4$ alkyl group; and a is 0, or an integer of 1 to 5 when Z is the halogen atom, or 1 when z is the alkyl group, are a herbicide to be applied to plants or their growing sites.

It is an object of this invention to provide novel substituted aryloxyureas.

Another object of this invention is to provide novel substituted aryloxyureas which exhibit an excellent herbicidal efficacy.

Still another object of this invention is to provide novel substituted aryloxyureas which exhibit an excellent herbicidal efficacy against weeds when applied to the weeds over a wide range of periods from a pre-emergence stage to a growing stage.

Yet another object of this invention is to provide novel substituted aryloxyureas which exhibit a herbicidal efficacy and yet are highly safe to crops or crop plants.

A further object of this invention is to produce the compounds of this invention having excellent herbicidal activity with industrial advantage.

Other objects and advantages of this invention will become apparent from the following description.

DISCLOSURE OF THE INVENTION

According to this invention, the above objects and advantages of this invention are achieved by substituted aryloxyureas represented by the following formulas of three embodiments of the invention.

Embodiment A:

(I)

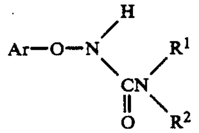

wherein Ar represents a group selected from the class consisting of aryl groups of the following formulaes:

(a)

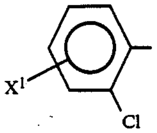

in which $X^1$ represents a hydrogen atom, a lower alkyl group or a lower alkoxy group, (b)

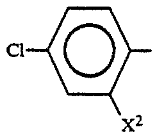

in which $X^2$ represents a hydrogen or halogen atom, (c)

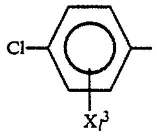

in which $X^3$ represents a halogen atom and l is an integer of 2 or 3, (d)

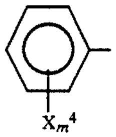

in which $X^4$ represents a fluorine, bromine or iodine atom, and m is an integer of 1, 2 or 3, (e)

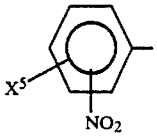

in which $X^5$ represents a hydrogen atom, a halogen atom, a lower alkyl group, a lower alkoxy group or trifluoromethyl group, (f)

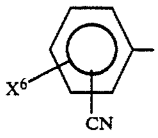

in which $X^6$ represents a hydrogen or halogen atom, (g)

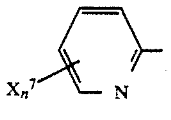

in which $X^7$ represents a hydrogen atom, a halogen atom, a cyano group, a lower alkoxy group or a trifluoromethyl group, and n is an integer of 1 or 2, (h)

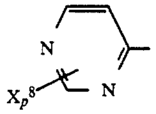

in which $X^8$ represents a hydrogen atom, a chlorine atom or a lower alkylthio group, and p is an integer of 1 or 2, (i)

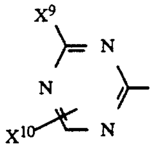

in which $X^9$ and $X^{10}$ are identical or different and each represents a chlorine atom, a lower alkoxy group or a lower alkylthio group, and (j)

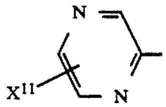

in which $X^{11}$ represents a hydrogen or chlorine atom;

$R^1$ represents a $C_1$–$C_6$ alkyl group, a lower alkenyl group, a lower alkynyl group or a $C_3$–$C_7$ cycloalkyl group; $R^2$ represents a hydrogen atom or a $C_1$–$C_6$ alkyl group; and $R^1$ and $R^2$, together with the nitrogen atom to which they are bonded, may form a 4- to 8-membered heterocyclic ring which may contain an oxygen atom as a ring member or may be substituted by a lower alkyl group or a lower alkylene group, and acid addition salts thereof.

In formula (I), Ar is a group of any of the formulas (a) to (j) above. The groups of formula (a) to (j) are substituted phenyl [(a) to (f)], pyridyl (g), pyrimidinyl (h), triazinyl (i) and pyrazinyl (j) groups, and are common in that they are aromatic groups.

In the group of formula (a), $X^1$ is a hydrogen atom, a lower alkyl group or a lower alkoxy group.

The lower alkyl group is preferably a linear or branched alkyl group having 1 to 4 carbon atoms, such as methyl, ethyl, n-propyl, iso-propyl, n-butyl, sec-butyl, iso-butyl or t-butyl.

The lower alkoxy group is preferably one having a linear or branched alkyl moiety with 1 to 4 carbon atoms. Examples are methoxy, ethoxy, n-propoxy, iso-propoxy, n-butoxyl, sec-butoxy, iso-butoxy, and t-butoxy.

Preferred examples of the group of formula (a) are 2-chlorophenyl, 2-chloro-5-methylphenyl, 2-chloro-3-methylphenyl, 2-chloro-4-methylphenyl, 2-chloro-6-methylphenyl, 2-chloro-5-methoxyphenyl, 2-chloro-6-methoxy-phenyl, 2-chloro-4-methoxyphenyl and 2-chloro-3-methoxy-phenyl.

In formula (b), $X^2$ represents a hydrogen or halogen atom.

Preferred examples of the halogen atom are fluorine, chlorine, bromine and iodine.

Preferred examples of the group (b) are 4-chlorophenyl, 2,4-dichlorophenyl, 2-bromo-4-chlorophenyl and 4-chloro-2-fluorophenyl.

In formula (c), $X^3$ is a halogen atom, and l is an integer of 2 or 3.

Fluorine, chlorine, bromine and iodine may be cited as preferred examples of the halogen atom.

Preferred examples of the group of formula (c) are 2,4,5-trichlorophenyl, 3,4,5-trichlorophenyl, 2,3,4-trichlorophenyl, 2,4,6-trichlorophenyl and 2,3,4,5-tetrachlorophenyl.

In formula (d), $X^4$ represents a fluorine, bromine or iodine atom, and m is an integer of 1, 2 or 3.

Preferred examples of the group of formula (d) include 2-fluorophenyl, 3-fluorophenyl, 4-fluorophenyl, 2,5-difluorophenyl, 3,5-difluorophenyl, 2,4-difluorophenyl, 4-bromophenyl, 3-bromophenyl, 2-bromophenyl, 2-iodophenyl and 4-iodophenyl.

In formula (e), $X^5$ represents a hydrogen atom, a halogen atom, a lower alkyl group, a lower alkoxy group, or a trifluoromethyl group.

Examples of the halogen atom may be the same as those given above with regard to $X^3$.

Specific examples of the lower alkyl and lower alkoxy groups are the same as those given above with regard to $X^1$.

Examples of formula (e) include 2-nitrophenyl, 3-nitrophenyl, 4-nitrophenyl, 4-chloro-2-nitrophenyl, 5-chloro-2-nitrophenyl, 5-chloro-2-nitrophenyl, 3-chloro-5-nitrophenyl, 5-methyl-2-nitrophenyl, 4-methyl-2-nitrophenyl, 3-chloro-4-nitrophenyl, 2-chloro-4-nitrophenyl, 2-methyl-6-nitrophenyl, 3-methyl-4-nitrophenyl, 2-methyl-4-nitrophenyl, 2-nitro-4-trifluoromethylphenyl, 3-nitro-5-trifluoromethylphenyl and 5-nitro-2-trifluoromethyl.

In formula (e), $X^6$ is a hydrogen or halogen atom.

Preferred specific examples of the halogen atom may be the same as those given with regard to $X^3$.

Preferred examples of the group of formula (e) are 2-cyanophenyl, 3-cyanophenyl, 4-cyanophenyl, 3-chloro-2-cyanophenyl, 4-chloro-2-cyanophenyl, 5-chloro-2-cyanophenyl, 6-chloro-2-cyanophenyl, 2-chloro-3-cyanophenyl, 4-chloro-3-cyanophenyl, 3-chloro-5-cyanophenyl, 2-chloro-5-cyanophenyl, 3-chloro-4-cyanophenyl and 2-chloro-4-cyanophenyl.

In formula (g), $X^7$ is a hydrogen atom, a halogen atom, a cyano group, a lower alkoxy group or a trifluoromethyl group.

Preferred specific examples of the halogen atom and the lower alkoxy groups may be the same as those given with regard to $X^5$.

Examples of the group of formula (g) are 6-chloro-2-pyridyl, 5-chloro-2-pyridyl, 4-chloro-2-pyridyl, 3-chloro-2-pyridyl, 3,5-dichloro-2-pyridyl, 6-methoxy-2-pyridyl, 5-methoxy-2-pyridyl, 4-methoxy-2-pyridyl, 3-methoxy-2-pyridyl, 4-trifluoromethyl-2-pyridyl, 5-trifluoromethyl-2-pyridyl, 6-trifluoromethyl-2-pyridyl and 3-chloro-5-trifluoromethyl-2-pyridyl. Of these, 6-chloro-2-pyridyl and 6-trifluoromethyl-2-pyridyl are preferred.

In formula (h), $X^8$ is a hydrogen atom, a chlorine atom, or a lower alkylthio group, and p is an integer of 1 or 2.

The lower alkylthio is preferably an alkylthio group having a linear or branched alkyl moiety with 1 to 4 carbon atoms. Preferred examples are methylthio, ethylthio, n-propylthio, iso-propylthio, n-butylthio, isobutylthio, sec-butylthio and t-butylthio.

Preferred examples of formula (h) are 4-pyrimidinyl, 2-chloro-4-pyrimidinyl, 6-chloro-2-pyrimidinyl, 2,6-dichloro-4-pyrimidinyl, 6-chloro-2 -methylthio-4-pyrimidinyl and 2-methylthio-4-pyrimidinyl.

In formula (i), $X^9$ and $X^{10}$ are identical or different and each represents a chlorine atom, a lower alkoxy group or a lower alkylthio group.

Preferred specific examples of the lower alkoxy group may be the same as those given with regard to $X^1$.

Preferred specific examples of the lower alkylthio group may be the same as those given with regard to $X^8$.

Examples of the group of formula (i) are 4-chloro-6-methoxy-2-triazinyl, 4,6-dimethoxy-2-triazinyl, 4-methoxy-6-methylthio-2-triazinyl, 4-chloro-6-methylthio-2-triazinyl and 4,6-dimethylthio-2-triazinyl.

In formula (j), $X^{11}$ is a hydrogen or chlorine atom. Preferred examples of formula (j) are 2-pyrazinyl, 3-chloro-2-pyrazinyl, 5-chloro-2-pyrazinyl and 6-chloro-2-pyrazinyl groups.

The groups of formulas (a), (d), (e), (g), (h) and (j) are preferred as Ar.

In formula (I), $R^1$ is a $C_1$–$C_6$ alkyl group, a lower alkenyl group, a lower alkynyl group or a $C_3$–$C_7$ cycloalkyl group. The $C_1$–$C_6$ alkyl and $C_3$–$C_7$ cycloalkyl groups are preferred.

The $C_1$–$C_6$ alkyl group may be linear or branched, and examples may include methyl, n-propyl, iso-propyl, n-butyl, iso-butyl, sec-butyl, tert-butyl, n-amyl, isoamyl, sec-amyl, active amyl, tert-amyl, 1,2-dimethylpropyl, 2,2-dimethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethylpropyl and 2-ethylbutyl groups.

Unsaturated hydrocarbon groups having 3 to 5 carbon atoms in the longest carbon chain portion are preferred as the lower alkenyl group. Examples include allyl, 2-butenyl, 3-butenyl, 1-methyl-2-propenyl, 2-methyl-2-propenyl, 1,2-dimethyl-2-propenyl, 2-methyl-2-butenyl, 3-methyl-2-butenyl and 2,3-dimethyl-2-butenyl groups.

Unsaturated hydrocarbon groups having 3 to 5 carbon atoms in the longest carbon chain portion are preferred as the lower alkynyl group. Examples include 2-propynyl, 2-butynyl, 3-butynyl, 1-methyl-2-propynyl and 1,1-dimethyl-2-propynyl groups.

Examples of the $C_3$–$C_7$ cycloalkyl group are cyclopropyl, cyclobutyl, cyclopentyl, cyclohexyl and cycloheptyl.

The lower alkyl and $C_3$–$C_7$ cycloalkyl groups are especially preferred as $R^1$.

In formula (I), $R^2$ is a hydrogen atom or a $C_1$–$C_6$ alkyl group. The $C_1$–$C_6$ group is preferred.

Examples of the lower alkyl group may be the same as those given above with regard to $R^1$.

$R^1$ and $R^2$, taken together, may form a 4- to 8-membered, preferably 6- to 7-membered heterocyclic group together with the nitrogen atom to which they are bonded. The heterocyclic group may contain an oxygen atom as a ring member or may be substituted by a lower alkyl group or a lower alkylene group. Examples of the lower alkyl substituent may be the same as those given above with regard to $R^1$. Alkylene groups having 2 to 4 carbon atoms are preferred as the lower alkylene substituent. Examples are ethylene, trimethylene and tetramethylene groups.

Examples of the heterocyclic group are given below.

Four-membered heterocyclic groups:

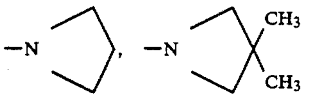

Five-membered heterocyclic groups:

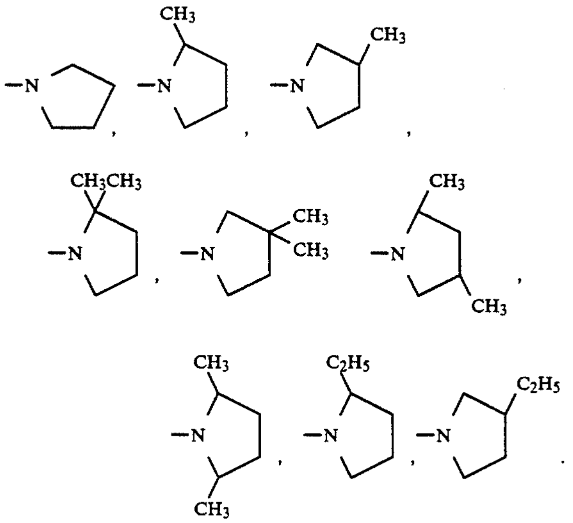

Six-membered heterocyclic groups:

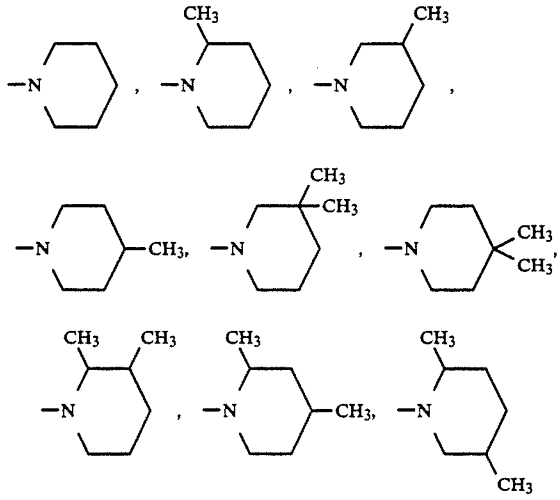

-continued

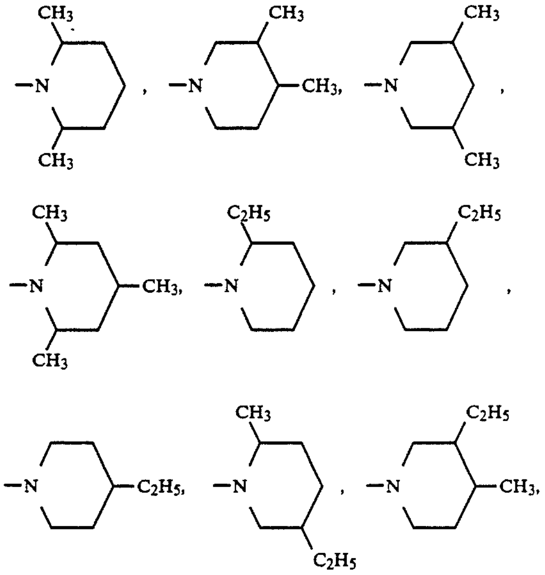

Seven-membered heterocyclic groups:

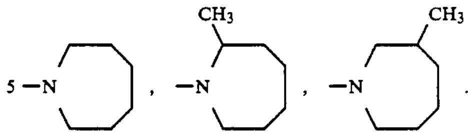

Eight-membered heterocyclic groups:

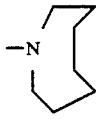

Heterocyclic groups containing an oxygen atom:

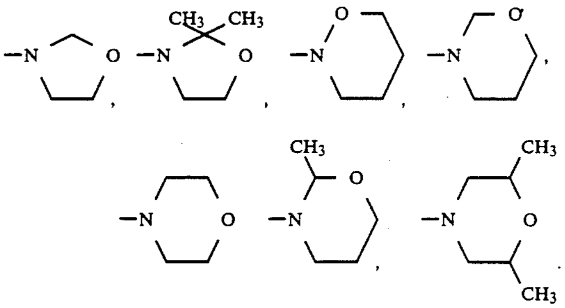

Heterocyclic groups (bicyclic groups) containing lower alkylene groups:

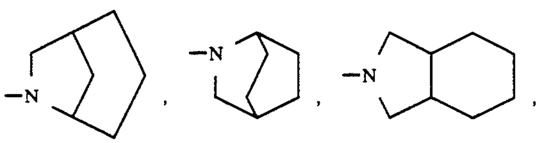

-continued
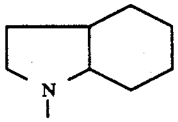 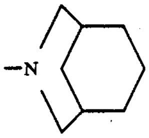, 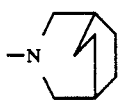,
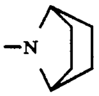, 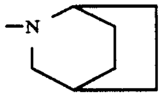.
The compounds given in Table 1 below are preferred examples of the compounds of formula (I) provided by the invention.
TABLE 1
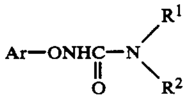
| Compound No. | Ar | $R^1$ | $R^2$ |
| --- | --- | --- | --- |
| 1 | 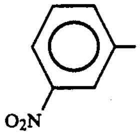 | 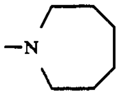 | |
| 2 | 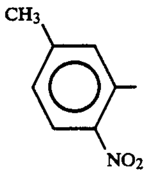 | 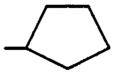 | H |
| 3 | 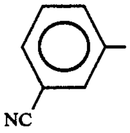 | 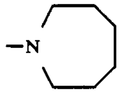 | |
| 4 | 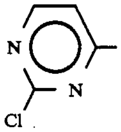 | 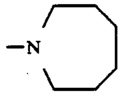 | |
| 5 | 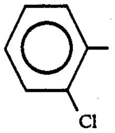 | $CH_3$ | $CH_3$ |
| 6 | " | 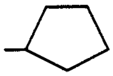 | H |
| 7 | " | 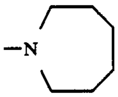 | |
TABLE 1-continued
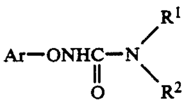
| Compound No. | Ar | $R^1$ | $R^2$ |
| --- | --- | --- | --- |
| 8 | 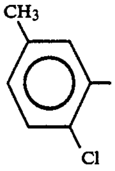 | 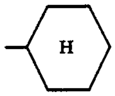 | H |
| 9 | " | 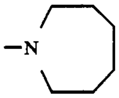 | |
| 10 | 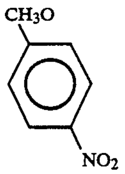 | 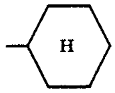 | H |
| 11 | " | 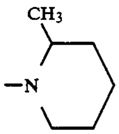 | |
| 12 | 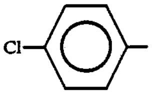 | $CH_3$ | $CH_3$ |
| 13 | 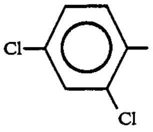 | $CH_3$ | $CH_3$ |
| 14 | " | 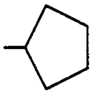 | H |
| 15 | 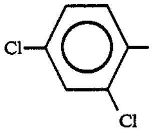 | 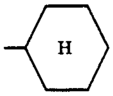 | H |
| 16 | " | 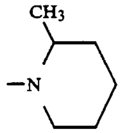 | |
| 17 | " | 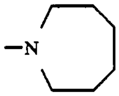 | |

TABLE 1-continued
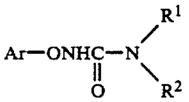
| Compound No. | Ar | $R^1$ | $R^2$ |
|---|---|---|---|
| 18 | 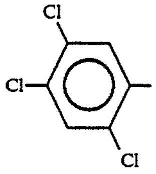 | $CH_3$ | $CH_3$ |
| 19 | 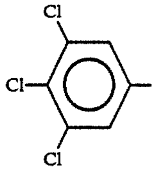 | $CH_3$ | $CH_3$ |
| 20 | 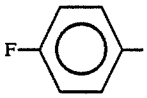 | $CH_3$ | $CH_3$ |
| 21 | 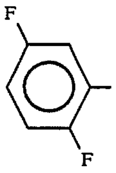 | 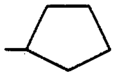 | H |
| 22 | 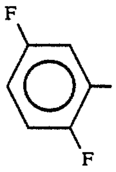 | 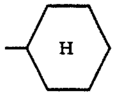 | H |
| 23 | 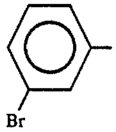 | 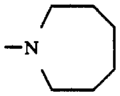 | |
| 24 | 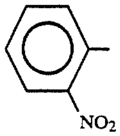 | $CH_3$ | $CH_3$ |
| 25 | " | 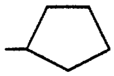 | H |
| 26 | " | $-CH_2C\equiv CH$ | $CH_3$ |
| 27 | 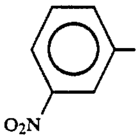 | $CH_3$ | $CH_3$ |
| 28 | " | $-CH_2CH=CH_2$ | $CH_3$ |
TABLE 1-continued
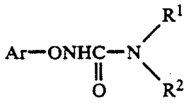
| Compound No. | Ar | $R^1$ | $R^2$ |
|---|---|---|---|
| 29 | " | 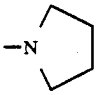 | |
| 30 | 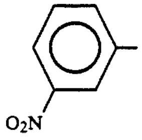 | 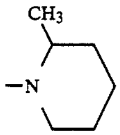 | |
| 31 | 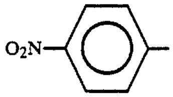 | $CH_3$ | $CH_3$ |
| 32 | 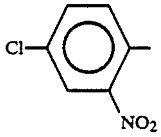 | 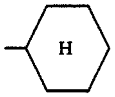 | H |
| 33 | 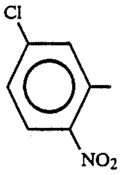 | n-$C_3H_7$ | H |
| 34 | " | i-$C_3H_7$ | H |
| 35 | " | $-CH_2CH=CH_2$ | H |
| 36 | " | sec-$C_4H_9$ | H |
| 37 | " | t-$C_4H_9$ | H |
| 38 | 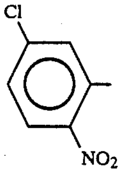 | 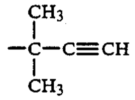 | H |
| 39 | " | 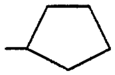 | H |
| 40 | " | 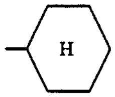 | H |
| 41 | 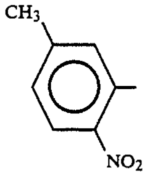 | $CH_3$ | $CH_3$ |

TABLE 1-continued
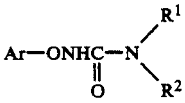
| Compound No. | Ar | $R^1$ | $R^2$ |
|---|---|---|---|
| 42 | " | 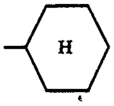 | H |
| 43 | " | 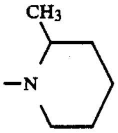 | |
| 44 | " | 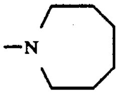 | |
| 45 | 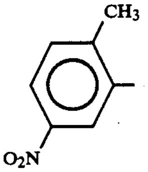 | $CH_3$ | $CH_3$ |
| 46 | 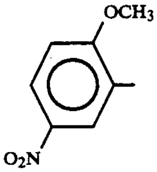 | 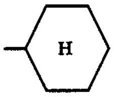 | H |
| 47 | " | 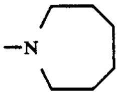 | |
| 48 | 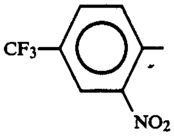 | 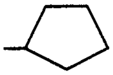 | H |
| 49 | 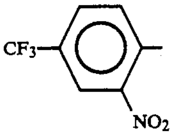 | 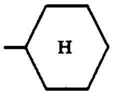 | H |
| 50 | 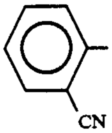 | 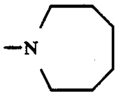 | |
| 51 | 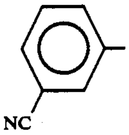 | 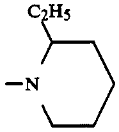 | |
TABLE 1-continued
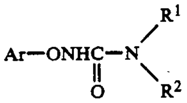
| Compound No. | Ar | $R^1$ | $R^2$ |
|---|---|---|---|
| 52 | 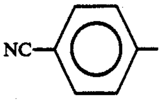 | $CH_3$ | $CH_3$ |
| 53 | 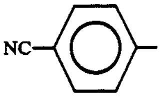 | 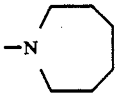 | |
| 54 | 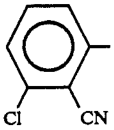 | 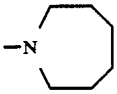 | |
| 55 | 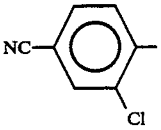 | sec-$C_4H_9$ | H |
| 56 | 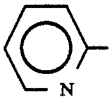 | 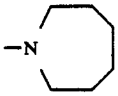 | |
| 57 | 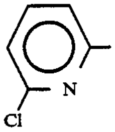 | $CH_3$ | $CH_3$ |
| 58 | " | sec-$C_4H_9$ | H |
| 59 | " | i-$C_3H_7$ | $CH_3$ |
| 60 | " | $C_2H_5$ | $C_2H_5$ |
| 61 | " | n-$C_4H_9$ | $CH_3$ |
| 62 | 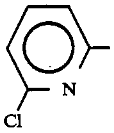 | sec-$C_4H_9$ | $CH_3$ |
| 63 | " | 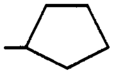 | H |
| 64 | " | 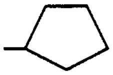 | $CH_3$ |
| 65 | " | 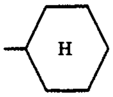 | $CH_3$ |

TABLE 1-continued
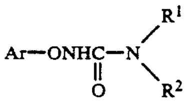
| Compound No. | Ar | $R^1$ | $R^2$ |
|---|---|---|---|
| 66 | " | 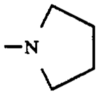 | |
| 67 | " | 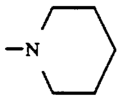 | |
| 68 | " | 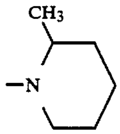 | |
| 69 | " | 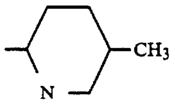 | |
| 70 | " | 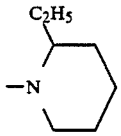 | |
| 71 | 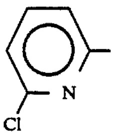 | 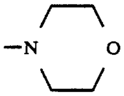 | |
| 72 | " | 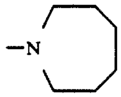 | |
| 73 | 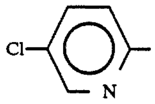 | 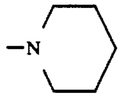 | |
| 74 | " | 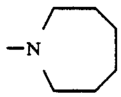 | |
| 75 | 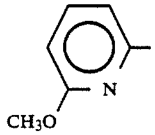 | 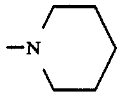 | |
| 76 | 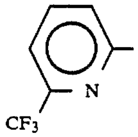 | 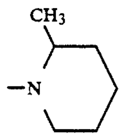 | |
TABLE 1-continued
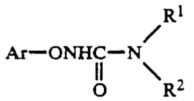
| Compound No. | Ar | $R^1$ | $R^2$ |
|---|---|---|---|
| 77 | " | 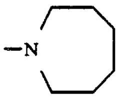 | |
| 78 | 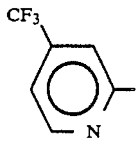 | 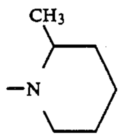 | |
| 79 | " | 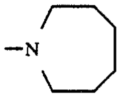 | |
| 80 | 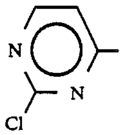 | 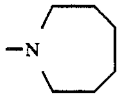 | |
| 82 | 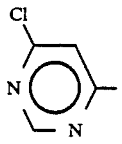 | 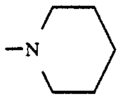 | |
| 83 | 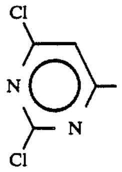 | " | |
| 84 | 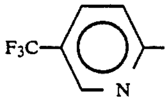 | " | |
| 85 | 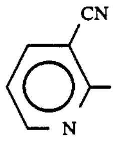 | " | |
| 86 | 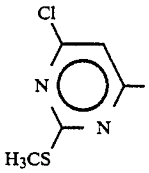 | " | |
| 87 | 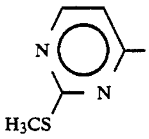 | " | |

TABLE 1-continued

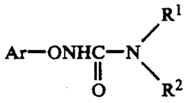

| Compound No. | Ar | $R^1$ | $R^2$ |
|---|---|---|---|
| 88 | 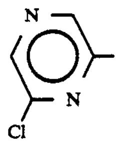 | " | |
| 89 | 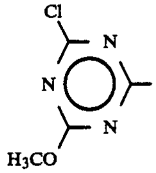 | 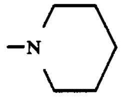 | |
| 90 | 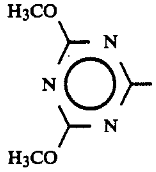 | " | |
| 91 | 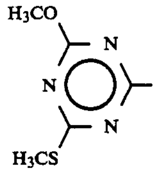 | " | |
| 92 | 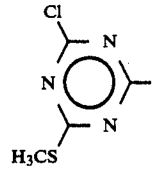 | " | |
| 93 | 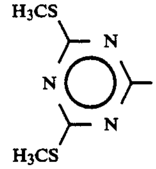 | " | |

Among the compounds tabulated in Table 1, compound Nos. 1-5, 7, 11, 16, 17, 21-26, 30, 31, 35-38, 41, 43-45, 48, 51, 53, 59-62, 64, 65, 67-72, 74, 76, 77, 79, 81, 84, 86-91, and 93 are preferred. Compound Nos. 2, 3, 7, 11, 21, 22, 43, 44, 53, 60, 62, 64, 65, 68-70, 76, 77, 84, 86-88, and 93 are especially preferred.

The substances in accordance with this invention may be in a free form, or in the form of a salt such as an acid addition salt. Examples of the acid that constitutes the acid addition salt may include, for example, mineral acids such as hydrochloric acid, sulfuric acid and phosphoric acid, and organic acids such as acetic acid, chloroacetic acid, trichloroacetic acid, maleic acid and citric acid.

According to this invention, substituted aryloxyureas of the following formula (I)-1 which are among the compounds of this invention represented by formula (I)

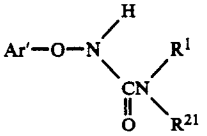

(I)-1 wherein Ar' is a group selected from the class consisting of the aryl groups of formulas (a) to (g) defined as Ar in formula (I), $R^1$ is as defined with regard to formula (I), $R^{21}$ represents a $C_1$–$C_6$ alkyl group, and $R^1$ and $R^{21}$ may form the same heterocyclic group as the 4- to 8-membered heterocyclic group formed by $R^1$ and $R^2$ in formula (I), can be produced by reacting an aryloxyamine represented by the following formula (II)

$$Ar'—ONH_2 \quad (II)$$

wherein Ar' is as defined above, with a carbamic acid chloride represented by the following formula (III)

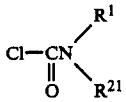

wherein $R^1$ and $R^{21}$ are as defined above with regard to formula (I), in the presence of a base.

In formula (II), Ar' is a group selected from the class of formula (a) to (g) in the definition of Ar in formula (I). The definition of $R^{21}$ differs from that of $R^2$ only in that the former does not include a hydrogen atom. $R^1$ is the same as defined with regard to formula (I). Hence, examples of the compound of formula (II) will be apparent to those skilled in the art from the specific examples of the compounds of formula (I).

The compound of formula (II) can be produced by the methods described in European Patent Application EP-No. 183174, Japanese Laid-Open Patent Publication No. 126065/1986, and Japanese Patent Application Nos. 257691/1985 and 119293/1986.

Specific examples of the compound of formula (III) will also be apparent to those skilled in the art from the definitions of $R^1$ and $R^2$ in formula (I).

The compound of formula (II) and the carbamic acid chloride of formula (III) are reacted in the presence of a base.

The base may be an organic base or an inorganic base. Preferred examples of the organic base are pyridine bases such as pyridine, picoline, lutidine and collidine and tertiary amines such as triethylamine, 1,8-diazabicyclo[5.4.0]undecene-7 and N,N-dimethylaniline.

Examples of the inorganic base are $NaHCO_3$, $KHCO_3$, $Na_2CO_3$ and $K_2CO_3$.

In the reaction, the carbamic acid chloride of formula (III) is used usually in an amount of 0.8 to 3 moles, preferably 1 to 2 moles, per mole of the compound of formula (II). Usually, the base is used in an amount of 0.5 to 20 moles, preferably 1 to 10 moles, per mole of the carbamic acid chloride in formula (III).

The reaction temperature is usually −20° to 100° C., preferably −10° to 60° C. The reaction time is usually 30 minutes to 30 hours. Desirably, the reaction is carried out with stirring.

Use of a reaction solvent is not essential. If desired, a solvent inert to the reaction may be used. Examples of such a solvent include aromatic hydrocarbons such as benzene, toluene and xylene, halogenated hydrocarbons such as chloroform, dichloromethane, carbon tetrachloride dichloroethane, trichloroethane, tetrachloroethane, chlorobenzene dichlorobenzene, tetrahydrofuran, ethyl acetate and dimethylformamide.

After the reaction, the desired compound may be obtained from the reaction mixture by conventional methods such as those shown in examples given hereinafter.

According to this invention, substituted aryloxyureas of the following formula (I)-2 which are within the compounds of formula (I)

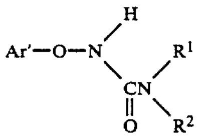

(I)-2 wherein Ar', $R^1$ and $R^2$ are as defined above, can be produced by reacting an aryloxycarbamic acid ester represented by the following formula (IV)

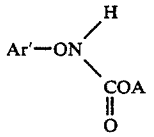

(IV)

wherein Ar' is as defined above, and A represents a substituted or unsubstituted phenyl group, with an amine represented by the following formula (V)

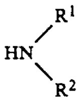

(V)

wherein $R^1$ and $R^2$ are as defined above.

In formula (IV), Ar' is as defined above, and A is a substituted or unsubstituted phenyl group. Examples of preferred substituted phenyl groups are halogenated phenyl groups such as chlorophenyl and lower alkyl-substituted phenyl groups such as tolyl.

The aryloxycarbamic acid ester of formula (IV) can be produced by reacting the aryloxyamine of formula (II) above with a compound represented by AOCOCl in the presence of a base and a solvent. The base and the solvent may be the same as those exemplified above with regard to the process for producing the compounds of formula (I)-1.

In formula (V), the definitions of $R^1$ and $R^2$ are the same as those given above with regard to formula In the reaction, the amine of formula (V) is used in an amount of usually 0.8 to 5 moles, preferably 1 to moles, per mole of the aryloxycarbamic acid ester of The reaction temperature is usually 0° to 100° C., preferably 0° to 80° C. The reaction time is usually 30 minutes to 5 hours. Desirably, the reaction is carried out with stirring.

Preferably, the reaction is carried out in a solvent. Examples of the solvent may be the same as exemplified above with regard to the process for producing the compounds of formula (I)-1. When an amine of formula (V) in which $R^2$ is a $C_1$–$C_6$ alkyl group is used, it is especially desirable to use dimethylformamide as the reaction solvent.

Furthermore, according to this invention, substituted aryloxyureas represented by the following formula (I)-3 which are among the compounds of formula (I)

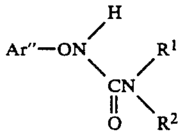

(I)-3 wherein Ar" is a group selected from the class consisting of the aryl groups of formulas (h), (i) and (j) in formula (I), and $R^1$ and $R^2$ are as defined with regard to formula (I), can be produced by reacting a chloride selected from the group consisting of chlorinated pyrimidines represented by th following formula (VI)

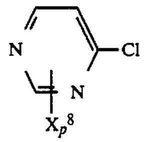

(VI)

wherein $X^8$ and p are as defined with regard to formula (I), chlorinated triazines represented by the following formula (VII)

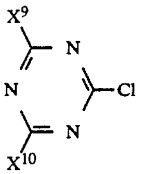

(VII)

wherein $X^9$ and $X^{10}$ are as defined with regard to formula (I), and chlorinated pyrazines represented by the following formula (VIII)

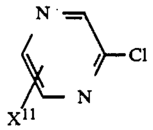

(VIII)

wherein $X^{11}$ is as defined with regard to formula (I), with an N-hydroxyurea represented by the following formula (IX)

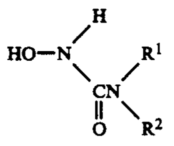

(IX)

wherein $R^1$ and $R^2$ are as defined with regard to formula (I), in the presence of a base.

The definitions of $X^8$ and p in formula (VI) are the same as in formula (I), and the definitions of $X^9$ and $X^{10}$ in formula (VII) are the same as in formula (I). $X^{11}$ in formula (VIII) is also as defined above with regard to formula (I).

Hence, specific examples of the chlorinated pyrimidines of formula (VI), the chlorinated triazines of formula (VII) and the chlorinated pyrazines of formula (VIII) will be apparent from the above-given specific examples of $X^8$, p, $X^9$ and $X^{10}$.

In formula (IX), $R^1$ and $R^2$ are as defined with regard to formula (I), and therefore, specific examples of the N-hydroxyureas of formula (IX) will also be apparent from the specific examples of these groups.

In the reaction, the N-hydroxyurea of formula (IX) is used in an amount of usually 0.8 to 5 moles, preferably 1 to 2 moles, per mole of the chloride selected from the chlorinated pyrimidines of formula (VI) and the chlorinated triazines of formula (VII).

The reaction temperature is usually −50° C. to 50° C., preferably −30° C. to 40° C. The reaction time is usually 30 minutes to 10 hours.

Desirably, the reaction is carried out with stirring. The base use in the reaction may be the same as those exemplified above with regard to the process for producing the compounds of formula (I)-1. Alkali metal alkoxides such as sodium ethoxide and potassium t-butoxide may also be used suitably.

The base is used in an amount of usually 0.5 to 10 moles, preferably 1 to 5 moles, per mole of the chloride used.

The reaction can be carried out without a solvent or in a solvent. The solvent used may be the same as those exemplified above with regard to the process for producing the compounds of formula (I)-1.

Embodiment B:

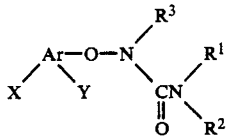

(X)

wherein

Ar represents a group selected from the class consisting of phenyl, pyridyl, pyridazinyl, pyrimidinyl and pyrazinyl groups, X and Y are identical or different and each represents a hydrogen or halogen atom, or a cyano, trifluoromethyl, nitro, lower alkoxy, lower alkylthio or lower alkoxycarbonyl group, $R^1$ represents a hydrogen atom, or a lower alkyl, lower alkenyl, lower alkynyl or $C_3$-$C_7$ cycloalkyl group, $R^2$ represents a hydrogen atom, or a lower alkyl, $R^1$ and $R^2$, taken together, may form a 4- to 8-membered heterocyclic group together with the nitrogen atom to which they are bonded, wherein the heterocyclic group may contain an oxygen atom as a ring-member atom or may be substituted by a lower alkyl group or a lower alkylene group, $R^3$ represents a group of the formula $-COR^4$, a group of formula $-CH_2OR^5$, or a lower alkyl group, $R^4$ represents a hydrogen atom, or a lower alkyl, lower haloalkyl, lower alkoxymethyl, lower alkoxy, lower alkoxy-substituted lower alkoxy or halogen-substituted lower alkoxy group, and $R^5$ represents a hydrogen atom or a lower alkyl group; and an acid addition salt thereof.

In formula (X), Ar is either phenyl

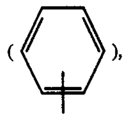

pyridyl

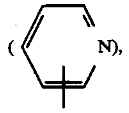

pyridazinyl

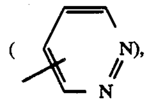

pyrimidinyl

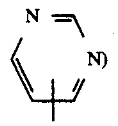

or pyrazinyl

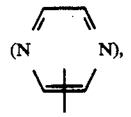

Phenyl, pyridyl and pyrazinyl are preferred as Ar, and phenyl and pyridyl are more preferred.

Pyridyl includes pyridin-2-yl and pyridin-4-yl, and pyridin-2-yl is especially preferred.

Pyridazinyl includes pyridazin-3-yl and pyridazin-4-yl.

Pyrimidinyl includes pyrimidin-2-yl and pyrimidin-4-yl. Of these, pyrimidin-4-yl is especially preferred.

Pyrazinyl means pyrazin-2-yl.

In formula (X), X and Y are atoms or groups bonded to the ring carbon atom on Ar, and each represents a hydrogen or halogen atom, or a cyano, trifluoromethyl, nitro, lower alkoxy, lower alkylthio or lower alkoxycarbonyl.

Preferred halogen atoms are fluorine, chlorine, bromine and iodine atoms.

The lower alkoxy group preferably contains a linear or branched lower alkyl moiety having 1 to 4 carbon atoms, and examples are methoxy, ethoxy, n-propoxy, iso-propoxy, n-butoxy, sec-butoxy and isobutoxy.

The lower alkylthio group preferably contains a linear or branched alkyl moiety having 1 to 4 carbon atoms, and examples include methylthio, ethylthio, n-propylthio, iso-propylthio, n-butylthio, sec-butylthio and iso-butylthio.

The lower alkoxycarbonyl group preferably contains a linear or branched alkyl moiety having 1 to 4 carbon atoms, and examples include methoxycarbonyl, ethoxycarbonyl, n-propoxycarbonyl and n-butoxycarbonyl.

The hydrogen atom, halogen atoms, particularly chlorine and bromine atoms, trifluoromethyl and nitro are preferred as X and Y, and the hydrogen atom, chlorine atom and trifluoromethyl are especially preferred.

In accordance with the definitions of Ar, X and Y given above, examples of the group

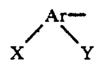

in formula (X) include substituted or unsubstituted phenyl groups such as a phenyl group, a 2-chlorophenyl group, a 3-chlorophenyl group, a 2,3-dichlorophenyl group, a 3,5-dichlorophenyl group, a 2,5-dichlorophenyl group, a 3-trifluoromethylphenyl group, a 3,5-di(trifluoromethyl)phenyl group, a 2,5-di(trifluoromethyl)-phenyl group, a 2-chloro-5-trifluoromethylphenyl group, a 5-chloro-2-trifluoromethylphenyl group, a 3-chloro-5-trifluoromethylphenyl group, a 2-bromophenyl group, a 3-bromophenyl group, a 2,5-difluorophenyl group, a 2-cyanophenyl group, a 2-cyanophenyl group, a 4-cyanophenyl group, a 2-chloro-4-cyanophenyl group, a 3-chloro-2-cyanophenyl group, a 3-nitrophenyl group, a 5-chloro-2-nitrophenyl group, a 2-chloro-5-nitrophenyl group, a 2-nitro-4-trifluoromethylphenyl group, and a 6-chloro-2-nitrophenyl group; substituted or unsubstituted pyridyl groups such as a 2-pyridyl group, a 3-chloro-2-pyridyl group, a 4-chloro-2-pyridyl group, a 5-chloro-2-pyridyl group, a 6-chloro-2-pyridyl group, a 3,5-dichloro-2-pyridyl group, a 6-methoxy-2-pyridyl group, as 3-trifluoromethyl-2-pyridyl group, a 5-trifluoromethyl-2-pyridyl group, a 4-trifluoromethyl-2-pyridyl group, a 6-trifluoromethyl-2-pyridyl group, a 3-chloro-5-trifluoromethyl-2-pyridyl group, a 5-chloro-3-trifluoromethyl-2-pyridyl group, a 6-chloro-4-trifluoromethyl-2-pyridyl group, a 3-chloro-6-trifluoromethyl-2-pyridyl group, a 5-nitro-2-pyridyl group, 6-chloro-3-nitro-2-pyridyl group and a 3-ethoxycarbonyl-2-pyridyl group; substituted or unsubstituted pyridazinyl groups such as a 3-pyridazinyl group, a 6-chloro-3-pyridazinyl group, a 4-pyridazinyl group and a 3,6-dichloro-4-pyridazinyl group; substituted or unsubstituted pyrimidinyl groups such as a 4-pyrimidinyl group, a 6-chloro-2-methylthio-4-pyrimidinyl group and a 2-methylthio-4-pyrimidinyl group; and substituted or unsubstituted pyrazinyl groups such as a 2-pyrazinyl group and a 6-chloro-2-pyrazinyl group.

In formula (X), $R^1$ represents a hydrogen atom, or a lower alkyl, lower alkenyl, lower alkynyl or $C_3$–$C_7$ cycloalkyl group.

The lower alkyl group is preferably a linear or branched alkyl group having 1 to 4 carbon atoms, and examples are methyl, ethyl, n-propyl, iso-propyl, n-butyl, sec-butyl and tert-butyl.

The lower alkenyl group is preferably an unsaturated hydrocarbon group in which the longest carbon chain portion has 3 to 5 carbon atoms. Examples include allyl, 2-butenyl, 3-butenyl, 1-methyl-2-propenyl, 2-methyl-2-propenyl, 1,2-dimethyl-2-propenyl, 2-methyl-2-butenyl, 3-methyl-2-butenyl, and 2,3-dimethyl-2-butenyl.

The lower alkynyl group is preferably an unsaturated hydrocarbon group in which the longest carbon chain portion has 3 to 5 carbon atoms, and examples include 2-propynyl, 2-butynyl, 3-butynyl, 1-methyl-2-propynyl and 1,1-dimethyl-2-propynyl.

Examples of the $C_3$–$C_7$ cycloalkyl group are cyclopropyl, cyclobutyl, cyclopentyl, cyclohexyl and cycloheptyl.

The lower alkyl and $C_3$–$C_7$ cycloalkyl groups are especially preferred as $R^1$.

In formula (X), $R^2$ represents a hydrogen atom or a lower alkyl group.

Examples of the lower alkyl group may be the same as those given above with regard to $R^1$.

The 4- to 8-membered, preferably 6 or 7-membered, heterocyclic group which $R^1$ and $R^2$ taken together can form together with the nitrogen atom to which they are bonded, may contain an oxygen atom as a ring-member atom or may be substituted by a lower alkyl or lower alkylene group. Examples of the lower alkyl substituent may be the same as those given above with regard to $R^1$. Examples of the lower alkylene substituent are preferably alkylene groups having 2 to 4 carbon atoms, such as ethylene, trimethylene and tetramethylene. The following groups may be cited as examples of the above heterocyclic group.

Four-membered groups

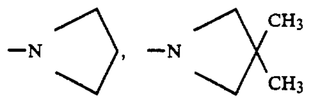

Five-membered groups

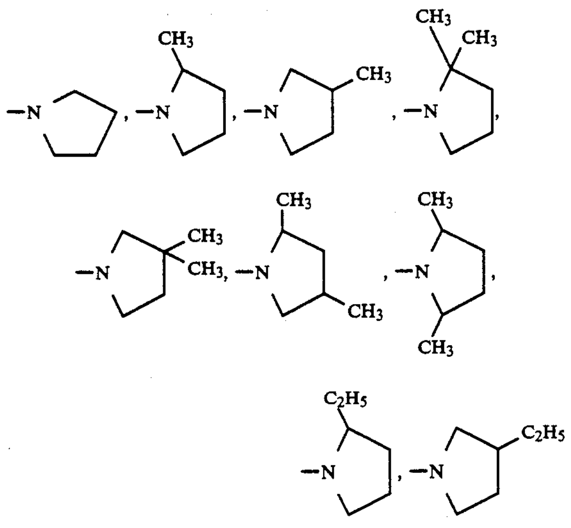

Six-membered groups

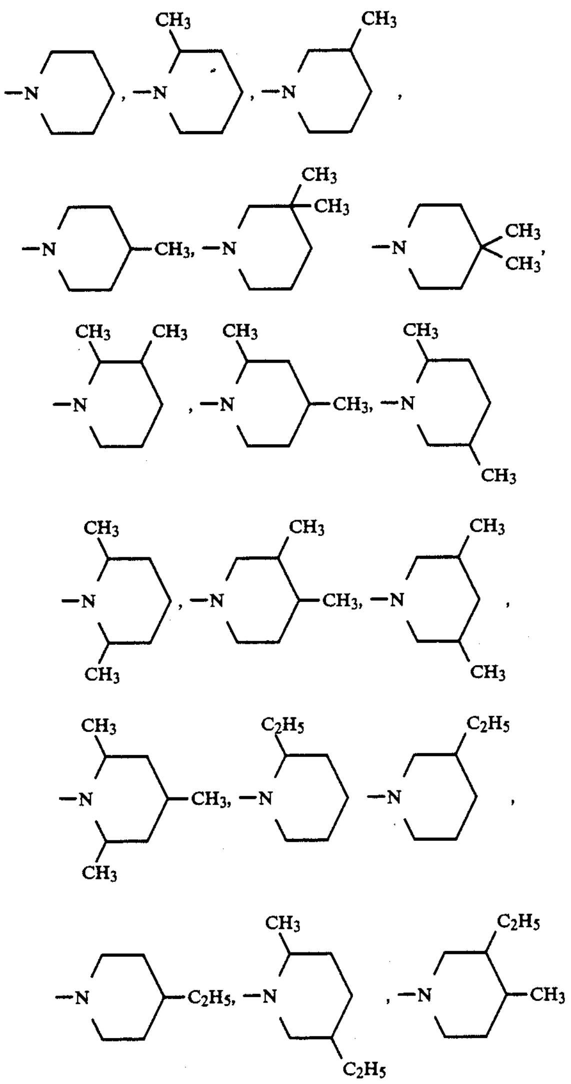

Seven-membered groups

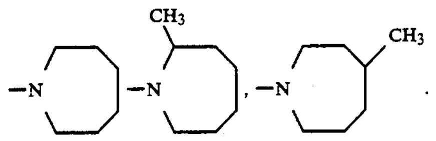

Eight-membered groups

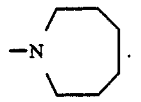

Oxygen-containing heterocyclic groups

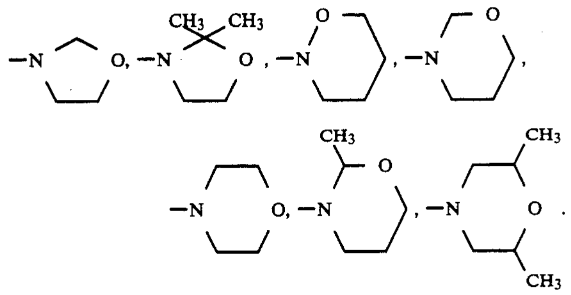

Lower alkylene-containing heterocyclic groups (bicyclic groups)

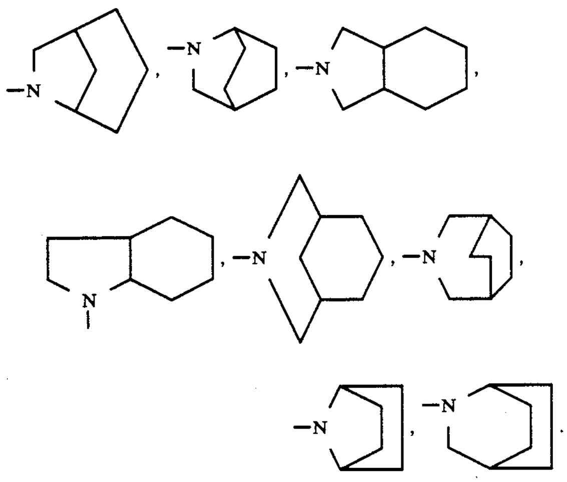

In formula (X), $R^3$ represents a group of the formula $-COR^4$, a group of the formula $-CH_2OR^5$, or a lower alkyl group. $R^4$ represents a hydrogen atom, or a lower alkyl, lower haloalkyl, lower alkoxymethyl, lower alkoxy, lower alkoxy-substituted lower alkoxy or halogen-substituted lower alkoxy group.

Specific examples of the lower alkyl and lower alkoxy groups may be the same as those given above with regard to $R^1$ and X.

Examples of the halo in the lower haloalkyl group are fluorine, chlorine, bromine and iodine. The lower haloalkyl group is preferably a linear or branched haloalkyl group having 1 to 4 carbon atoms, such as chloromethyl, trifluoromethyl, 2-chloroethyl, 2-bromoethyl, 2,2,2-trifluoroethyl and 2,3,3,3-tetrafluoropropyl-4-chlorobutyl.

Examples of the lower alkoxy moiety of the lower alkoxymethyl group are preferably the same as those given above with regard to X. Examples of the lower alkoxymethyl group are methoxymethyl, ethoxymethyl, n-propoxymethyl and n-butoxymethyl.

Examples of the two lower alkoxy moieties in the lower alkoxy-substituted lower alkoxy group may preferably be the same as those given above with regard to X. Examples of the lower alkoxy-substituted lower alkoxy group are 2-methoxyethoxy, 2-ethoxyethoxy and 3-methoxypropoxy groups. Examples of the halogen in the halogen-substituted lower alkoxy group are fluorine, chlorine, bromine and iodine. Examples of the lower alkoxy moiety may preferably be those given above with regard to X. Examples of the halogen-substituted lower alkoxy group are 2-chloroethoxy, 2,2,2-trichloroethoxy and 2-fluoroethoxy.

From the above-given specific examples of $R^4$, the groups represented by $-COR^4$ are therefore formyl ($R^4=H$), alkylcarbonyl ($R^4$=lower alkyl), haloalkylcarbonyl ($R^4$=lower haloalkyl) and alkoxymethylcarbonyl ($R^4$=lower alkoxymethyl) and alkoxycarbonyl ($R^4$=lower alkoxy), and specific examples of each of these groups will also be understood.

$R^5$ is a hydrogen atom or a lower alkyl group. Examples of the lower alkyl group may be the same as those given hereinabove with regard to $R^1$.

The group $-CH_2OR^5$ is therefore hydroxymethyl ($R^5=H$) or alkoxymethyl ($R^5$-lower alkyl), and examples of the alkoxymethyl are methoxymethyl, ethoxymethyl, n-propoxymethyl and n-butoxymethyl.

Preferred compounds of formula (x) in accordance with this invention are, for example, those described in Table 2 below.

TABLE 2

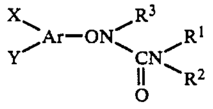

| Compound No. | 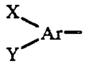 | $R^3$ | $R^1$ | $R^2$ |
|---|---|---|---|---|
| 94 | 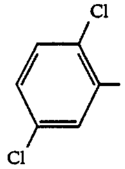 | CHO | t-$C_4H_9$ | H |
| 95 | 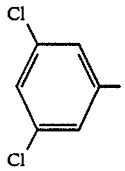 | $COCH_3$ | 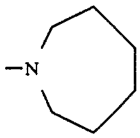 | |
| 96 | " | $CO_2CH_3$ | i-$C_3H_7$ | $CH_3$ |
| 97 | 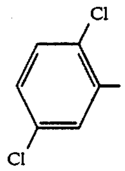 | $CH_2OH$ | n-$C_3H_7$ | H |
| 98 | 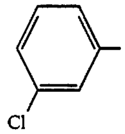 | $COCH_3$ | 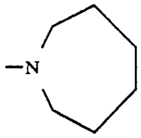 | |
| 99 | " | $COCH_2Cl$ | " | |
| 100 | 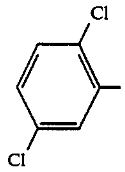 | CHO | n-$C_3H_7$ | H |

TABLE 2-continued

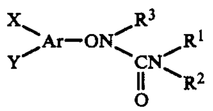

| Compound No. | 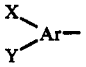 | $R^3$ | $R^1$ | $R^2$ |
|---|---|---|---|---|
| 101 | " | $COCH_3$ | " | " |
| 102 | " | $COC_2H_5$ | " | " |
| 103 | " | $COCH_2Cl$ | " | " |
| 104 | " | $COCH_2OCH_3$ | " | " |
| 105 | " | $CO_2CH_3$ | " | " |
| 106 | " | CHO | i-$C_3H_7$ | " |
| 107 | " | $COCH_3$ | " | " |
| 108 | " | $COCH_2Cl$ | " | " |
| 109 | " | $CO_2CH_3$ | " | " |
| 110 | " | $COCH_3$ | t-$C_4H_9$ | " |
| 111 | " | $COCH_2Cl$ | " | " |
| 112 | " | $CO_2CH_3$ | " | " |
| 113 | " | $COCH_3$ | n-$C_3H_7$ | $CH_3$ |
| 114 | " | CHO | 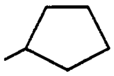 | H |
| 115 | 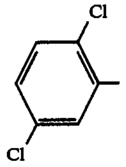 | $COCH_3$ | 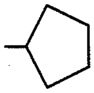 | H |
| 116 | " | $COCH_2Cl$ | " | " |
| 117 | " | $CO_2CH_3$ | " | " |
| 118 | " | $CO_2CH_3$ | 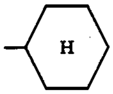 | " |
| 119 | " | $CO_2C_2H_5$ | " | " |
| 120 | " | $CO_2C_3H_7^n$ | " | " |
| 121 | " | $CO_2C_3H_7^1$ | " | " |
| 122 | 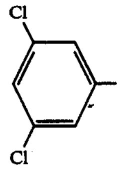 | CHO | n-$C_3H_7$ | " |
| 123 | " | $COCH_3$ | " | " |
| 124 | " | $COCH_2Cl$ | " | " |
| 125 | " | $CO_2CH_3$ | " | " |
| 126 | " | CHO | i-$C_3H_7$ | $CH_3$ |
| 127 | " | $COCH_3$ | " | " |
| 128 | " | $COC_2H_5$ | n-$C_4H_9$ | " |
| 129 | 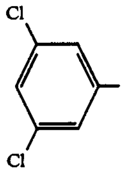 | $COCH_3$ | 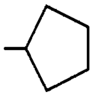 | H |
| 130 | " | $CO_2CH_3$ | " | " |
| 131 | " | $COC_2H_5$ | 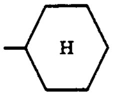 | $CH_3$ |

TABLE 2-continued
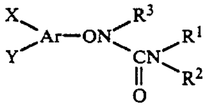
| Compound No. | 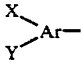 | $R^3$ | $R^1$ | $R^2$ |
|---|---|---|---|---|
| 132 | " | CHO | | 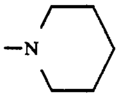 |
| 133 | " | $COCH_3$ | | " |
| 134 | " | $COC_2H_5$ | | " |
| 135 | " | $COCH_2Cl$ | | " |
| 136 | " | $COCH_3$ | | 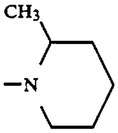 |
| 137 | " | $COC_2H_5$ | | " |
| 138 | " | $CO_2CH_3$ | | " |
| 139 | " | CHO | | 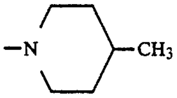 |
| 140 | 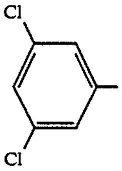 | $COCH_3$ | | 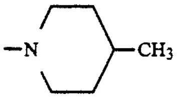 |
| 141 | " | $COC_2H_5$ | | " |
| 142 | " | CHO | | 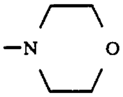 |
| 143 | " | $COCH_3$ | | " |
| 144 | " | $COCH_2Cl$ | | " |
| 145 | " | $CO_2CH_3$ | | " |
| 146 | " | CHO | | 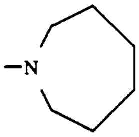 |
| 147 | " | $COC_2H_5$ | | " |
| 148 | " | $COC_3H_7^n$ | | " |
| 149 | " | $COC_3H_7^i$ | | " |
| 150 | " | $COCH_2Cl$ | | " |
| 151 | " | $CO_2CH_3$ | | " |
| 152 | " | $CO_2CH_3$ | | 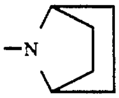 |

TABLE 2-continued
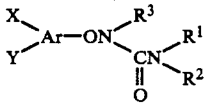
| Compound No. | 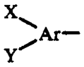 | $R^3$ | $R^1$ | $R^2$ |
|---|---|---|---|---|
| 153 | 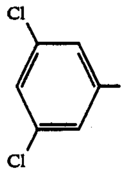 | $COCH_3$ | 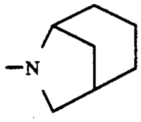 | |
| 154 | " | " | 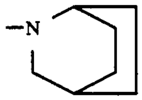 | |
| 155 | 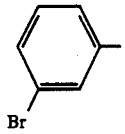 | CHO | 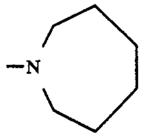 | |
| 156 | 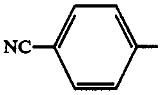 | " | " | |
| 157 | " | $COCH_3$ | " | |
| 158 | 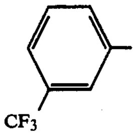 | CHO | 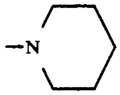 | |
| 159 | " | $COCH_3$ | " | |
| 160 | " | CHO | 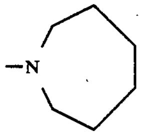 | |
| 161 | " | $COCH_3$ | " | |
| 162 | 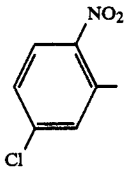 | CHO | sec-$C_4H_9$ | H |
| 163 | " | $COCH_3$ | " | " |
| 164 | " | $COCH_2Cl$ | " | " |
| 165 | " | $CO_2CH_3$ | " | " |
| 166 | " | $CH_2OH$ | " | " |
| 167 | " | $COCH_3$ | 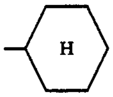 | " |
| 168 | " | $CO_2CH_3$ | " | " |

TABLE 2-continued
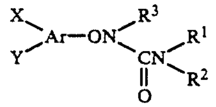
| 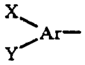 Compound No. | | $R^3$ | $R^1$ | $R^2$ |
|---|---|---|---|---|
| 169 | 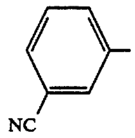 | CHO | 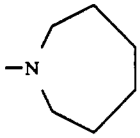 | |
| 170 | " | $COCH_3$ | " | |
| 171 | 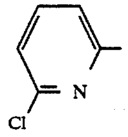 | $COCH_3$ | 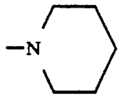 | |
| 172 | " | $COC_2H_5$ | " | |
| 173 | " | $CO_2CH_3$ | " | |
| 174 | 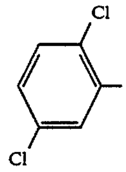 | $CH_2OC_2H_5$ | n-$C_3H_7$ | H |
| 175 | 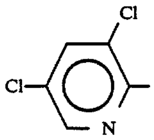 | $CO_2C_2H_5$ | 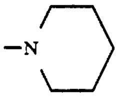 | |
| 176 | 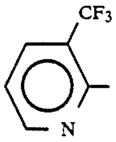 | " | " | |
| 177 | " | " | n-$C_3H_7$ | H |
| 178 | 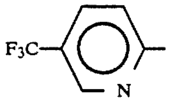 | " | " | " |
| 179 | " | " | 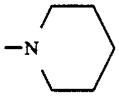 | |
| 180 | 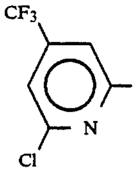 | $COCH_3$ | n-$C_3H_7$ | H |
| 181 | " | $CO_2C_2H_5$ | " | " |
| 182 | " | $CO_2C_2H_5$ | 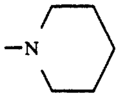 | |

TABLE 2-continued
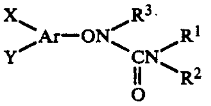
| Compound No. | 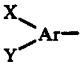 | $R^3$ | $R^1$ | $R^2$ |
|---|---|---|---|---|
| 183 | " | $CO_2CH_3$ | | " |
| 184 | 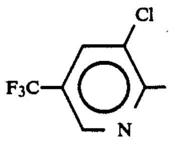 | $CO_2C_2H_5$ | n-$C_3H_7$ | H |
| 185 | " | " | 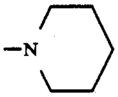 | |
| 186 | 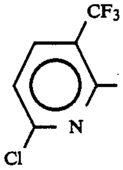 | $CO_2C_2H_5$ | 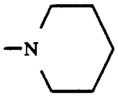 | |
| 187 | 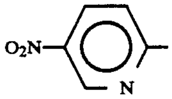 | " | | " |
| 188 | 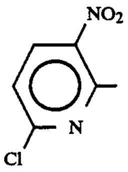 | " | n-$C_3H_7$ | H |
| 189 | 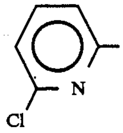 | $CO_2CH_3$ | 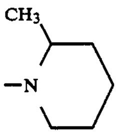 | |
| 190 | " | " | 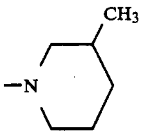 | |
| 191 | " | " | 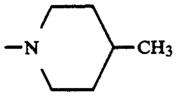 | |
| 192 | " | " | 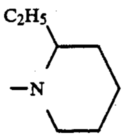 | |

TABLE 2-continued
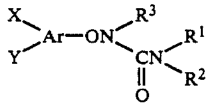
| Compound No. | 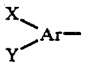 | $R^3$ | $R^1$ | $R^2$ |
|---|---|---|---|---|
| 193 | " | " | 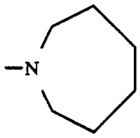 | |
| 194 | " | " | 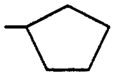 | $CH_3$ |
| 195 | 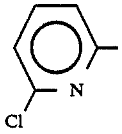 | $CO_2C_2H_5$ | 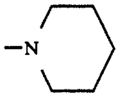 | |
| 196 | " | " | 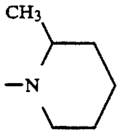 | |
| 197 | " | " | 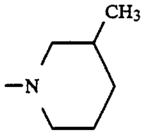 | |
| 198 | " | " | 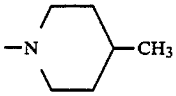 | |
| 199 | " | " | 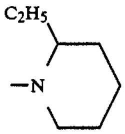 | |
| 200 | " | " | 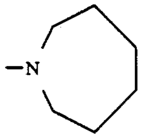 | |
| 201 | " | " | 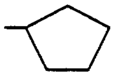 | $CH_3$ |
| 202 | 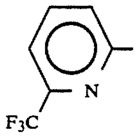 | $CO_2CH_3$ | 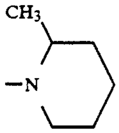 | |
| 203 | " | $CO_2C_2H_5$ | " | |
| 204 | " | $CO_2(CH_2)_2CH_3$ | " | |

TABLE 2-continued
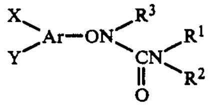
| Compound No. | 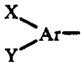 | $R^3$ | $R^1$ | $R^2$ |
|---|---|---|---|---|
| 205 | " | 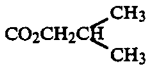 | " | |
| 206 | 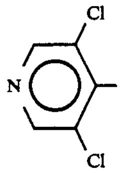 | $CO_2C_2H_5$ | n-$C_3H_7$ | H |
| 207 | 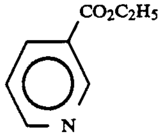 | $CO_2C_2H_5$ | 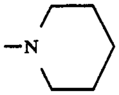 | |
| 208 | 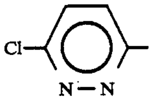 | " | n-$C_3H_7$ | H |
| 209 | " | " | 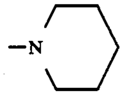 | |
| 210 | 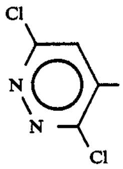 | " | " | |
| 211 | 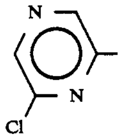 | $CO_2C_2H_5$ | n-$C_3H_7$ | H |
| 212 | " | " | 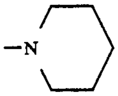 | |
| 213 | 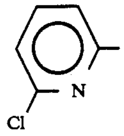 | $CO_2CH_3$ | n-$C_4H_9$ | $CH_3$ |
| 214 | " | " | sec-$C_4H_9$ | " |
| 215 | " | " | 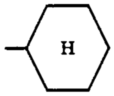 | " |

TABLE 2-continued
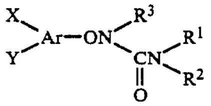
| Compound No. | 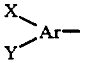 | $R^3$ | $R^1$ | $R^2$ |
|---|---|---|---|---|
| 216 | 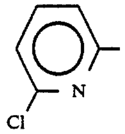 | $CO_2CH_3$ | $C_2H_5$ | $C_2H_5$ |
| 217 | ″ | $CO_2C_2H_5$ | n-$C_4H_9$ | $CH_3$ |
| 218 | ″ | ″ | sec-$C_4H_9$ | ″ |
| 219 | ″ | ″ | 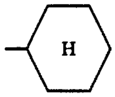 | ″ |
| 220 | ″ | ″ | $C_2H_5$ | $C_2H_5$ |
| 221 | ″ | ″ | 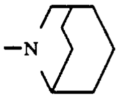 | |
| 222 | 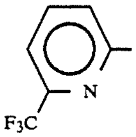 | $CO_2(CH_2)_2OCH_3$ | 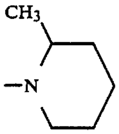 | |
| 223 | ″ | $CO_2CH_2CCl_3$ | ″ | |
| 224 | 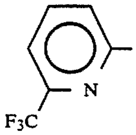 | $CO_2C_2H_5$ | 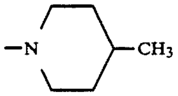 | |
| 225 | ″ | ″ | 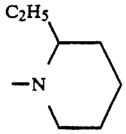 | |
| 226 | ″ | ″ | 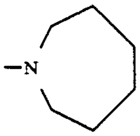 | |
| 227 | ″ | ″ | 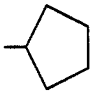 | $CH_3$ |
| 228 | ″ | ″ | 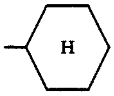 | $CH_3$ |
| 229 | ″ | ″ | n-$C_4H_9$ | $CH_3$ |

TABLE 2-continued
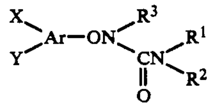
| Compound No. | 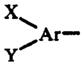 | $R^3$ | $R^1$ | $R^2$ |
|---|---|---|---|---|
| 230 | 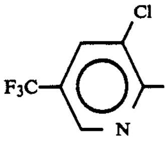 | " | 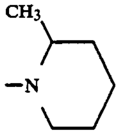 | |
| 231 | " | " | 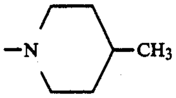 | |
| 232 | " | " | 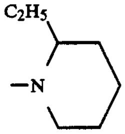 | |
| 233 | " | " | 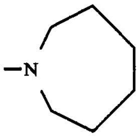 | |
| 234 | " | " | 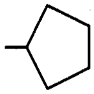 | $CH_3$ |
| 235 | 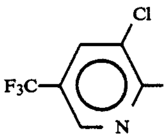 | $CO_2C_2H_5$ | sec-$C_4H_9$ | $CH_3$ |
| 236 | " | " | $C_2H_5$ | $C_2H_5$ |
| 237 | 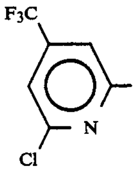 | " | 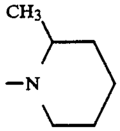 | |
| 238 | " | " | 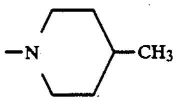 | |
| 239 | " | " | 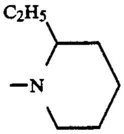 | |

TABLE 2-continued
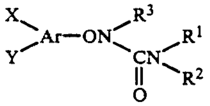
| Compound No. | 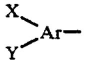 | $R^3$ | $R^1$ | $R^2$ |
|---|---|---|---|---|
| 240 | " | " | 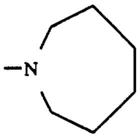 | |
| 241 | " | " | 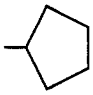 | $CH_3$ |
| 242 | " | " | sec-$C_4H_9$ | $CH_3$ |
| 243 | " | " | $C_2H_5$ | $C_2H_5$ |
| 244 | 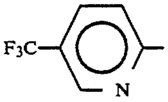 | " | 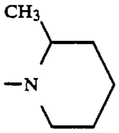 | |
| 245 | 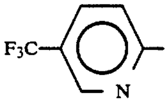 | $CO_2C_2H_5$ | 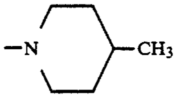 | |
| 246 | " | " | 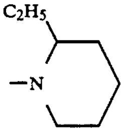 | |
| 247 | " | " | 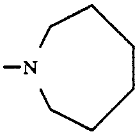 | |
| 248 | " | " | 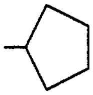 | $CH_3$ |
| 249 | " | " | sec-$C_4H_9$ | $CH_3$ |
| 250 | " | " | $C_2H_5$ | $C_2H_5$ |
| 251 | 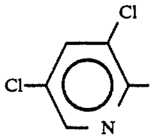 | | 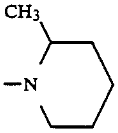 | |
| 252 | " | " | 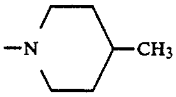 | |

TABLE 2-continued

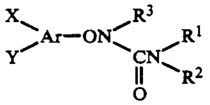

| Compound No. | 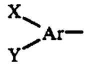 | $R^3$ | $R^1$ | $R^2$ |
|---|---|---|---|---|
| 253 | " | " | 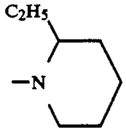 | |
| 254 | 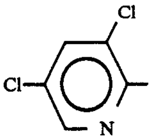 | $CO_2C_2H_5$ | 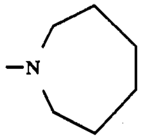 | |
| 255 | " | " | 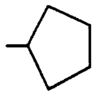 | $CH_3$ |
| 256 | " | " | sec-$C_4H_9$ | $CH_3$ |
| 257 | " | " | $C_2H_5$ | $C_2H_5$ |
| 258 | 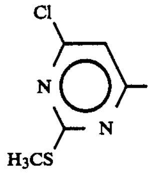 | $CH_3$ | 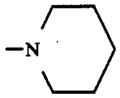 | |
| 259 | 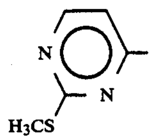 | " | | " |

Among the compounds given in Table 2, compound Nos. 94–102, 105–112, 114–118, 120, 126–128, 132–141, 143–155, 158–162, 165, 166, 171–173, 175, 177, 179, 181–183, 185–187, 206–209 and 212 are preferred. Especially preferred are compound Nos. 94–96, 98, 99, 101, 105–108, 114–118, 126, 127, 132, 133, 135, 136, 138, 146, 147, 148, 149, 151, 155, 158, 160, 161, 171, 172, 173, 175, 177, 179, 182, 183, 185, 186, 187 and 212.

The substances in accordance with this invention may be in a free form, or in the form of a salt such as an acid addition salt. Examples of the acid that constitutes the acid addition salt may include, for example, mineral acids such as hydrochloric acid, sulfuric acid and phosphoric acid, and organic acids such as chloroacetic acid, dichloroacetic acid, trichloroacetic acid, maleic acid and citric acid.

According to this invention, aryloxyureas of the following formula (X)-1, which are encompassed within formula (X),

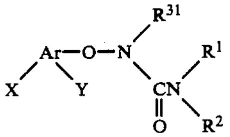

(X)-1 wherein Ar, X, Y, $R^1$ and $R^2$ are as defined with regard to formula (I), $R^{31}$ represents a group of the formula $-COR^{41}$, a group of the formula $-CH_2OR^{51}$ or a lower alkyl group, $R^{41}$ represents a lower alkyl, lower haloalkyl, lower alkoxymethyl, lower alkoxy, lower alkoxy-substituted lower alkoxy or halogen-substituted lower alkoxy group, and $R^{51}$ represents a lower alkyl group, can be produced by reacting a compound represented by formula (XI)

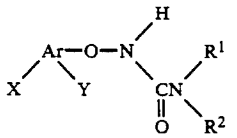

(XI)

wherein Ar, X, Y, $R^1$ and $R^2$ are as defined with regard to formula (X) with a compound represented by the following formula (XII)

$R^{31}$—Cl (XII)

wherein $R^{31}$ is as defined with regard to formula (X)-1 in the presence of a base.

In formula (XI), the definitions of Ar, X, Y, $R^1$ and $R^2$ are the same as those given with regard to formula (X). Accordingly, specific examples of the compound of formula (XI) will be apparent to those skilled in the art from the above-given specific examples of the compound of formula (X). The compound of formula (XI) can be produced by, or basically in accordance with, the methods described in European Patent Application EP-No. 183174, Japanese Laid-Open Patent Publication No. 126065/1986 and Japanese Patent Application Nos. 257691/1985 and 119293/1986.

As is clear from the definition of $R^{31}$, the compound represented by formula (XII) is an acid chloride or chloroformate of the following formula $R^{41}$—COCl wherein $R^{41}$ represents a lower alkyl, lower haloalkyl, lower alkoxymethyl, lower alkoxy, lower alkoxy-substituted lower alkoxy or halogen-substituted lower alkoxy group, or a lower alkoxymethyl chloride represented by the following formula $R^{51}OCH_2Cl$ wherein $R^{51}$ is a lower alkyl group.

In the above formula, examples of the lower alkyl group represented by $R^{41}$ and $R^{51}$ may be the same as those given above with regard to $R^1$ in formula (X). Examples of the lower haloalkyl, lower alkoxymethyl and lower alkoxy groups for $R^{41}$ may be the same as those given above with regard to $R^4$ in formula (X). Accordingly, specific examples of the acid chloride, chloroformate and lower alkoxymethyl chloride of the above formula will be apparent from the specific examples of $R^{41}$ and $R^{51}$.

The compound of formula (XI) and the compound of formula (XII) are reacted in the presence of a base.

The base may be an organic or an inorganic base. Examples Of preferred organic bases are pyridine bases such as pyridine, picoline, lutidine and collidine and tertiary amines such as triethylamine, 1,8-diazabicyclo[5.4.0]undecene-7 and N,N-dimethylaniline. Examples of the inorganic base are $NaHCO_3$, $KHCO_3$, $Na_2CO_3$ and $K_2CO_3$.

In the reaction, the compound of formula (XII) is used in an amount of 0.8 to 3 moles, preferably 1 to 2 moles, per mole of the compound of formula (XI). The base is used usually in an amount of 0.5 to 10 moles, preferably 1 to 5 moles, per mole of the compound of formula (XII).

The reaction temperature is usually 0° to 100° C., preferably 0° to 60° C., and the reaction time is usually 30 minutes to 30 hours. Preferably, the reaction is carried out with stirring.

Use of a reaction solvent is not essential. If desired, solvents inert to the reaction may be used. Examples include aromatic hydrocarbons such as benzene, toluene and xylene, halogenated hydrocarbons such as chloroform dichloromethane, carbon tetrachloride, dichloroethane, trichloroethane, tetrachloroethane, chlorobenzene, dichlorobenzene, tetrahydrofuran, ethyl acetate and dimethylformamide.

After the reaction, the desired compound can be obtained from the reaction mixture by customary methods such as those shown in examples given hereinafter.

According to this invention, aryloxyureas of the following formula (X)-2, which correspond to formula (X) in which $R^3$ is —COH,

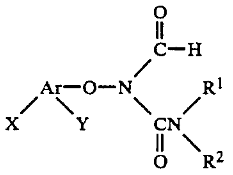

(X)-2 wherein Ar, X, Y, $R^1$ and $R^2$ are as defined with regard to formula (X) can be produced by reacting the compound of formula (XI) given above with a compound represented by the following formula (XIII)

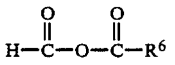

(XIII)

wherein $R^6$ represents a lower alkyl group.

In formula (XIII), $R^6$ represents a lower alkyl group, and its examples are the same as those shown with regard to $R^1$ in formula (X).

The compound of formula (XIII) can be synthesized, for example, by a customary method of stirring formic acid and an acid anhydride represented by the general formula $(R^6CO)_2O$ at a temperature of 50° to 80° C. The synthesized reaction mixture may, as required, be directly used in the above process of this invention without isolation of the compound (XIII).

In the reaction, the compound of formula (XIII) is used in an amount of 3 to 10 moles, preferably 3 to 7 moles, per mole of the compound of formula (XI).

The reaction temperature is usually 40° to 80° C., and the reaction time is usually 1 to 10 hours. The reaction is preferably carried out with stirring.

The reaction may be carried out without a solvent or in a solvent. The same solvents as those given above which can be used in the above process of this invention using the compound of formula (III) may be used.

Furthermore, according to this invention, aryloxyureas represented by the following formula (X)-3, which correspond to formula (X) in which $R^3$ is —$CH_2OH$,

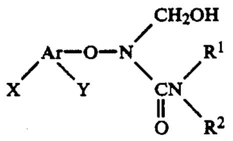

(X)-3 wherein Ar, X, Y, $R^1$ and $R^2$ are as defined with regard to formula (X), may be produced by reacting the compound represented by formula (XI) with formaldehyde.

In the reaction, 1 to 5 moles of formaldehyde is usually used per mole of the compound of formula (XI).

Usually, the reaction temperature is 0° to 50° C., and the reaction time is 0.5 to 10 hours. Desirably, the reaction is carried out with stirring.

Commercial formalin may be directly used as a source of formaldehyde in the reaction.

According to this invention, aryloxyureas represented by the following formula (X)-4, which are among the compounds of formula (X) given above,

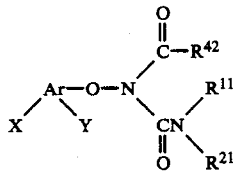

(X)-4 wherein Ar, X and Y are as defined with regard to formula (X), $R^{11}$ represents a lower alkyl, lower alkenyl, lower alkynyl or $C_3$-$C_7$ cycloalkyl group, $R^{21}$ represents a lower alkyl group, and $R^{11}$ and $R^{21}$, taken together, may form a 4- to 8-membered heterocyclic group together with the nitrogen atom to which they are bonded, said heterocyclic group optionally containing an oxygen atom as a ring-member atom or being substituted by a lower alkyl or alkylene group, and $R^{42}$ represents a lower alkoxy, lower alkoxy-substituted lower alkoxy, or halogen-substituted lower alkoxy group, can be produced by reacting a compound represented by the following formula (XIV)

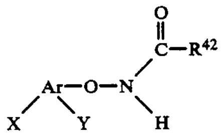

(XIV)

wherein Ar, X and Y are as defined with regard to formula (X), and $R^{42}$ is as defined with regard to formula (X)-4, with a carbamoyl chloride represented by the following formula (XV)

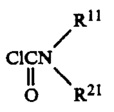

(XV)

wherein $R^{11}$ and $R^{12}$ are as defined with regard to formula (X)-4, in the presence of a base.

The base may be an organic or an inorganic base. Examples of preferred organic bases are pyridine bases such as pyridine, picoline, lutidine and collidine and tertiary amines such as triethylamine, 1,8-diazabicyclo[5.4.0]undecene-7 and N,N-dimethylaniline. Examples of the inorganic base are $NaHCO_3$, $KHCO_3$, $Na_2CO_3$ and $K_2CO_3$.

In the reaction, the compound of formula (XV) is used in an amount of 0.8 to 3 moles, preferably 1 to 2 moles, per mole of the compound of formula (XIV). The base is used usually in an amount of 0.5 to 20 moles, preferably 1 to 10 moles, per mole of the compound of formula (XIV). The reaction temperature is usually 0° to 100° C., preferably 20° to 80° C., and the reaction time is usually 1 to 100 hours. Preferably, the reaction is carried out with stirring.

Use of a reaction solvent is not essential. If desired, solvents inert to the reaction may be used. Examples include aromatic hydrocarbons such as benzene, toluene and xylene, halogenated hydrocarbons such as chloroform dichloromethane, carbon tetrachloride, dichloroethane, trichloroethane, tetrachloroethane, chlorobenzene, dichlorobenzene, tetrahydrofuran, ethyl acetate and dimethylformamide.

After the reaction, the desired compound may be obtained by conventional methods such as the one shown in the examples to be given hereinafter.

Furthermore, according to this invention, aryloxyureas represented by the following formula (X)-5, which are within the compounds of formula (X),

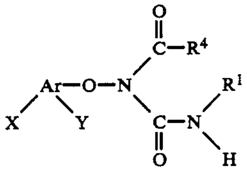

(X)-5 wherein Ar, X, Y, $R^1$ and $R^4$ are as defined hereinabove with regard to formula (X), can be produced by reacting a compound represented by formula (XVI),

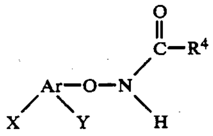

(XVI)

wherein Ar, X, Y and $R^4$ are as defined above, with an isocyanate ester represented by the following formula (XVII)

$$O{=}C{=}N{-}R^{12} \quad (XVII)$$

wherein $R^{12}$ represents a lower alkyl, lower alkenyl, lower alkynyl or $C_3$-$C_7$ cycloalkyl group.

In the reaction, 0.8 to 10 moles, preferably 1 to 5 moles, of the isocyanate of formula (XVII) is used per mole of the compound of formula (XVI). The reaction temperature is usually 0° to 100° C., preferably 20° to 80° C., and the reaction time is usually 1 to 100 hours. Desirably, the reaction is carried out with stirring.

Use of a reaction solvent is not essential. If desired, solvents inert to the reaction may be used. Examples include aromatic hydrocarbons such as benzene, toluene and xylene, halogenated hydrocarbons such as chloroform, dichloromethane, carbon tetrachloride, dichloroethane, trichloroethane, tetrachloroethane, chlorobenzene, dichlorobenzene, tetrahydrofuran, ethyl acetate and dimethylformamide.

In the reaction, 0.1 to 30 mole %, based on the compound of formula (XVII) of a tertiary amine such as triethylamine may be added.

Furthermore, according to this invention, aryloxyureas of the following formula (X)-6, which are within the compounds of formula (X),

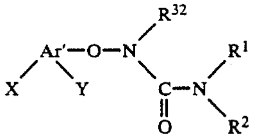
(X)-6 wherein Ar' represents a group selected from pyrimidinyl and pyridazinyl, $R^{32}$ is a lower alkyl group, and X, Y, $R^1$ and $R^2$ are as defined with regard to formula (X), can be produced by reacting a compound represented by the following formula (XVIII)

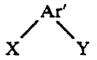
(XVIII)

wherein Ar' is defined above with regard to formula (X)-6, and X and Y are as defined with regard to formula (X), with an N-hydroxyurea represented by the following formula (XIX),

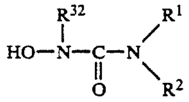
(XIX)

wherein $R^{32}$ is as defined with regard to formula (X)-6, and $R^1$ and $R^2$ are as defined with regard to formula (X), in the presence of a base.

The base may be a pyridine base such as pyridine, picoline, lutidine and collidine, a tertiary amine such as triethylamine, 1,8-diazabicyclo[5.4.0]undecene-7 or N,N-dimethylaniline, or an inorganic base such as $NaHCO_3$, $KHCO_3$, $Na_2CO_3$ and $K_2CO_3$, or an alkali metal alkoxide such as sodium ethoxide or potassium t-butoxide.

The amount of the N-hydroxyurea of formula (XIX) is 0.5 to 10 moles, preferably 1 to 5 moles, per mole of the compound of formula (XVIII). The reaction temperature is usually −50° to +50° C., preferably −40° to +40° C., and the reaction time is usually 0.5 to 10 hours. Preferably, the reaction is carried out with stirring. Use of a reaction solvent is not essential. If desired, solvents inert to the reaction, for example an aromatic hydrocarbon such as benzene, toluene or xylene, a halogenated hydrocarbon such as chloroform, dichloromethane, carbon tetrachloride, dichloroethane, trichloroethane, tetrahydrofuran, ethyl acetate and dimethylformamide, may be used.

Embodiment C:

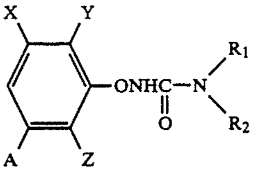
(XX)

wherein A is a halogen atom or a trifluoromethyl group, each of X, Y and Z, which may be the same or different, is a hydrogen atom, a halogen atom or a trifluoromethyl group, $R_1$ is a $C_1$–$C_6$ alkyl group, a lower alkoxyl group, a lower alkoxyl-substituted lower alkyl group, a cyclo-lower alkyl-substituted lower alkyl group, a lower alkenyl group, a lower alkynyl group, a lower haloalkyl group, a lower haloalkenyl group or a $C_3$–$C_9$ non-aromatic cyclic hydrocarbon group, and $R_2$ is a hydrogen atom, a $C_1$–$C_6$ alkyl group, a lower alkenyl group or a lower alkynyl group, or $R_1$ and $R_2$ form, together with the nitrogen atom to which they are bonded, a 3–8 member ring (which may be a bicyclo ring) which may contain a double bond or an oxygen atom within the ring and may have one or more branches.

Three methods can be used for the production of the substituted phenoxy urea (XX):

(1) A process for preparing a substituted phenoxy urea having the formula:

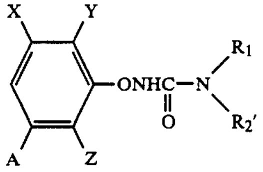
(XX)-I wherein A is a halogen atom or a trifluoromethyl group, each of X, Y and Z is a hydrogen atom, a halogen atom or a trifluoromethyl group, $R_1$ is a $C_1$–$C_6$ alkyl group, a lower alkoxyl group, a lower alkoxyl-substituted lower alkyl group, a cyclo-lower alkyl-substituted lower alkyl group, a lower alkenyl group, a lower alkynyl group, a lower haloalkyl group, a lower haloalkenyl group or a $C_3$–$C_9$ non-aromatic cyclic hydrocarbon group, and $R_2{}^1$ is a $C_1$–$C_6$ alkyl group, a lower alkenyl group or a lower alkynyl group, or $R_1$ and $R_2{}^1$ form, together with the nitrogen atom to which they are bonded, a 3–8 member ring (which may be a bicyclo ring) which may contain a double bond or an oxygen atom within the ring and may have one or more branches, which comprises reacting a phenoxyamine having the formula:

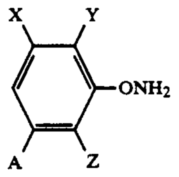

(XXI)

wherein A, X, Y and Z are as defined above, with a carbamic acid chloride having the formula:

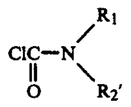

(XXII)

wherein $R_1$ and $R_2{}^1$ are as defined above, in the presence of a base;

(2) A process for preparing a substituted phenoxy urea having the formula:

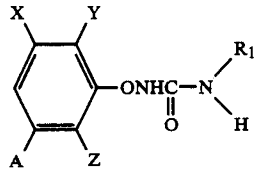

(XX)-II wherein A is a halogen atom or a trifluoromethyl group, each of X, Y and Z is a hydrogen atom, a halogen atom or a trifluoromethyl group, and $R_1$ is a $C_1$–$C_6$ alkyl group, a lower alkoxyl group, a lower alkoxyl-substituted lower alkyl group, a cyclo-lower alkyl-substituted lower alkyl group, a lower alkenyl group, a lower alkynyl group, a lower haloalkyl group, a lower haloalkenyl group or a $C_3$–$C_9$ non-aromatic cyclic hydrocarbon group, which comprises reacting a phenoxyamine having the formula:

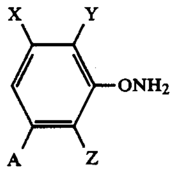

(XXI)

wherein A, X, Y and Z are as defined above, with an isocyanate having the formula:

OCN—$R_1$ (XXIII)

wherein $R_1$ is as defined above; and (3) A process for preparing a substituted phenoxy urea having the formula:

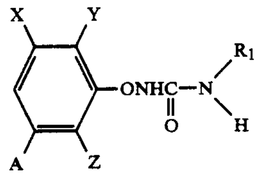

(XX)-III wherein A is a halogen atom or a trifluoromethyl group, each of X, Y and Z is a hydrogen atom, a halogen atom or a trifluoromethyl group, and $R_1$ is a $C_1$–$C_6$ alkyl group, a lower alkoxyl group, a lower alkoxyl-substituted lower alkyl group, a cyclo-lower alkyl-substituted lower alkyl group, a lower alkenyl group, a lower alkynyl group, a lower haloalkyl group, a lower haloalkenyl group or a $C_3$–$C_9$ non-aromatic cyclic hydrocarbon group, which comprises reacting a phenoxy carbamate having the formula:

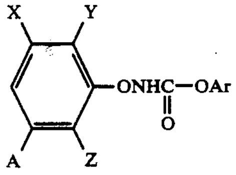

(XXIV)

wherein A, X, Y and Z are as defined above, and Ar is an aryl group, with an amine having the formula:

$R_1NH_2$ (XXV)

wherein $R^1$ is as defined above.

Further, the present invention provides a herbicide comprising a herbicidally effective amount of a substituted phenoxy urea of the formula I and a carrier.

Now, the present invention will be described in detail with reference to the preferred embodiments.

The substituted phenoxy urea of the present invention is represented by the formula (XX). In the formula (XX), the halogen for A is chlorine, fluorine, bromine or iodine. Likewise, the halogen for each of X, Y and Z is chlorine, fluorine, bromine or iodine. As the $C_1$–$C_6$ alkyl group for $R_1$, there may be mentioned methyl, ethyl, n-propyl, isopropyl, n-butyl, isobutyl, sec-butyl, tert-butyl, n-amyl, isoamyl, sec-amyl, active amyl, tert-amyl, 1,2-dimethylpropyl, 2,2-dimethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethylpropyl and 2-ethylbutyl. Likewise, the lower alkoxyl group is a $C_1$–$C_4$ alkoxyl group such as methoxy, ethoxy, propoxy, isopropoxy or butoxy, preferably methoxy. The lower alkoxyl group of the lower alkoxyl-substituted lower alkyl group may be the same a the above mentioned lower alkoxyl group, and the lower alkyl group thereof may be methyl, ethyl, propyl, isopropyl or butyl. A preferred lower alkoxyl-substituted lower alkyl group is 2-methoxyethyl. The cyclo-lower alkyl group of the cyclo-lower alkyl-substituted lower alkyl group may be a $C_3$–$C_5$ cycloalkyl group, and the lower alkyl group thereof may be the same as mentioned above, preferably methyl. As the lower alkenyl group, there may be mentioned allyl, 2-butenyl, 3-butenyl, 1-methyl-2-propenyl, 2-methyl-2-propenyl, 1,2-dimethyl-2-propenyl, 2-methyl-2-butenyl, 3-methyl-2-butenyl and 2,3-dimethyl-2-butenyl. As the lower alkynyl group, there may be mentioned 2-propynyl, 2-butynyl, 3-butynyl, 1-methyl-2-propynyl and 1,1-dimethyl-2-propynyl. As the lower haloalkyl group, there may be mentioned chloromethyl, 2-chloroethyl, 2-bromoethyl, 2,2,2-trifluoroethyl, and 2,2,3,3-tetrafluoropropyl. As the lower haloalkenyl group, there may be mentioned 2-chloro-2-propenyl, 2-bromo-2-propenyl, 1-chloromethyl-2-propenyl and 3-chloro-2-butenyl. The $C_3$–$C_9$ non-aromatic cyclic hydrocarbon group may be monocyclo or bicyclo, and may further be branched or contain a double bond. More specifically, there may be mentioned cyclopropyl, cyclobutyl, cyclopentyl, 1-methylcyclopentyl, 2-methylcyclopentyl, 3-methylcyclopentyl, 2-cyclopentenyl, cyclohexyl, 1-methylcyclohexyl, 2-methylcyclohexyl, 3-methylcyclohexyl, 4-methylcyclohexyl, 2-cyclohexenyl, 3-cyclohexenyl, cycloheptyl, cyclooctyl, 1-norbornyl and 2-norbornyl. As the $C_1$–$C_6$ alkyl group, the lower alkenyl group, and the lower alkynyl group for $R_2$, the above-mentioned specific examples for $R_1$ may likewise be mentioned. As examples wherein $R_1$ and $R_2$ form, together with the nitrogen atom to which they are bonded, a 3-8 member ring (which may be a bicyclo ring) which may contain a double bond or an oxygen atom within the ring and may have a branch, there may be mentioned:

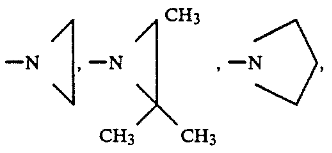

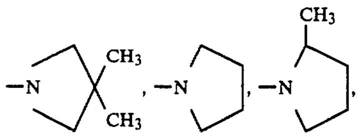

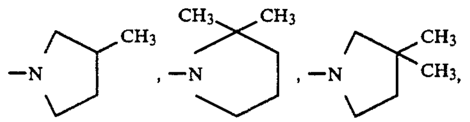

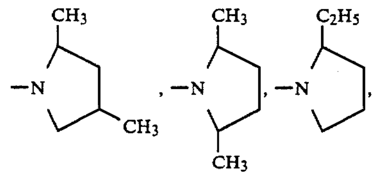

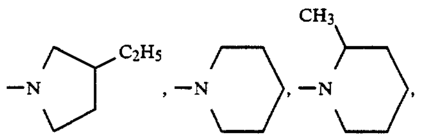

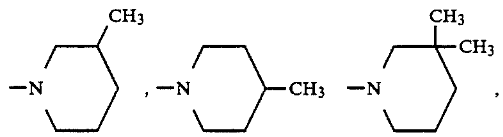

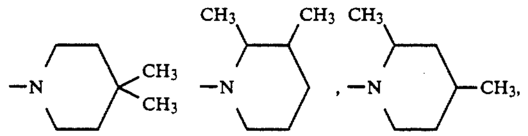

-continued

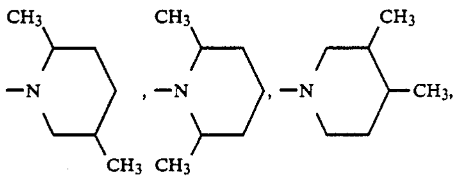

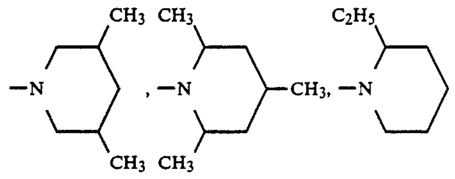

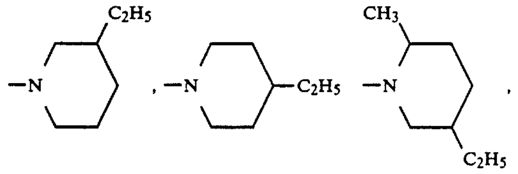

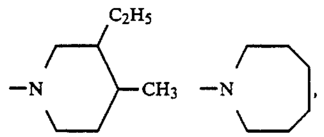

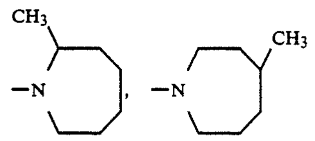

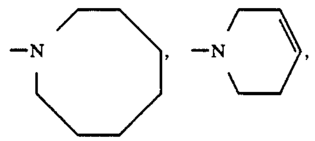

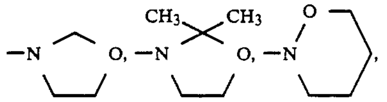

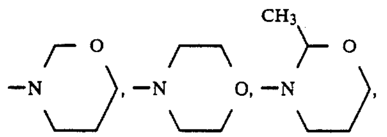

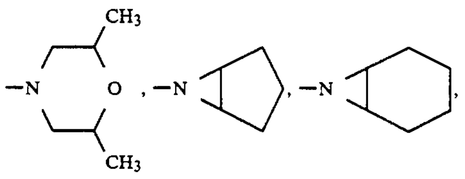

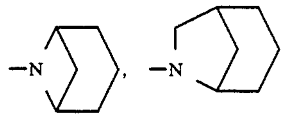

-continued

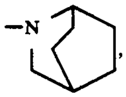, 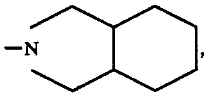,

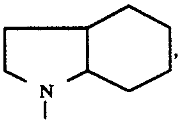, 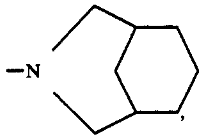,

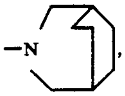, or 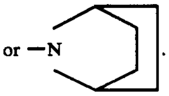.

Further, as the aryl moiety in the formula I, there may be mentioned 3-chlorophenyl, 2,3-dichlorophenyl, 3,5-dichlorophenyl, 2,5-dochlorophenyl, 2,3,5-trichlorophenyl, 2,3,6-trichlorophenyl, 2,3,5,6-tetrachlorophenyl, 3-trifluoromethylphenyl, 3,5-di(trifluoromethyl)phenyl, 2,3-di(trifluoromethyl)phenyl, 2,5-di(trifluoromethyl)phenyl, 2-chloro-3-trifluoromethylphenyl, 3-chloro-2-trifluoromethylphenyl, 2-chloro-5-trifluoromethylphenyl, 5-chloro-2-trifluoromethylphenyl and 3-chloro-5-trifluoromethylphenyl.

The substance of the present invention may be in a free state or in the form of a salt, e.g., in the form of an acid addition salt. Such a salt can likewise be employed as a herbicide. As the acid constituting the acid addition salt, there may be mentioned a mineral acid such as hydrochloric acid, sulfuric acid or phosphoric acid, or an organic acid such as acetic acid, chloroacetic acid, dichloroacetic acid, trichloroacetic acid, maleic acid or citric acid.

Among the substituted phenoxy ureas of the present invention, preferred specific examples are listed in Table 3.

TABLE 3

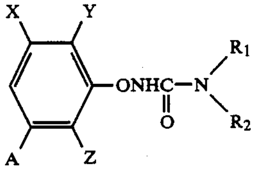

| Comp. No. | A | X | Y | Z | $R_1$ | $R_2$ |
|---|---|---|---|---|---|---|
| 260 | Cl | H | Cl | H | $CH_3$ | $CH_3$ |
| 261 | Cl | H | Cl | H | $-CH_2CH=CH_2$ | H |
| 262 | Cl | H | H | Cl | 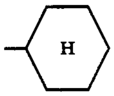 | H |
| 263 | Cl | H | H | H | $CH_3$ | $CH_3$ |
| 264 | Cl | H | H | Cl | $CH_3$ | $CH_3$ |
| 265 | Cl | Cl | H | H | $CH_3$ | $CH_3$ |
| 266 | Cl | Cl | H | Cl | $CH_3$ | $CH_3$ |
| 267 | $CF_3$ | H | H | H | $CH_3$ | $CH_3$ |
| 268 | Cl | H | H | H | $-CH_2C\equiv CH$ | $CH_3$ |
| 269 | Cl | H | H | H | n-$C_4H_9$ | $CH_3$ |
| 270 | Cl | H | H | H | $C_2H_5$ | $C_2H_5$ |
| 271 | Cl | H | H | H | n-$C_3H_7$ | $C_2H_5$ |
| 272 | Cl | H | H | H | $-CH_2CH=CH_2$ | $-CH_2CH=CH_2$ |
| 273 | Cl | H | H | H | 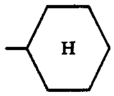 | $CH_3$ |
| 274 | Cl | H | H | H | 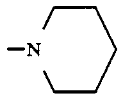 | |
| 275 | Cl | H | H | H | 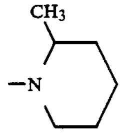 | |
| 276 | Cl | H | H | H | 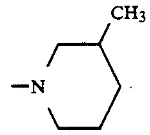 | |

TABLE 3-continued
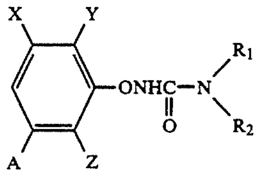
| Comp. No. | A | X | Y | Z | $R_1$ | $R_2$ |
|---|---|---|---|---|---|---|
| 277 | Cl | H | H | H | 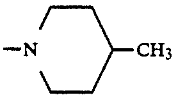 | |
| 278 | Cl | H | H | H | 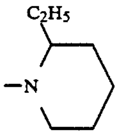 | |
| 279 | Cl | H | H | H | 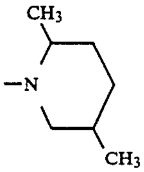 | |
| 280 | Cl | H | H | H | 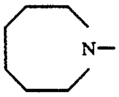 | |
| 281 | Cl | H | H | H | 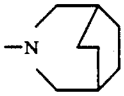 | |
| 282 | Cl | H | H | Cl | n-$C_3H_7$ | H |
| 283 | Cl | H | H | Cl | 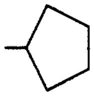 | H |
| 284 | Cl | H | H | Cl | 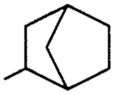 | H |
| 285 | Cl | H | H | Cl | $C_2H_5$ | $C_2H_5$ |
| 286 | Cl | H | H | Cl | n-$C_3H_7$ | n-$C_3H_7$ |
| 287 | Cl | H | H | Cl | 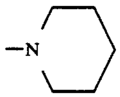 | |
| 288 | Cl | H | H | Cl | 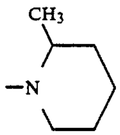 | |
| 289 | Cl | H | H | Cl | 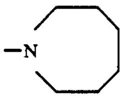 | |
| 290 | Cl | H | Cl | H | $C_2H_5$ | H |
| 291 | Cl | H | Cl | H | $-CH_2CH_2Cl$ | H |

TABLE 3-continued
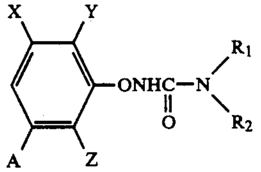
| Comp. No. | A | X | Y | Z | $R_1$ | $R_2$ |
|---|---|---|---|---|---|---|
| 292 | Cl | H | Cl | H | n-$C_3H_7$ | H |
| 293 | Cl | H | Cl | H | i-$C_3H_7$ | H |
| 294 | Cl | H | Cl | H | 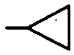 | H |
| 295 | Cl | H | Cl | H | $-CH_2C{\equiv}CH$ | H |
| 296 | Cl | H | Cl | H | 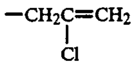 | H |
| 297 | Cl | H | Cl | H | n-$C_4H_9$ | H |
| 298 | Cl | H | Cl | H | s-$C_4H_9$ | H |
| 299 | Cl | H | Cl | H | i-$C_4H_9$ | H |
| 300 | Cl | H | Cl | H | t-$C_4H_9$ | H |
| 301 | Cl | H | Cl | H | 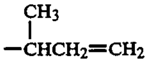 | H |
| 302 | Cl | H | Cl | H | 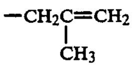 | H |
| 303 | Cl | H | Cl | H | 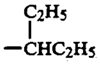 | H |
| 304 | Cl | H | Cl | H | 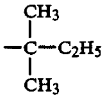 | H |
| 305 | Cl | H | Cl | H | 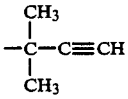 | H |
| 306 | Cl | H | Cl | H | 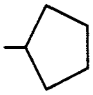 | H |
| 307 | Cl | H | Cl | H | 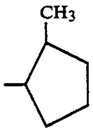 | H |
| 308 | Cl | H | Cl | H | 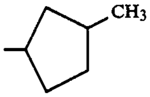 | H |
| 309 | Cl | H | Cl | H | 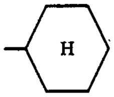 | H |
| 310 | Cl | H | Cl | H | 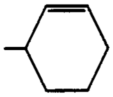 | H |

TABLE 3-continued

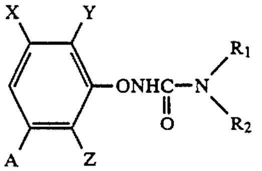

| Comp. No. | A | X | Y | Z | $R_1$ | $R_2$ |
|---|---|---|---|---|---|---|
| 311 | Cl | H | Cl | H | 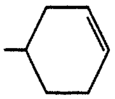 | H |
| 312 | Cl | H | Cl | H | 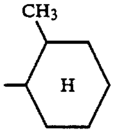 | H |
| 313 | Cl | H | Cl | H | 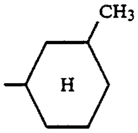 | H |
| 314 | Cl | H | Cl | H | 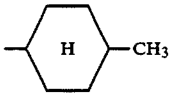 | H |
| 315 | Cl | H | Cl | H | 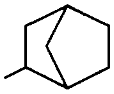 | H |
| 316 | Cl | H | Cl | H | 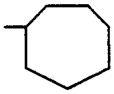 | H |
| 317 | Cl | H | Cl | H | 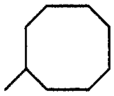 | H |
| 318 | Cl | H | Cl | H | $C_2H_5$ | $CH_3$ |
| 319 | Cl | H | Cl | H | $C_2H_5$ | $C_2H_5$ |
| 320 | Cl | H | Cl | H | $n\text{-}C_3H_7$ | $CH_3$ |
| 321 | Cl | H | Cl | H | $i\text{-}C_3H_7$ | $CH_3$ |
| 322 | Cl | H | Cl | H | $-CH_2CH=CH_2$ | $CH_3$ |
| 323 | Cl | H | Cl | H | $-CH_2C\equiv CH$ | $CH_3$ |
| 324 | Cl | H | Cl | H | $-CH_2C=CH_2$<br>\|<br>Cl | $CH_3$ |
| 325 | Cl | H | Cl | H | $n\text{-}C_4H_9$ | $CH_3$ |
| 326 | Cl | H | Cl | H | $s\text{-}C_4H_9$ | $CH_3$ |
| 327 | Cl | H | Cl | H | $i\text{-}C_4H_9$ | $CH_3$ |
| 328 | Cl | H | Cl | H | $CH_3$<br>\|<br>$-CHCH=CH_2$ | $CH_3$ |
| 329 | Cl | H | Cl | H | $CH_3$<br>\|<br>$-CHC\equiv CH$ | $CH_3$ |
| 330 | Cl | H | Cl | H | $-CH_2C=CH_2$<br>\|<br>$CH_3$ | $CH_3$ |

TABLE 3-continued
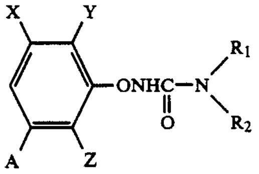
| Comp. No. | A | X | Y | Z | $R_1$ | $R_2$ |
|---|---|---|---|---|---|---|
| 331 | Cl | H | Cl | H | 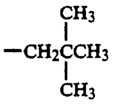 | $CH_3$ |
| 332 | Cl | H | Cl | H | 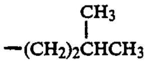 | $CH_3$ |
| 333 | Cl | H | Cl | H | 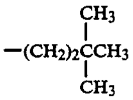 | $CH_3$ |
| 334 | Cl | H | Cl | H | 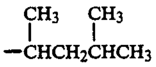 | $CH_3$ |
| 335 | Cl | H | Cl | H | n-$C_3H_7$ | $C_2H_5$ |
| 336 | Cl | H | Cl | H | i-$C_3H_7$ | $C_2H_5$ |
| 337 | Cl | H | Cl | H | n-$C_4H_9$ | $C_2H_5$ |
| 338 | Cl | H | Cl | H | n-$C_3H_7$ | n-$C_3H_7$ |
| 339 | Cl | H | Cl | H | $-CH_2CH{=}CH_2$ | $-CH_2CH{=}CH_2$ |
| 340 | Cl | H | Cl | H | $-CH_2C{\equiv}CH$ | $-CH_2C{\equiv}CH$ |
| 341 | Cl | H | Cl | H | 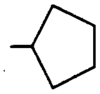 | $CH_3$ |
| 342 | Cl | H | Cl | H | 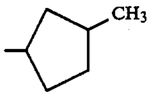 | $CH_3$ |
| 343 | Cl | H | Cl | H | 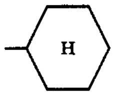 | $CH_3$ |
| 344 | Cl | H | Cl | H | 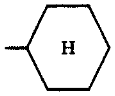 | $C_2H_5$ |
| 345 | Cl | H | Cl | H | 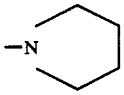 | |
| 346 | Cl | H | Cl | H | 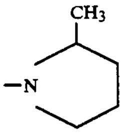 | |
| 347 | Cl | H | Cl | H | 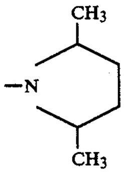 | |

TABLE 3-continued
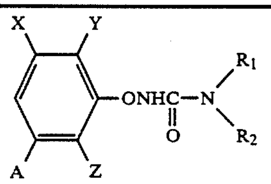
| Comp. No. | A | X | Y | Z | $R_1$ | $R_2$ |
|---|---|---|---|---|---|---|
| 348 | Cl | H | Cl | H | 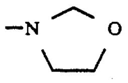 | |
| 349 | Cl | H | Cl | H | 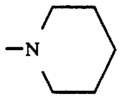 | |
| 350 | Cl | H | Cl | H | 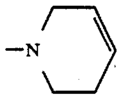 | |
| 351 | Cl | H | Cl | H | 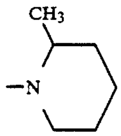 | |
| 352 | Cl | H | Cl | H | 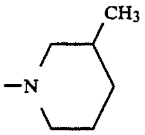 | |
| 353 | Cl | H | Cl | H | 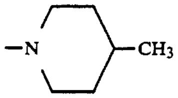 | |
| 354 | Cl | H | Cl | H | 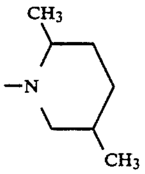 | |
| 355 | Cl | H | Cl | H | 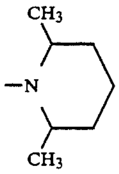 | |
| 356 | Cl | H | Cl | H | 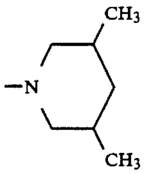 | |
| 357 | Cl | H | Cl | H | 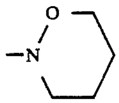 | |

TABLE 3-continued
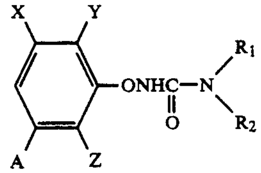
| Comp. No. | A | X | Y | Z | $R_1$ | $R_2$ |
|---|---|---|---|---|---|---|
| 358 | Cl | H | Cl | H | 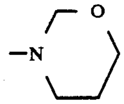 | |
| 359 | Cl | H | Cl | H | 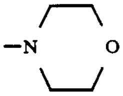 | |
| 360 | Cl | H | Cl | H | 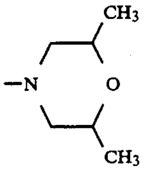 | |
| 361 | Cl | H | Cl | H | 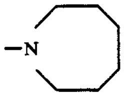 | |
| 362 | Cl | H | Cl | H | 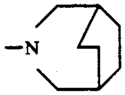 | |
| 363 | Cl | H | Cl | H | 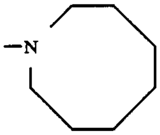 | |
| 364 | Cl | H | Cl | H | 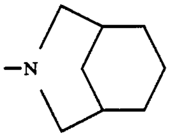 | |
| 365 | Cl | H | Cl | H | 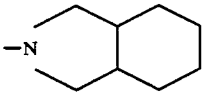 | |
| 366 | Cl | Cl | H | H | i-$C_3H_7$ | H |
| 367 | Cl | Cl | H | H | t-$C_4H_9$ | H |
| 368 | Cl | Cl | H | H | 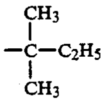 | H |
| 369 | Cl | Cl | H | H | 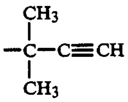 | H |

TABLE 3-continued

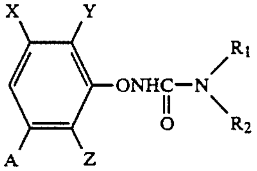

| Comp. No. | A | X | Y | Z | $R_1$ | $R_2$ |
|---|---|---|---|---|---|---|
| 370 | Cl | Cl | H | H | 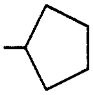 | H |
| 371 | Cl | Cl | H | H | 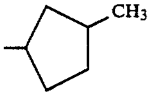 | H |
| 372 | Cl | Cl | H | H | n-$C_3H_7$ | $CH_3$ |
| 373 | Cl | Cl | H | H | i-$C_3H_7$ | $CH_3$ |
| 374 | Cl | Cl | H | H | $-CH_2CH{=}CH_2$ | $CH_3$ |
| 375 | Cl | Cl | H | H | $-CH_2C{\equiv}CH$ | $CH_3$ |
| 376 | Cl | Cl | H | H | $-CH_2CF_2CF_2H$ | $CH_3$ |
| 377 | Cl | Cl | H | H | $-CH_2C{=}CH_2$<br>Cl | $CH_3$ |
| 378 | Cl | Cl | H | H | n-$C_4H_9$ | $CH_3$ |
| 379 | Cl | Cl | H | H | s-$C_4H_9$ | $CH_3$ |
| 380 | Cl | Cl | H | H | i-$C_4H_9$ | $CH_3$ |
| 381 | Cl | Cl | H | H | $CH_3$<br>$-CHCH{=}CH_2$ | $CH_3$ |
| 382 | Cl | Cl | H | H | $-CH_2C{=}CH_2$<br>$CH_3$ | $CH_3$ |
| 383 | Cl | Cl | H | H | $CH_3$<br>$-CHC{\equiv}CH$ | $CH_3$ |
| 384 | Cl | Cl | H | H | $CH_3$<br>$-CH_2C{=}CH_3$<br>$CH_3$ | $CH_3$ |
| 385 | Cl | Cl | H | H | $CH_3$<br>$-(CH_2)_2CHCH_3$ | $CH_3$ |
| 386 | Cl | Cl | H | H | $CH_3$<br>$-(CH_2)_2CCH_3$<br>$CH_3$ | $CH_3$ |
| 387 | Cl | Cl | H | H | $C_2H_5$ | $C_2H_5$ |
| 388 | Cl | Cl | H | H | n-$C_3H_7$ | $C_2H_5$ |
| 389 | Cl | Cl | H | H | i-$C_3H_7$ | $C_2H_5$ |
| 390 | Cl | Cl | H | H | n-$C_3H_7$ | n-$C_3H_7$ |
| 391 | Cl | Cl | H | H | $-CH_2CH{=}CH_2$ | $-CH_2CH{=}CH_2$ |
| 392 | Cl | Cl | H | H | $-CH_2C{\equiv}CH$ | $-CH_2C{\equiv}CH$ |
| 393 | Cl | Cl | H | H | 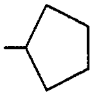 | $CH_3$ |
| 394 | Cl | Cl | H | H | 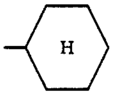 | $CH_3$ |

TABLE 3-continued
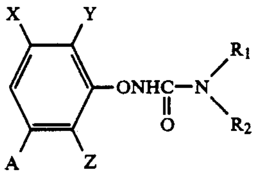
| Comp. No. | A | X | Y | Z | R1 | R2 |
|---|---|---|---|---|---|---|
| 395 | Cl | Cl | H | H | 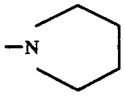 | |
| 396 | Cl | Cl | H | H | 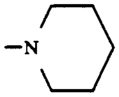 | |
| 397 | Cl | Cl | H | H | 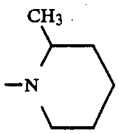 | |
| 398 | Cl | Cl | H | H | 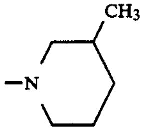 | |
| 399 | Cl | Cl | H | H | 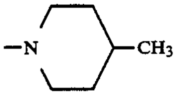 | |
| 400 | Cl | Cl | H | H | 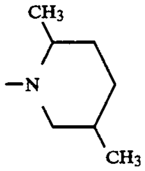 | |
| 401 | Cl | Cl | H | H | 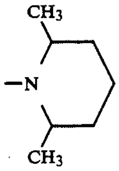 | |
| 402 | Cl | Cl | H | H | 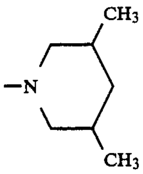 | |
| 403 | Cl | Cl | H | H | 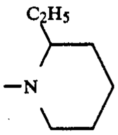 | |
| 404 | Cl | Cl | H | H | 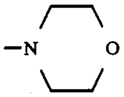 | |

TABLE 3-continued

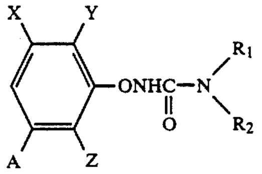

| Comp. No. | A | X | Y | Z | $R_1$ | $R_2$ |
|---|---|---|---|---|---|---|
| 405 | Cl | Cl | H | H | 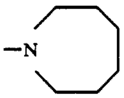 | |
| 406 | Cl | Cl | H | H | 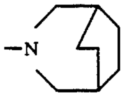 | |
| 407 | Cl | Cl | H | H | 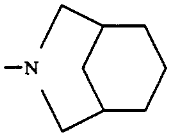 | |
| 408 | Cl | Cl | H | H | 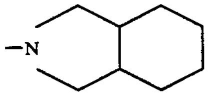 | |
| 409 | $CF_3$ | H | H | H | 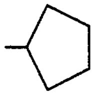 | H |
| 410 | $CF_3$ | H | H | H | $i\text{-}C_3H_7$ | $CH_3$ |
| 411 | $CF_3$ | H | H | H | $-CH_2CH{=}CH_2$ | $CH_3$ |
| 412 | $CF_3$ | H | H | H | $-CH_2C{\equiv}CH$ | $CH_3$ |
| 413 | $CF_3$ | H | H | H | $-CH_2CF_2CF_2H$ | $CH_3$ |
| 414 | $CF_3$ | H | H | H | $-CH_2C(Cl){=}CH_2$ | $CH_3$ |
| 415 | $CF_3$ | H | H | H | $n\text{-}C_4H_9$ | $CH_3$ |
| 416 | $CF_3$ | H | H | H | $s\text{-}C_4H_9$ | $CH_3$ |
| 417 | $CF_3$ | H | H | H | $i\text{-}C_4H_9$ | $CH_3$ |
| 418 | $CF_3$ | H | H | H | $-CH(CH_3)CH{=}CH_2$ | $CH_3$ |
| 419 | $CF_3$ | H | H | H | $-CH_2C(CH_3){=}CH_2$ | $CH_3$ |
| 420 | $CF_3$ | H | H | H | $-CH(CH_3)C{\equiv}CH$ | $CH_3$ |
| 421 | $CF_3$ | H | H | H | $-CH_2C(CH_3)_2-CH_3$ | $CH_3$ |
| 422 | $CF_3$ | H | H | H | $-(CH_2)_2CH(CH_3)CH_3$ | $CH_3$ |

TABLE 3-continued
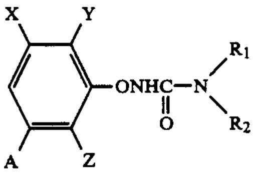
| Comp. No. | A | X | Y | Z | $R_1$ | $R_2$ |
|---|---|---|---|---|---|---|
| 423 | $CF_3$ | H | H | H | 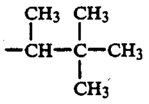 | $CH_3$ |
| 424 | $CF_3$ | H | H | H | 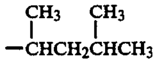 | $CH_3$ |
| 425 | $CF_3$ | H | H | H | 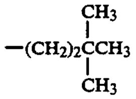 | $CH_3$ |
| 426 | $CF_3$ | H | H | H | $C_2H_5$ | $C_2H_5$ |
| 427 | $CF_3$ | H | H | H | n-$C_3H_7$ | $C_2H_5$ |
| 428 | $CF_3$ | H | H | H | 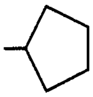 | $CH_3$ |
| 429 | $CF_3$ | H | H | H | 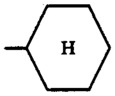 | $CH_3$ |
| 430 | $CF_3$ | H | H | H | 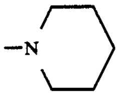 | |
| 431 | $CF_3$ | H | H | H | 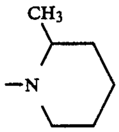 | |
| 432 | $CF_3$ | H | H | H | 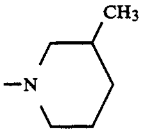 | |
| 433 | $CF_3$ | H | H | H | 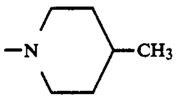 | |
| 434 | $CF_3$ | H | H | H | 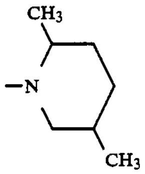 | |

TABLE 3-continued
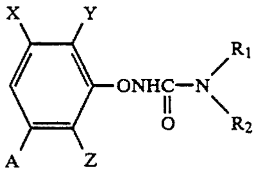
| Comp. No. | A | X | Y | Z | $R_1$ | $R_2$ |
|---|---|---|---|---|---|---|
| 435 | $CF_3$ | H | H | H | 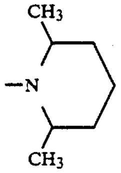 | |
| 436 | $CF_3$ | H | H | H | 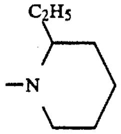 | |
| 437 | $CF_3$ | H | H | H | 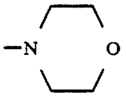 | |
| 438 | $CF_3$ | H | H | H | 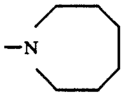 | |
| 439 | $CF_3$ | H | H | H | 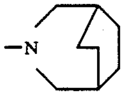 | |
| 440 | $CF_3$ | H | H | H | 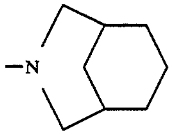 | |
| 441 | $CF_3$ | H | $CF_3$ | H | 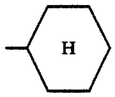 | H |
| 442 | $CF_3$ | $CF_3$ | H | H | 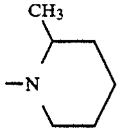 | |
443
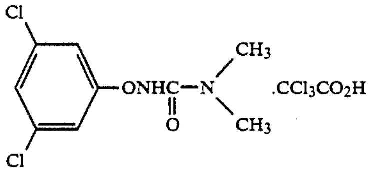 $.CCl_3CO_2H$ TABLE 3-continued
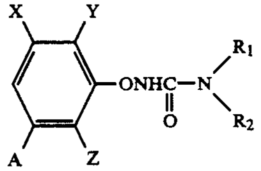
| Comp. No. | A | X | Y | Z | $R_1$ | $R_2$ |
|---|---|---|---|---|---|---|
| 444 | 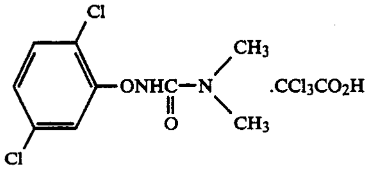 $.CCl_3CO_2H$ | | | | | |
| 445 | 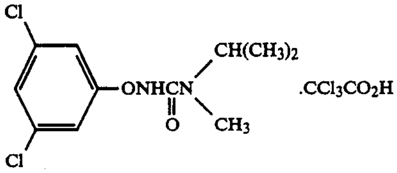 $.CCl_3CO_2H$ | | | | | |
| 446 | Cl | H | Cl | H | $-CH_2CH{=}CHCH_3$ | $CH_3$ |
| 447 | Cl | H | Cl | H | $-CH(CH_3)-(CH_2)_2CH_3$ | $CH_3$ |
| 448 | Cl | H | Cl | H | $-CH(CH_3)CH(CH_3)_2$ | $CH_3$ |
| 449 | Cl | H | Cl | H | $-CH_2CH(CH_3)C_2H_5$ | $CH_3$ |
| 450 | Cl | H | Cl | H | $-CH(C_2H_5)_2$ | $CH_3$ |
| 451 | Cl | H | Cl | H | $-CH(CH_3)C(CH_3)_3$ | $CH_3$ |
| 452 | Cl | H | Cl | H | 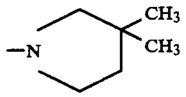 | |
| 453 | Cl | H | Cl | H | 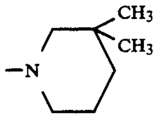 | |
| 454 | Cl | H | Cl | H | 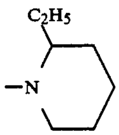 | |
| 455 | Cl | H | Cl | H | 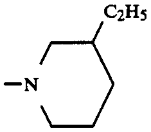 | |
| 456 | Cl | H | Cl | H | 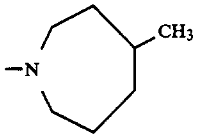 | |

TABLE 3-continued
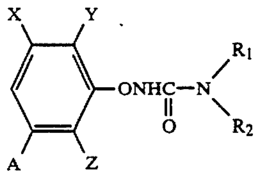
| Comp. No. | A | X | Y | Z | $R_1$ | $R_2$ |
|---|---|---|---|---|---|---|
| 457 | Cl | H | Cl | H | 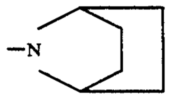 | |
| 458 | Cl | Cl | H | H | $-CH_2CH{=}CHCH_3$ | $CH_3$ |
| 459 | Cl | Cl | H | H | $CH_3$<br>$-CH(CH_2)_2CH_3$ | $CH_3$ |
| 460 | Cl | Cl | H | H | $CH_3$<br>$-CH_2CHC_2H_5$ | $CH_3$ |
| 461 | Cl | Cl | H | H | $CH_3$<br>$-CHCH(CH_3)_2$ | $CH_3$ |
| 462 | Cl | Cl | H | H | $-CH(C_2H_5)_2$ | $CH_3$ |
| 463 | Cl | Cl | H | H | $CH_3$ $CH_3$<br>$-CHCH_2CHCH_3$ | $CH_3$ |
| 464 | Cl | Cl | H | H | $-(CH_2)_2C(CH_3)_3$ | $CH_3$ |
| 465 | Cl | Cl | H | H | 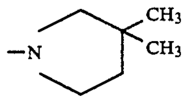 | |
| 466 | Cl | Cl | H | H | 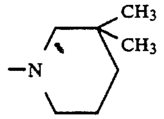 | |
| 467 | Cl | Cl | H | H | 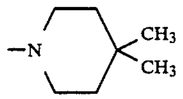 | |
| 468 | Cl | Cl | H | H | 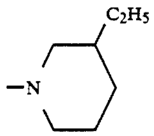 | |
| 469 | Cl | Cl | H | H | 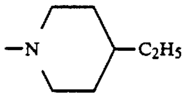 | |
| 470 | Cl | Cl | H | H | 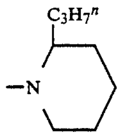 | |

TABLE 3-continued
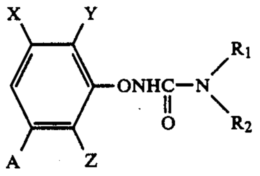
| Comp. No. | A | X | Y | Z | R1 | R2 |
|---|---|---|---|---|---|---|
| 471 | Cl | Cl | H | H | 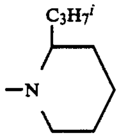 | |
| 472 | Cl | Cl | H | H | 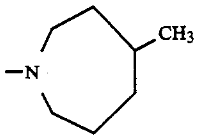 | |
| 473 | Cl | Cl | H | H | 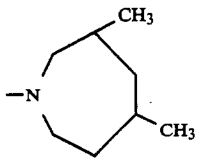 | |
| 474 | Cl | Cl | H | H | 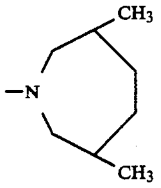 | |
| 475 | Cl | Cl | H | H | 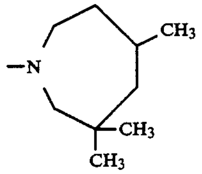 | |
| 476 | Cl | Cl | H | H | 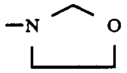 | |
| 477 | Cl | Cl | H | H | 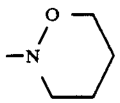 | |
| 478 | Cl | Cl | H | H | 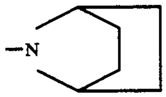 | |
| 479 | Cl | Cl | H | H | 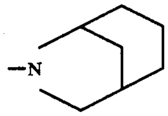 | |

TABLE 3-continued
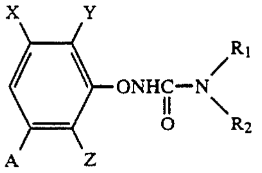
| Comp. No. | A | X | Y | Z | $R_1$ | $R_2$ |
|---|---|---|---|---|---|---|
| 480 | Cl | Cl | H | H | 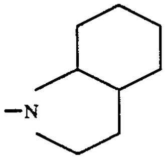 | |
| 481 | Cl | Cl | H | H | 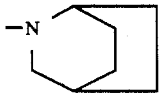 | |
| 482 | Cl | Cl | H | H | 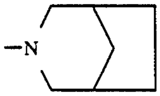 | |
| 483 | Cl | Cl | H | H | 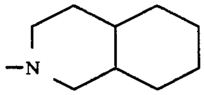 | |
| 484 | $CF_3$ | H | H | H | $-CH_2CH{=}CHCH_3$ | $CH_3$ |
| 485 | $CF_3$ | H | H | H | $CH_3$<br>$-CH-(CH_2)_2CH_3$ | $CH_3$ |
| 486 | $CF_3$ | H | H | H | $CH_3$<br>$-CHCH(CH_3)_2$ | $CH_3$ |
| 487 | $CF_3$ | H | H | H | $CH_3$<br>$-CH_2CHC_2H_5$ | $CH_3$ |
| 488 | $CF_3$ | H | H | H | $-CH(C_2H_5)_2$ | $CH_3$ |
| 489 | $CF_3$ | H | H | H | 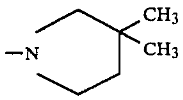 | |
| 490 | $CF_3$ | H | H | H | 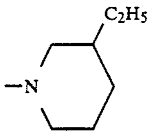 | |
| 491 | $CF_3$ | H | H | H | 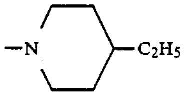 | |
| 492 | $CF_3$ | H | H | H | 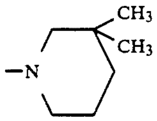 | |

TABLE 3-continued
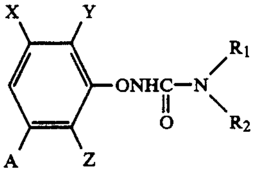
| Comp. No. | A | X | Y | Z | $R_1$ | $R_2$ |
|---|---|---|---|---|---|---|
| 493 | $CF_3$ | H | H | H | 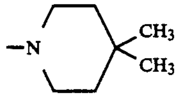 | |
| 494 | $CF_3$ | H | H | H | 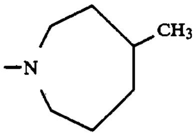 | |
| 495 | $CF_3$ | H | H | H | 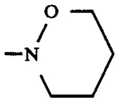 | |
| 496 | $CF_3$ | H | H | H | 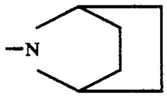 | |
| 497 | $CF_3$ | H | H | H | 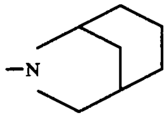 | |
| 498 | $CF_3$ | H | H | H | 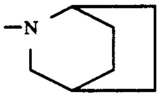 | |
| 499 | $CF_3$ | H | H | H | 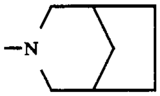 | |
| 500 | $CF_3$ | $CF_3$ | H | H | 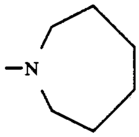 | |
| 501 | Cl | H | Cl | H | $-OCH_3$ | $CH_3$ |
| 502 | Cl | H | Cl | H | $-(CH_2)_2OCH_3$ | H |
| 503 | Cl | H | Cl | H | $-(CH_2)_2OCH_3$ | $CH_3$ |
| 504 | Cl | H | Cl | H | $-(CH_2)_2OCH_3$ | $C_2H_5$ |
| 505 | Cl | H | Cl | H | $-CH_2-$ 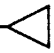 | $CH_3$ |
| 506 | Cl | Cl | H | H | $-(CH_2)_2OCH_3$ | $CH_3$ |
| 507 | Cl | Cl | H | H | $-(CH_2)_2OCH_3$ | $C_3H_7^n$ |
| 508 | Cl | Cl | H | H | $-CH_2-$ 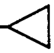 | $CH_3$ |
| 509 | $CF_3$ | H | H | H | $-(CH_2)_2OCH_3$ | $CH_3$ |

TABLE 3-continued

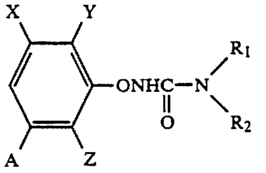

| Comp. No. | A | X | Y | Z | $R_1$ | $R_2$ |
|---|---|---|---|---|---|---|
| 510 | $CF_3$ | H | H | H | 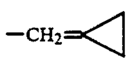 | $CH_3$ |
| 511 | F | H | F | H | 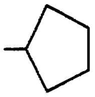 | H |
| 512 | F | H | F | H | 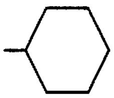 | H |

PROCESS 1

Among the substituted phenoxy ureas of the present invention, those wherein $R_2$ is other than a hydrogen atom, i.e. $R_2^1$, can be prepared from compounds having the formulas (XXI) and (XXII). As the phenoxyamines of the formula (XXI), there may be employed those having aryl moieties listed above with respect to the compounds of the formula (XX). Further, $R_1$ and $R_2^1$ of the formula (XXII) may be those listed above with respect to the compounds of the formula (XX).

As the base to be used in the reaction, there may be mentioned a pyridine base such as pyridine, picoline, lutidine or collidine; a tertiary amine such as triethylamine, 1,8-diazabicyclo[5.4.0]undecene-7 or N,N-dimethylaniline; or an inorganic base such as $NaHCO_3$, $KHCO_3$, $Na_2CO_3$ or $K_2CO_3$. Among them, pyridine is preferred. The base is used in an amount of from 0.5 to 20, preferably from 1 to 10 in the molar ratio relative to the carbamic acid chloride of the formula (XXII).

No solvent may be used for the reaction. However, it is possible to employ a solvent inert to the reaction, for instance, an aromatic hydrocarbon such as benzene, toluene or xylene; a halogenated hydrocarbon such as chloroform, dichloromethane, carbon tetrachloride, dichloroethane, trichloroethane, tetrachloroethane, chlorobenzene, dichlorobenzene, tetrahydrofuran, ethyl acetate, or dimethylformamide.

For the reaction, the carbamic acid chloride is used usually in an amount of from 0.8 to 3 moles, preferably from 1 to 2 moles, per mole of the phenoxyamine. The two reactants and the base are mixed without a solvent or in the above-mentioned solvent, and then stirred at a temperature of from 0° to 100° C., preferably from 0° to 60° C., for from 0.5 to 30 hours.

After the reaction, the desired product can be obtained in a conventional method as shown in the examples given hereinafter.

PROCESS 2

Among the substituted phenoxy ureas of the present invention, those wherein $R_2$ is a hydrogen atom, i.e., those represented by the formula (XX)-II, can be produced by reacting a phenoxyamine of the formula (XXI) with an isocyanate of the formula (XXIII). In this case, as specific compounds of the phenoxyamine of the formula (XXI), those used for Process 1 may be mentioned. Further, the specific examples of the alkyl group, etc. for $R_1$ of the formula (XXIII) may be the same.

For the reaction, in addition to a tertiary amine such as triethylamine, a Lewis acid such as $AlCl_3$ or $ZnCl_2$ may be used in an amount of from 0.1 to 10 mole % relative to the phenoxyamine of the formula (XXI) in a reaction solvent listed in Process 1, and the desired compound can be obtained in the same manner as in Process 1 except that an isocyanate of the formula (XXIII) is used in an amount of from 0.8 to 2 in a molar ratio relative to the phenoxyamine of the formula (XXI).

PROCESS 3

The substituted phenoxy ureas of the formula (XX)-II of the present invention can be produced also by reacting a phenoxycarbamate of the formula (XXIV) with an amine of the formula (XXV).

As the aryl moiety of the formula:

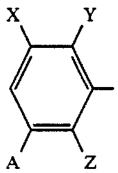

of the compound of the formula (XXIV), there may be mentioned those listed above as the aryl moiety in the formula (XX), and as Ar, there may be mentioned a phenyl group, a chlorophenyl group or a tolyl group. Further, the phenoxycarbamate of the formula (XXIV) can be produced from a phenoxyamine of the formula (XXI) and ArOCOCl by using a base and solvent as mentioned in Process 1.

As the alkyl group, etc. for $R_1$ of the amine of the formula (XXV), those listed above with respect to the formula (XX) may be mentioned.

The reaction can be conducted at a temperature of from 0° to 100° C., preferably from 0° to 80° C. for 0.5 to 5 hours by using from 0.8 to 5 moles of the amine of the formula (XXV) relative to one mole of the phenoxy carbamate of the formula (XXIV). In this case, the same solvents as mentioned as in Process 1 may be used.

The substituted aryloxyureas of formulas (X) and (XX) and their acid addition salts provided by this invention exhibit an excellent and characteristic herbicidal efficacy.

Accordingly, the present invention also provides a herbicide comprising the substituted aryloxyurea or its acid addition salt of the invention as a herbicidally effective ingredient.

As a herbicide, the compounds of this invention may be directly used, or as various formulations such as granules, wettable powders, emulsifiable concentrates, dusts and pulverulent agents. The compounds of this invention show better results when used in these formulations. Herbicides in the form of these formulations can be produced from the compounds of this invention and various adjuvants, for example solid carriers such as talc, bentonite, clay, kaolin, diatomaceous earth, white carbon, vermiculite, slaked lime, silica sand, ammonium sulfate and urea, liquid carriers such as alcohols, dioxane, acetone, cyclohexanone, methylnaphthalene, dimethylformamide and dimethyl sulfoxide, emulsifiers and dispersants such as salts of alkylsulfuric esters, alkylarylsulfonate salts, polyoxyethylene glycol ethers, polyoxyethylene alkylaryl ethers and polyoxyethylene sorbitan monoalkylates, and carboxymethyl cellulose and gum arabic. As required, the proportion of the active ingredient may be adjusted. For preparation of a dust, it is suitably 0.5 to 20% by weight, and for an emulsifiable concentrate or a wettable powder, it is suitably 5 to 70% by weight.

The herbicide of this invention may be applied as such or in a form suitably diluted or suspended in water, etc. in an amount effective for controlling weeds. The amount of the compound of this invention used as a herbicide cannot be generalized because it varies depending upon the soil conditions, the formulation, preparation, the time of application, the method of application, the types of the crops or weeds to be controlled, etc. It is effective to apply it in an amount of 10 g to 5 kg per hectare.

The herbicide of this invention exhibits a better herbicidal efficacy than commercial herbicides by application to annual weeds such as barnyardgrass (*Echinochloa crus-galli*), umbrella plant (*Cyperus difformis*), monochoria (*Monochoria vaginalis*), "kikashigusa" (*Rotala indica*), false pimpernel (*Lindernia pyxidaria*) and "abunome" (*Dopatrium junceum*) and perennial weeds such as bulrush (*Scirous uncoides*), spikerush (*Eleocharis acicularis*), "mizugayatsuri" (*Cyperus serotinus*) and narrowleaf waterplaintain (*Alisma canaliculatum*), which occur in paddies, during their germination and growth. On the other hand, the herbicide of this invention is not phytotoxic to useful crops, particularly rice, even at high dosages, and has very high selectivity. Furthermore, by soil treatment or foliar treatment, the herbicide of this invention shows a high herbicidal efficacy against various weeds causing hazards in upland farms, for example gramineous weeds such as barnyardgrass, crabgrass (*Digitaria sanquinals*), green foxtail (*Setaria viridis*), annual bluegrass (*Poa annua*) and water foxtail (*Alopecurus geniculatus*), cyperous weeds such as rice flatsedge (*Cyperus iria*) and broadleaved weeds such as redroot pigweed (*Amaranthus retroflexus*) and lambsquarters (*Chenopodium album*), and yet show high safety on principal crops such as rice, wheat, corn, soybeans and cotton. The herbicide of this invention can also be used to control weeds in orchards, pasture land, lawns and non-agricultural lands.

If required, the herbicide of this invention may be used in combination with other agricultural chemicals and feeds, for example.

EXAMPLES

EXAMPLE 1A 1,1-Hexamethylene-3-(3-nitrophenoxy)urea (Compound No. 1)

3-Nitrophenoxyamine (3.02 g; 19.6 mmoles) was dissolved in 7.9 ml of pyridine, and 4.75 g (29.4 mmoles) of N,N-hexamethylenecarbamoyl chloride was added. The mixture was stirred at 25° C. for 10 hours and then at 35° to 40° C. for 6.5 hours. A saturated aqueous solution of sodium chloride (150 ml) was added to the reaction mixture, and the mixture was extracted with ethyl acetate. The extract was dried over anhydrous magnesium sulfate, and ethyl acetate was evaporated under reduced pressure. Recrystallization of the residue from toluene/hexane gave 3.92 g (yield 72%) of the captioned compound as yellow crystals.

Melting point: 97°-99° C.

Mass spectrum (FD method): m/z 279 (molecular ion peak)

IR spectrum (KBr tablet, $cm^{-1}$): 3130, 1643, 530, 1474, 1347, 736

$^1$H-NMR spectrum ($CDCl_3$ solution, ppm)

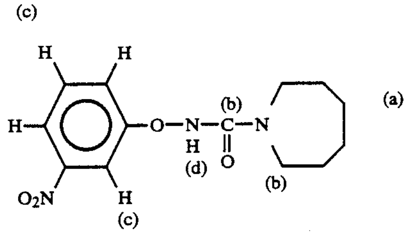

(a) 1.5-2.0 (8H, m)
(b) 3.44 (4H, m)
(c) 7.2-7.9 (4H, m)
(d) 7.96 (1H, s)

EXAMPLE 2A

1-Cyclopentyl-3-(5-methyl-2-nitrophenoxy)urea (Compound No. 2)

Phenyl N-(5-methyl-2-nitrophenoxy)carbamate (3.86 g; 13.4 mmoles) was dissolved in 60 ml of ethyl acetate, and 2.85 g (33.5 mmoles) of cyclopentylamine was added. The mixture was stirred at 60° C. for 1.5 hours. The reaction mixture was cooled to room temperature, washed with a 3% aqueous solution of sodium hydroxide and then with a saturated sodium chloride solution, and dried over anhydrous magnesium sulfate. Ethyl acetate was evaporated under reduced pressure, and the residue was recrystallized from toluene/hexane to give 1.83 g (yield 49%) of the captioned compound as yellow crystals.

(Melting point: 131°-132° C. (decomp.)

Mass spectrum (FD method): m/z 279 (molecular ion peak)

IR spectrum (KBr tablet, $cm^{-1}$): 3390, 1660, 1605, 1590, 1340, 1310, 1260, 1240

$^1$H-NMR spectrum ($CDCl_3$ solution, ppm)

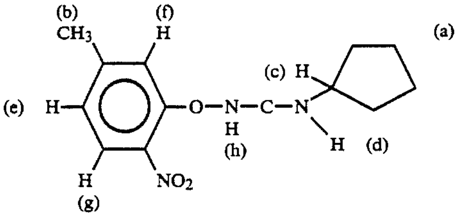

(a) 1.4–2.2 (8H, m)
(b) 2.44 (3H, s)
(c) 4.16 (1H, m)
(d) 6.74 (1H, d, J=7.2 Hz)
(e) 6.98 (1H, d, J=8.3, 1.3 Hz)
(f) 7.48 (1H, d, J=1.3 Hz)
(h) 8.7 (1H, br,s)

EXAMPLE 3A 3-(3-Cyanophenoxy)-1,1-hexamethyleneurea (compound No. 3)

Phenyl N-(3-cyanophenoxy)carbamate (2.10 g: 8.3 mmoles) was dissolved in a mixed solvent of 20 ml of N,N-dimethylformamide and 20 ml of toluene. Then, 1.64 g (16.5 mmoles) of hexamethylenimine was added. The mixture was stirred at 60° C. for 1 hour. The reaction mixture was cooled to room temperature, and after adding 120 ml of water, extracted with ethyl acetate. The extract was washed with a saturated aqueous sodium chloride solution, and dried over anhydrous magnesium sulfate. Ethyl acetate was evaporated under reduced pressure. The residue was purified by silica gel column chromatography (eluting solvent: ethyl acetate/hexane). Recrystallization from toluene/hexane gave 2.05 g (yield 91%) of the captioned compound as pale yellow crystals.

Melting point 77°-79° C.

Mass spectrum (FD method): m/z 259 (molecular ion peak)

IR spectrum (KBr tablet, $cm^{-1}$): 3285, 2230, 1656, 1575, 1482, 1405, 1241, 1205, 800, 684

$^1$H-NMR spectrum ($CDCl_3$ solution, ppm)

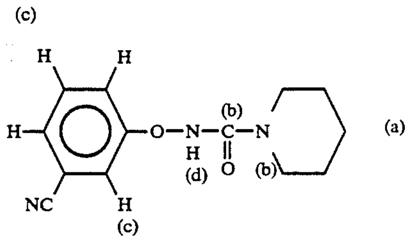

(a) 1.4–2.0 (8H, m)
(b) 3.40 (4H, m)
(c) 7.36 (4H, m)
(d) 8.04 (1H, s)

EXAMPLE 4A 3-(2-Chloro-4-pyrimidinyl)- 1,1-pentamethyleneurea (Compound No. 4)

2,4-Dichloropyrimidine ( 3.00 g; 20.1 mmoles) and 2.90 g ( 20.1 mmoles) of 3-hydroxy-1,1-pentamethylene urea were dissolved in 40 ml of N,N-dimethylformamide (DMF). The solution was cooled to −25° C., and 20 ml of a DMF solution of 2.26 g (20.1 mmoles) of potassium t-butoxide was added dropwise over the course of 25 minutes. The mixture was stirred at −25° to −10° C. for 3 hours and then 250 ml of water was added. The mixture was extracted with ethyl acetate. The extract was washed with a saturated aqueous solution of sodium chloride, and dried over anhydrous magnesium sulfate. Ethyl acetate was evaporated under reduced pressure, and the residue was purified by silica gel column chromatography (eluting solvent: ethyl acetate/hexane). Recrystallization from toluene/hexane gave 0.78 g (yield 15%) of the captioned compound a colorless crystals.

Melting point: 136°-138° C.

Mass spectrum (FD method): m/z 259 (molecular ion peak)

IR spectrum (KBr tablet, $cm^{-1}$): 3200, 1660, 1555, 1510, 1408, 1347, 1294, 1265, 1252, 1220, 1210, 1192, 1076, 1015, 978, 910, 862, 840, 765, 720

$^1$H-NMR spectrum ($CDCl_3$ solution, ppm)

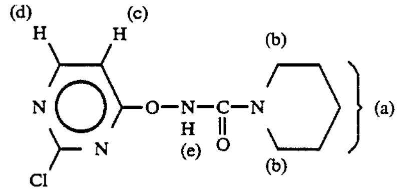

(a) 1.65 (6H, m)
(b) 3.44 (4H, m)
(c) 6.96 (1H, d, J=5.7 Hz)
(d) 8.42 (1H, d, J=5.7 Hz)
(e) 8.78 (1H, s)

EXAMPLES 5A14 80A

In the same way as in examples 1A to 4A, compound Nos. 5 to 80 shown in Table 1 were synthesized from the corresponding starting materials. The results are shown in Table 1A. Methods A, B, C and D in Table 1A show that they correspond respectively to the methods described in examples 1A, 2A, 3A and 4A.

TABLE 1A

| Compound No. | Method | Yield (%) | Melting point (°C.) | IR spectrum ($cm^{-1}$) | | |
|---|---|---|---|---|---|---|
| | | | | $\nu_{C=O}$ | $\nu_{N-H}$ | Other characteristic absorption |
| 5 | A | 81 | 113–115 (decomp.) | 1645 | 3200 | |
| 6 | B | 59 | 103–105 (decomp.) | 1650 | 3500, 3170 | |
| 7 | A | 52 | 112–114 (decomp.) | 1643 | 3200 | |
| 8 | B | 75 | 120–121 (decomp.) | 1660 | 3390, 3150 | |
| 9 | A | 42 | 109–110 (decomp.) | 1650 | 3120 | |
| 10 | B | 85 | 139–140.5 (decomp.) | 1665 | 3400, 3160 | |
| 11 | A | 65 | 118–120 (decomp.) | 1655 | 3200 | |
| 12 | A | 32 | 116–120 | 1660 | 3140 | |
| 13 | A | 64 | 121–123 (decomp.) | 1665 | 3050 | |
| 14 | B | 66 | 120–120.5 (decomp.) | 1655 | 3290, 3250 | |
| 15 | B | 85 | 136–137 (decomp.) | 1660 | 3290, 3260 | |
| 16 | A | 40 | 105–106 (decomp.) | 1640 | 3100 | |
| 17 | A | 48 | 105–106.5 (decomp.) | 1650 | 3100 | |
| 18 | A | 14 | 142–144 (decomp.) | 1660 | 3095 | |
| 19 | A | 68 | 160–161 (decomp.) | 1660 | 3090 | |
| 20 | A | 39 | 118–120 (decomp.) | 1660 | 3160 | |
| 21 | B | 75 | 122–125 (decomp.) | 1650 | 3340 | |
| 22 | B | 77 | 138–140 (decomp.) | 1660 | 3290 | |
| 23 | C | 87 | 123–125 | 1655 | 3275 | |
| 24 | A | 28 | 127.5–128.5 (decomp.) | 1670 | 3140 | 1510, 1340($\nu_{NO2}$) |
| 25 | B | 32 | 112–114 | 1670 | 3395, 3150, 3080 | 1520, 1350($\nu_{NO2}$) |
| 26 | A | 52 | 122–124 (decomp.) | 1665 | 3190 | 3290($\nu_{\equiv C-H}$), 1515, 1355($\nu_{NO2}$) |
| 27 | A | 70 | 132–133.5 | 1670 | 3190 | 1520, 1350($\nu_{NO2}$) |
| 28 | A | 78 | 80–82 | 1655 | 3150 | 1640($\nu_{C=C}$), 1530, 1355($\nu_{NO2}$) |
| 29 | A | 71 | 145–147 | 1660 | 3180, 3110 | 1525, 1355($\nu_{NO2}$) |
| 30 | A | 67 | 102.5–104.5 | 1645 | 3110 | 1540, 1355($\nu_{NO2}$) |
| 31 | A | 46 | 150–152 (decomp.) | 1670 | 3200 | 1540, 1340($\nu_{NO2}$) |
| 32 | B | 79 | 143–144.5 (decomp.) | 1660 | 3400, 3350, 3250 | 1540, 1340($\nu_{NO2}$) |
| 33 | B | 62 | 136–138 (decomp.) | 1670 | 3420, 3140, 3090 | 1545, 1330($\nu_{NO2}$) |
| 34 | B | 68 | 136–138 (decomp.) | 1670 | 3380, 3140, 3090 | 1530, 1345($\nu_{NO2}$) |
| 35 | B | 63 | 136–137 | 1665 | 3320, 3220 | 1640($\nu_{C=C}$), 1510, 1345($\nu_{NO2}$) |
| 36 | B | 80 | 139–141 | 1660 | 3380, 3150 | 1530, 1345($\nu_{NO2}$) |
| 37 | B | 32 | 142–144 | 1675 | 3380, 3160 | 1540, 1335($\nu_{NO2}$) |
| 38 | B | 53 | 146–148 | 1685 | 3380, 3160 | 3300($\nu_{\equiv C-H}$) |
| 39 | B | 74 | 153–155 (decomp.) | 1665 | 3390, 3150 | 1535, 1335($\nu_{NO2}$) |
| 40 | B | 47 | 166–168 (decomp.) | 1665 | 3400, 3100 | 1530, 1330($\nu_{NO2}$) |
| 41 | A | 49 | 112–113 | 1665 | 3100 | 1510, 1345($\nu_{NO2}$) |
| 42 | B | 31 | 158–160 (decomp.) | 1655 | 3380, 3140, 3090 | 1535, 1340($\nu_{NO2}$) |
| 43 | A | 18 | 121–123 | 1655 | 3110 | 1515, 1345($\nu_{NO2}$) |
| 44 | A | 9 | 132–134 | 1665 | 3110 | 1515, 1345($\nu_{NO2}$) |
| 45 | A | 45 | 139–141 (decomp.) | 1665 | 3160 | 1510, 1340($\nu_{NO2}$) |
| 46 | B | 58 | 157–159 (decomp.) | 1670 | 3410, 3170 | 1510, 1340($\nu_{NO2}$) |

TABLE 1A-continued

| Compound No. | Method | Yield (%) | Melting point (°C.) | IR spectrum (cm$^{-1}$) $\nu_{C=O}$ | $\nu_{N-H}$ | Other characteristic absorption |
|---|---|---|---|---|---|---|
| 47 | A | 20 | 116.5-118.5 (decomp.) | 1655 | 3120 | 1510, 1335($\nu_{NO_2}$) |
| 48 | B | 24 | 114-116 | 1665 | 32710 | 1530, 1320($\nu_{NO_2}$) |
| 49 | B | 22 | 126-128 | 1670 | 3300, 3230 | 1530, 1320($\nu_{NO_2}$) |
| 50 | C | 59 | 115-117 | 1650 | 3270 | |
| 51 | C | 65 | 137-139 | 1655 | 3220 | 2230($\nu_{C\equiv N}$) |
| 52 | A | 79 | 151-152 (decomp.) | 1670 | 3130 | 2220($\nu_{C\equiv N}$) |
| 53 | C | 71 | 140.5-142 | 1665 | 3200 | 2240($\nu_{C\equiv N}$) |
| 54 | C | 6 | 153-155 | 1645 | 3220 | |
| 55 | B | 52 | 163-165 (decomp.) | 1650 | 3300, 3250 | 2220($\nu_{C\equiv N}$) |
| 56 | C | 30 | 99-101 | 1650 | 3260 | |
| 57 | C | 27 | liquid | 1675 | 3190 | |
| 58 | B | 70 | 103-105 | 1660 | 3300, 3160 | |
| 59 | A | 55 | 121-122 | 1645 | 3180 | |
| 60 | C | 35 | 64-66 | 1660 | 3110 | |
| 61 | C | 63 | 76-78 | 1660 | 3140 | |
| 62 | A | 55 | 102-104 | 1650 | 3185 | |
| 63 | B | 88 | 141-143 | 1660 | 3280, 3170, 3080 | |
| 64 | A | 65 | 138-139 | 1645 | 3180 | |
| 65 | A | 57 | 160-163 | 1655 | 3190 | |
| 66 | C | 49 | 161-163 | 1665 | 3130 | |
| 67 | C | 56 | 127-129 | 1675, 1650 | 3150 | |
| 68 | A | 65 | 109-111 | 1640 | 3150 | |
| 69 | C | 42 | 121-123 | 1665 | 3180 | |
| 70 | A | 56 | 99-101 | 1655 | 3200 | |
| 71 | C | 53 | 131-132 | 1665 | 3205 | |
| 72 | A | 32 | 129-131 | 1655 | 3200, 3160 | |
| 73 | C | 55 | 114-116 | 1640 | 3160 | |
| 74 | C | 49 | 104-106 | 1650 | 3030 | |
| 75 | C | 71 | 94-96 | 1650 | 3220 | |
| 76 | A | 29 | 130-132 | 1640 | 3190 | |
| 77 | A | 29 | 146-148 | 1655 | 3200, 3160 | |
| 78 | A | 26 | 92-94 | 1645 | 3230 | |
| 79 | A | 15 | 101-103 | 1655, 1645 | 3220 | |
| 80 | D | 24 | 132-134 (decomp.) | 1665 | 3180, 3150 | |
| 82 | D | 24 | 102-104 | 1655 | 3210 | |
| 83 | D | 20 | 86-88 | 1660 | 3150 | |
| 84 | C | 20 | 120-123 | 1655 | 3150 | |
| 85 | C | 39 | 236-239 | 1665 | 3180 | |
| 86 | D | 31 | 102-104 | 1655 | 3150 | |
| 87 | D | 20 | liquid | 1660 | 3180 | |
| 88 | D | 24 | 127-129 | 1655 | 3200 | |
| 89 | D | 20 | 125-127 | 1660 | 3150 | |
| 90 | D | 33 | 114-116 | 1655 | 3180 | |
| 91 | D | 56 | 135-137 | 1660 | 3150 | |
| 92 | D | 19 | 123-125 | 1660 | 3140 | |
| 93 | D | 51 | 169-171 (decomp.) | 1660 | 3130 | |

EXAMPLE 81A 1-t-Butyl-3-(2,5-dichlorophenoxy)-3-formylurea (Compound No. 94)

A mixture of 1.53 g (33.3 mmoles) of formic acid and 3.24 g (31.8 mmoles) of acetic anhydride was stirred at 60° C. for 2.5 hours, and 2.20 g (7.94 mmoles) of 1-t-butyl-3-(2,5-dichlorophenoxy)urea was added. The mixture was stirred at 60° C. for 5 hours. The reaction mixture was cooled to room temperature, and 100 ml of ethyl acetate was added. The mixture was washed with a saturated aqueous solution of sodium chloride, and dried over anhydrous magnesium sulfate. The ethyl acetate was evaporated under reduced pressure. The residue was purified by silica gel column chromatography (eluting solvent: ethyl acetate/hexane) to give 1.48 g of the desired compound as colorless crystals(yield 61%).

(Melting point: 101°-102° C.

Mass spectrum (FD method): m/z 304 (molecular ion peak)

IR spectrum (KBr tablet method, cm$^{-1}$): 3400, 3380, 1730, 1705, 1572, 1503, 1464, 1389, 1268, 1195, 1092, 910, 815

$^1$H-NMR spectrum ($CDCl_3$ solution, ppm)

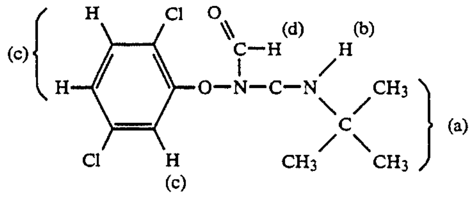

(a) 1.39 (9H,s)

(b) 6.24 (1H, br, s)
(c) 7.0–7.4 (3H, m)
(d) 9.22 (1H, s)

EXAMPLE 82A

3-Acetyl-3-(3,5-dichlorophenoxy)-1,1-hexamethyleneurea (compound No. 95)

In a mixed solvent of 20 ml of tetrahydrofuran and 1.6 ml of pyridine was dissolved 2.0 g (6.6 mmoles) of 3-(3,5-dichlorophenoxy)-1,1-hexamethyleneurea, and 10 ml of a tetrahydrofuran solution of 1.0 g (13.2 mmoles) of acetyl chloride was added. The mixture was stirred at 25° C. for 2 hours and then at 50° C. for 2 hours. The reaction mixture was cooled to room temperature, and 100 ml of water was added. The mixture was extracted with ethyl acetate, and the extract was washed with a diluted sulfuric acid solution and then with a saturated aqueous sodium chloride solution, and dried over anhydrous magnesium sulfate. The ethyl acetate was evaporated under reduced pressure. The residue was purified by silica gel column chromatography (eluting solvent: ethyl acetate/hexane). Recrystallization from toluene/-hexane gave 1.72 g (yield 75%) of the desired compound as colorless needle-like crystals.

Melting point: 65°–66° C.

Mass spectrum (FD method): m/z 344 (molecular ion peak)

IR spectrum (KBr tablet, $cm^{-1}$): 1720, 1685, 1580, 1430, 1375, 1270, 1205, 1100 930, 845

$^1H$-NMR spectrum ($CDCl_3$ solution, ppm)

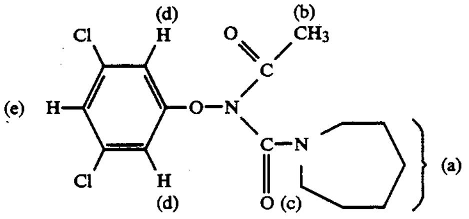

(a) 1.4–2.0 (8H, m)
(b) 2.27 (3H, s)
(c) 3.53 (4H, m)
(d) 7.01 (2H, d, J=1.8 Hz)
(e) 7.09 (1H, d, J=1.8 Hz)

EXAMPLE 83A 3-(3,5-dichlorophenoxy)-1-isopropyl-3-methoxycarbonyl-1-methylurea (Compound No. 96)

In a mixed solvent of 20 ml of tetrahydrofuran and 1.9 ml of pyridine was dissolved 2.15 g (7.76 mmoles) of 3-(3,5-dichlorophenoxy)-1-isopropyl-1-methylurea, and then 10 ml of a tetrahydrofuran solution of 1.47 g (15.5 mmoles) of methyl chloroformate was added. The mixture was stirred at 25° C. for 2 hours. Water (100 ml) was added to the reaction mixture, and the mixture was extracted with ethyl acetate. The extract was washed with a saturated aqueous sodium chloride solution, and dried over anhydrous magnesium sulfate. The ethyl acetate was evaporated under reduced pressure. The residue was purified by silica gel column chromatography (eluting solvent: ethyl acetate/hexane) to give 1.14 g (yield 44% of the desired compound as the yellow crystals.

Melting point: 67°–69° C.

Mass spectrum (FD method): m/z 334 (molecular ion peak)

IR spectrum (KBr tablet, $cm^{-1}$): 1742, 1708, 1581, 1432, 1280, 1095, 942, 840

$^1H$-NMR spectrum ($CDCl_3$ solution, ppm)

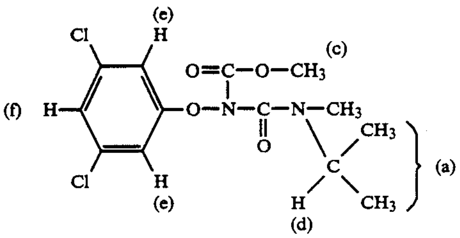

(a) 1.21 (6H, d, J=6.6 Hz)
(b) 2.91 (3H, s)
(c) 3.87 (3H, s)
(d) 4.46 (1H, m)
(e) 7.01 (2H, m).
(f) 7.07 (1H, m)

EXAMPLE 84A 3-(2,5-Dichlorophenoxy)-3-hydroxymethyl-1-n-propylurea (Compound No. 97)

In 10 ml of N,N-dimethylformamide was dissolved 2.0 g (7.6 mmoles) of 3-(2,5-dichlorophenoxy)-1-n-propyl-urea, and then 1.87 g (22.8 mmoles) of 37% aqueous formalin solution was added. The mixture was stirred at 25° C. for 3 hours. Water (100 ml) was added to the reaction mixture, and the mixture was extracted with ethyl acetate. The extract was washed with a saturated aqueous sodium chloride solution, and dried over anhydrous magnesium sulfate. The ethyl acetate was evaporated under reduced pressure. The residue was recrystallized from ethyl acetate and toluene to give 1.4 g (yield 63%) of the desired compound as colorless crystals.

Melting point: 119°–121° C. (decomp.)

Mass spectrum (FD method): m/z 292 (molecular ion peak)

IR spectrum (KBr tablet, $cm^{-1}$): 3320, 1665, 1580, 1530, 1470, 1275, 1215, 1085, 1045, 955, 920, 860, 800

$^1H$-NMR spectrum ($CDCl_3$ solution, ppm)

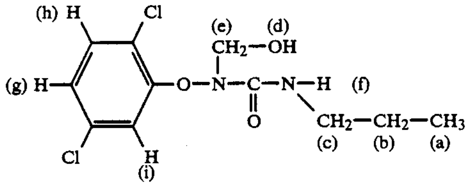

(a) 0.92 (3H,t,J=7.2 Hz)
(b) 1.3–1.8 (2H, m)
(c) 3.1–3.4 (2H, m)
(d) 3.90 (1H,t,J=7.2 Hz)
(e) 5.15 (2H,d,J=7.2 Hz)
(f) 5.8–6.1 (1H, m)

(g) 7.05 (1H, d,J=9.0, 1.8 Hz)

(h) 7.35 (1H, d,J=9.0 Hz)

(i) 7.40 (1H,d,J=1.8 Hz)

EXAMPLES 85A-160A

By the same methods as in examples 81A to 84A Compound Nos. 98-173 were synthesized from the corresponding starting materials described in Table 2. The results are shown in Table 2A. A, B, C and D under the headline "method of production" correspond respectively to the methods of production described in examples 31A, 82A, 83A and 84A.

TABLE 2A

| Compound No. | Method of production | Yield (%) | Melting point (°C.) | IR spectrum $\nu_{c=o}$(cm$^{-1}$) |
|---|---|---|---|---|
| 98 | B | 91 | liquid | 1715, 1690 |
| 99 | B | 51 | liquid | 1710, 1690 |
| 100 | A | 54 | 108-109 | 1720, 1690 |
| 101 | B | 86 | 98-99 | 1725, 1685 |
| 102 | B | 85 | 103-104 | 1725, 1685 |
| 103 | B | 8 | 135-137 (decomp.) | 1740, 1710 |
| 104 | B | 93 | 111-112 | 1740, 1700 |
| 105 | C | 84 | 97-98 | 1735, 1715 |
| 106 | A | 96 | liquid | 1720 (broad) |
| 107 | B | 78 | 115-116 | 1736, 1727 |
| 108 | B | 90 | 133-135 (decomp.) | 1740, 1710 |
| 109 | C | 72 | 103-104 | 1730 |
| 110 | B | 63 | solid solution | 1740, 1690 |
| 111 | B | 39 | 70-71 | 1740, 1700 |
| 112 | C | 71 | liquid | 1745, 1700 |
| 113 | B | 40 | 102-103 | 1705 (broad) |
| 114 | A | 75 | 84-85 | 1735, 1725, 1705 |
| 115 | B | 80 | 122-123 (decomp.) | 735, 1725, 1685 |
| 116 | B | 85 | 130-132 | 1745, 1735, 1700 |
| 117 | C | 69 | 98-99 | 1740, 1725, 1695 |
| 118 | C | 74 | 84-85 | 1740, 1725, 1700 |
| 119 | C | 81 | liquid | 1740, 1710 |
| 120 | C | 97 | liquid | 1740, 1705 |
| 121 | C | 95 | liquid | 1740, 1705 |
| 122 | A | 89 | 88-89 | 1725, 1695 |
| 123 | B | 71 | 102-103 | 1730, 1690 |
| 124 | B | 75 | 86-87 | 1735, 1710 |
| 125 | C | 64 | 109-110 | 1725, 1705 |
| 126 | A | 77 | liquid | 1725, 1710, 1690 |
| 127 | B | 88 | liquid | 1710 (broad) |
| 128 | B | 79 | liquid | 1710 |
| 129 | B | 88 | 145-1461 (decomp.) | 725, 1685 |
| 130 | C | 83 | 131-132 | 1750, 1705 |
| 131 | B | 78 | 79-80 | 1700 (broad) |
| 132 | A | 72 | 96-97 | 1690 |
| 133 | B | 77 | 119-120 | 1725, 1700 |
| 134 | B | 95 | 89-90 | 1720, 1695 |
| 135 | B | 48 | 111-112 | 1740, 1700 |
| 136 | B | 87 | 55-58 | 1700 (broad) |
| 137 | C | 58 | liquid | 1740, 1700 |
| 138 | A | 51 | liquid | 1720, 1695 |
| 139 | B | 85 | 95-96 | 1715, 1690 |
| 140 | B | 77 | 106-107 | 1730, 1700 |
| 141 | A | 51 | 109-110 | 1720, 1690 |
| 142 | B | 94 | liquid | 1710 |
| 143 | B | 26 | solid solution | 1710 (broad) |
| 144 | C | 80 | 72-73 | 1745, 1710 |
| 145 | A | 36 | 114-115 | 1690, 1675 |
| 146 | B | 88 | 82-83 | 1720, 1690 |
| 147 | B | 62 | 57-58 | 1725, 1700, 1683 |
| 148 | B | 62 | 74-75 | 1705 (broad) |
| 149 | B | 36 | 76-77 | 1740, 1730 |
| 150 | C | 40 | liquid | 1745, 1705 |
| 151 | B | 92 | 79-81 | 1700 (broad) |
| 152 | B | 90 | 92-93 | 1700 (broad) |
| 153 | B | 95 | 72-75 | 1700 (broad) |
| 154 | A | 62 | 102-103 | 1700, 1685 |
| 155 | A | 78 | 63-64 | 1710, 1680 |
| 156 | B | 79 | liquid | 1690 (broad) |
| 157 | A | 87 | liquid | 1710, 1690 |

TABLE 2A-continued

| Compound No. | Method of production | Yield (%) | Melting point (°C.) | IR spectrum $\nu_{c=o}$(cm$^{-1}$) |
|---|---|---|---|---|
| 158 | B | 97 | liquid | 1700 (broad) |
| 159 | A | 84 | liquid | 1715, 1685 |
| 160 | B | 89 | liquid | 1690 (broad) |
| 161 | A | 67 | 78-79 | 1730, 1690 |
| 162 | B | 94 | 77-78 | 1735, 1695 |
| 163 | B | 98 | 98-99 | 1740, 1710 |
| 164 | C | 92 | 85-86 | 1745, 1705 |
| 165 | D | 91 | 70-72 | 1680 (broad) |
| 166 | B | 85 | 85-86 | 1720, 1710 |
| 167 | C | 62 | 99-100 | 1735, 1705 |
| 168 | A | 63 | 93-94 | 1685 (broad) |
| 169 | B | 66 | liquid | 1690 (broad) |
| 170 | B | 92 | 113-115 | 1685 (broad) |
| 171 | B | 86 | 120-121 | 1705, 1685 |
| 172 | C | 67 | 92-93 | 1740, 1700 |

EXAMPLE 161A 3-(2,5-Dichlorophenoxy)-3-ethoxymethyl-1-n-propylurea (Compound No. 174)

To 2.63 g of 3-(2,5-dichlorophenoxy)-1-n-propylurea, were added 4.14 g (20 mmoles) of anhydrous potassium carbonate and then 1.42 g (15 mmoles) of chloromethyl ethyl ether. The mixture was stirred at 50° C. for 1 hour. The reaction mixture was cooled to room temperature, and 300 ml of water was added. The mixture was extracted with ethyl acetate. The extract was washed with a saturated aqueous solution of sodium chloride and dried over anhydrous magnesium sulfate. The ethyl acetate was evaporated under reduced pressure, and the residue was purified by silica gel column chromatography (eluting solvent: ethyl acetate/hexane) to give 0.44 g (yield 14%) of the desired compound as a pale yellow oil.

Mass spectrum (FD method): m/z 320 (molecular ion peak)

IR spectrum (neat, cm$^{-1}$): 3430, 1643, 1575, 1465, 1398, 1375, 1235, 1160, 1079, 975, 798

$^1$H-NMR spectrum ($CDCl_3$ solution, ppm)

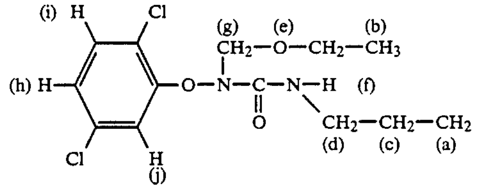

(a) 0.95 (3H,t,J=7.2 Hz)

(b) 1.29 (3H,t,J=7.2 Hz)

(c) 1.58 (2H, m)

(d) 3.21 (2H, m)

(e) 3.80 (2H,q,J=7.2 Hz)

(f) 5.1 (1H, m)

(g) 5.40 (2H, s)

(h) 6.85 (1H,d,J=8.8, 2.2 Hz)

(i) 7.22 (1H,d,J=8.8 Hz)

(j) 7.50 (1H,d,J=2.2 Hz)

EXAMPLE 162A 3-(3,5-Dichloro-2-pyridyloxy)-3-ethoxycarbonyl-1,1-pentamethyleneurea (Compound No. 175)

Ethyl N-(3,5-dichloro-2-pyridyloxy)carbamate (2.20 g; 8.76 mmoles) was dissolved in 3.5 ml of pyridine, and 1.94 g (13.1 mmoles) of 1-chloroformylpiperidine was added. The mixture was stirred at 50° C. for 20 hours. The reaction mixture wa cooled to room temperature, and 250 ml of water was added. The mixture was extracted with ethyl acetate. The extract was washed with a saturated aqueous solution of sodium chloride, and dried over anhydrous magnesium sulfate. The ethyl acetate was evaporated under reduced pressure, and the residue was purified by silica gel column chromatography (eluting solvent: ethyl acetate/hexane) to give 2.75 g (yield 76%) of the desired compound as an orange liquid.

Mass spectrum (FD method): m/z 361 (molecular ion peak)

IR spectrum (neat, $cm^{-1}$): 1735, 1700, 1420, 1380, 1300, 1245, 1220, 1105

$^1H$-NMR spectrum($CDCl_3$ solution, ppm)

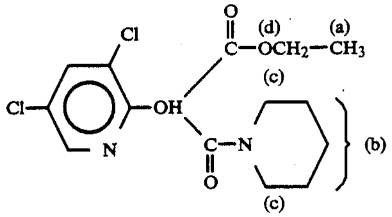

(a) 1.30 (3H, t, J=7.0 Hz)
(d) 4.29 (2H, q, J=7.0 Hz)
(e) 7.73 (1H, d, J=2.0 Hz)
(f) 8.01 (1H, d, J=2.0 Hz)

EXAMPLE 163A 3-(3-Trifluoromethyl-2-pyridyloxy)-3-ethoxycarbonyl-1-n-propylurea (Compound No. 176)

Ethyl N-(3-trifluoromethyl-2-pyridyloxy)-carbamate (2.30 g; 9.19 mmoles) was dissolved in 50 ml of toluene, and 2.34 g (27.6 mmoles) of n-propyl isocyanate and 0.2 g (2.0 mmoles) of triethylamine were added, and the mixture was stirred at 45° C. for 40 hours. The toluene and the excess of n-propyl isocyanate in the reaction mixture were evaporated under reduced pressure. The residue was purified by silica gel column chromatography (eluting solvent ethyl acetate/hexane) to give 2.61 g (yield 85%) of the desired compound as a colorless liquid.

Mass spectrum (FD method): m/z 335 (molecular ion peak)

$^1R$ spectrum (neat, $cm^{-1}$): 3350, 1740, 1705, 1600, 1585, 1525, 1430, 1375, 1320, 1220, 1150, 1070, 1035, 1005, 920

$^1H$-NMR spectrum ($CDCl_3$ solution, ppm)

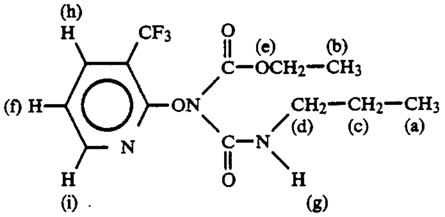

(a) 0.96 (3H, t, J=7.0 Hz)
(b) 1.20 (3H, t, J=7.0 Hz)
(c) 1.60 (2H, m)
(d) 3.30 (2H, q, J=7.0 Hz)
(e) 4.24 (2H, q, J=7.0 Hz)
(f) 7.16 (1H, dd, J=7.4, 5.3 Hz)
(g) 7.9 (1H, br,s)
(h) 7.98 (1H, d, J=7.4 Hz)
(i) 8.30 (1H, d, J=5.3 Hz)

EXAMPLES 64A-244A

The Compound Nos. 177-257 described in Table 2 were synthesized from the corresponding starting materials by the same methods as in examples 162A and 163A. The results are shown in Table 2A. Methods of production E and F in Table 2A respectively correspond to the methods of production described in Examples 162A and 163A.

TABLE 2A

| Compound No. | Method of production | Yield (%) | Melting point (°C.) | IR spectrum $\nu_{C=O}$($cm^{-1}$) |
|---|---|---|---|---|
| 177 | E | 41 | 74-76 | 1750, 1730 |
| 178 | F | 91 | liquid | 1740, 1705 |
| 179 | E | 93 | liquid | 1735, 1705 |
| 180 | F | 91 | 107-109 | 1715, 1685 |
| 181 | F | 95 | 70-72 | 1735, 1695 |
| 182 | E | 78 | liquid | 1740, 1705 |
| 183 | E | 77 | liquid | 1745, 1705 |
| 184 | F | 82 | liquid | 1740, 1710 |
| 185 | E | 97 | liquid | 1740, 1705 |
| 186 | E | 60 | liquid | 1735, 1705 |
| 187 | E | 65 | liquid | 1740, 1705 |
| 188 | F | 93 | liquid | 1740, 1705 |
| 189 | E | 36 | liquid | 1740, 1695 |
| 190 | E | 33 | liquid | 1740, 1705 |
| 191 | E | 33 | liquid | 1740, 1700 |
| 192 | E | 43 | liquid | 1740, 1695 |
| 193 | E | 30 | liquid | 1735, 1695 |
| 194 | E | 35 | liquid | 1740, 1700 |
| 195 | E | 97 | liquid | 1735, 1700 |
| 196 | E | 69 | liquid | 1730, 1705 |
| 197 | E | 72 | liquid | 1730, 1705 |
| 198 | E | 51 | liquid | 1730, 1695 |
| 199 | E | 40 | liquid | 1730, 1700 |
| 200 | E | 60 | liquid | 1730, 1700 |
| 201 | E | 66 | liquid | 1740, 1695 |
| 202 | E | 92 | liquid | 1735, 1700 |
| 203 | E | 99 | liquid | 1730, 1700 |
| 204 | E | 100 | liquid | 1730, 1700 |
| 205 | F | 74 | liquid | 1740, 1710 |
| 206 | E | 65 | liquid | 1725, 1700 |
| 207 | F | 99 | liquid | 1740, 1705 |
| 208 | E | 78 | liquid | 1740, 1700 |
| 209 | E | 26 | 125-127 | 1760, 1705 |
| 210 | F | 99 | liquid | 1740, 1710 |
| 211 | E | 94 | liquid | 1740, 1705 |
| 212 | E | 36 | liquid | 1735, 1705 |
| 213 | E | 38 | liquid | 1740, 1695 |
| 214 | E | 32 | liquid | 1735, 1695 |
| 215 | E | 76 | liquid | 1730, 1705 |
| 216 | E | 49 | liquid | 1730, 1700 |
| 217 | E | 54 | liquid | 1730, 1695 |
| 218 | E | 53 | liquid | 1730, 1700 |

TABLE 2A-continued

| Compound No. | Method of production | Yield (%) | Melting point (°C.) | IR spectrum $\nu_{c=o}$(cm$^{-1}$) |
|---|---|---|---|---|
| 219 | E | 34 | liquid | 1735, 1695 |
| 220 | E | 85 | liquid | 1750, 1700 |
| 221 | E | 88 | liquid | 1750, 1705 |
| 222 | E | 82 | liquid | 1735, 1705 |
| 223 | E | 48 | liquid | 1735, 1695 |
| 224 | E | 36 | liquid | 1735, 1700 |
| 225 | E | 62 | liquid | 1735, 1700 |
| 226 | E | 46 | liquid | 1730, 1700 |
| 227 | E | 53 | liquid | 1735, 1710 |
| 228 | E | 79 | liquid | 1750, 1705 |
| 229 | E | 99 | liquid | 1740, 1705 |
| 230 | E | 72 | liquid | 1740, 1700 |
| 231 | E | 71 | liquid | 1740, 1700 |
| 232 | E | 93 | liquid | 1735, 1705 |
| 233 | E | 68 | liquid | 1740, 1705 |
| 234 | E | 82 | liquid | 1740, 1710 |
| 235 | E | 75 | 62-63 | 1750, 1700 |
| 236 | E | 61 | liquid | 1740, 1700 |
| 237 | E | 70 | liquid | 1740, 1700 |
| 238 | E | 76 | liquid | 1740, 1710 |
| 239 | E | 60 | liquid | 1740, 1710 |
| 240 | E | 73 | liquid | 1740, 1710 |
| 241 | E | 84 | liquid | 1730, 1700 |
| 242 | E | 85 | liquid | 1730, 1700 |
| 243 | E | 55 | liquid | 1720, 1700 |
| 244 | E | 68 | liquid | 1740, 1705 |
| 245 | E | 95 | liquid | 1730, 1705 |
| 246 | E | 72 | liquid | 1720, 1705 |
| 247 | E | 84 | liquid | 1725, 1705 |
| 248 | E | 65 | liquid | 1745, 1705 |
| 249 | E | 71 | liquid | 1740, 1705 |
| 250 | E | 55 | liquid | 1745, 1705 |
| 251 | E | 58 | liquid | 1740, 1700 |
| 252 | E | 63 | liquid | 1740, 1705 |
| 253 | E | 52 | liquid | 1740, 1710 |
| 254 | E | 30 | liquid | 1740, 1710 |

EXAMPLE 245A 3-(6-Chloro-2-methylthio-4-pyrimidinyl)-1,1-pentamethyleneurea (Compound No. 258)

4.98 g (25.5 mmoles) of 4,6-dichloro-2-methylthiopyrimidine and 4.85 g (30.7 mmoles) of 3-hydroxy-3-methyl-1,1-pentamethyleneurea were dissolved in 30 ml of N,N-dimethylformamide (DMF). The solution was cooled to −30° C., and 30 ml of a DMF solution of 3.44 g (30.7 mmoles) of potassium t-butoxide was added dropwise over 15 minutes. The temperature was raised gradually from −30° C., and after it reached +20 ° C., the mixture was stirred further for 2 hours. Water (300 ml) was added to the reaction mixture, and the mixture was extracted with ethyl acetate. The extract was washed with a saturated aqueous solution of sodium chloride, and dried over anhydrous magnesium sulfate. The ethyl acetate was evaporated under reduced pressure. The residue was purified by silica gel column chromatography (eluting solvent: ethyl acetate/hexane) to give 2.71 g (yield 34%) of the desired compound as a colorless liquid.

Mass spectrum (FD method): m/z 316 (molecular ion peak)

IR spectrum (neat, cm$^{-1}$): 1680, 1550, 1525, 1425, 1385, 1310, 1275, 1215, 1130, 1100, 990, 940.

$^1$H-NMR spectrum ($CDCl_3$ solution, ppm):

(a) 1.60 (6H, m), (b) 2.56 (3H, s), (c) 3.16 (3H, s), (d) 3.40 (4H, m), (e) 6.70 (1H, s).

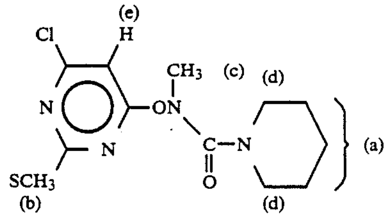

EXAMPLE 246A

Compound No. 259 described in Table 2 was synthesized from the corresponding starting materials by the same method as in Example 245A.

Liquid

Yield: 83%

IR spectrum (neat, cm$^{-1}$): 1675, 1562, 1545, 1410, 1345, 1225, 1130.

EXAMPLE 247

3-(2,5-Dichlorophenoxy)-1,1-dimethyl urea (Compound No. 260)

5.00 g (28.1 mmoles) of 2,5-dichlorophenoxyamine was dissolved in 6.8 ml of pyridine, and then 3.02 g (28.1 mmoles) of dimethylcarbamoyl chloride was added. The mixture was stirred at a temperature of from 25° to 30° C. for 12 hours. After an addition of 200 ml of water, the reaction mixture was extracted with ethyl acetate. The extract was washed with a saturated sodium chloride aqueous solution, and dried over anhydrous magnesium sulfate. Ethyl acetate was distilled off under reduced pressure, and precipitated crystals were washed with hexane, whereby 4.33 g of the desired product was obtained as light yellow crystals (yield: 62%).

Melting point: 119°-121° C. (decomposed)

Elemental analysis: C: 43.31%, H: 4.04%, H, 11.22%. Calculated values as $C_9H_{10}C_{12}N_2O_2$ C: 43.40%, H: 4.05%, N: 11.25%.

Mass spectrum (FD Method): m/z 248 (molecular ion peak)

IR spectrum (KBr tablet, cm): 3210, 1660, 1578, 1496, 1467, 1376, 1190, 1083, 1067, 900, 852, 802, 770 $^1$H-NMR spectrum ($CDCl_3$ solution, ppm)

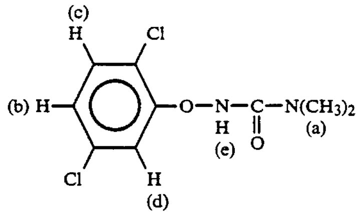

(a) 2.95 (6H, S)

(b) 6.92 (1H, dd, J=8, 2 Hz)

(c) 7.22 (1H, d, J=8 Hz)

(d) 7.31 (1H, d, J=2 Hz)

(e) 8.05 (1H, br.s)

EXAMPLE 248

1-Allyl-3-(2,5-dichlorophenoxy) urea (Compound No. 261)

5.34 g (30.0 mmoles) of 2,5-dichlorophenoxyamine was dissolved in 50 ml of toluene, and then 2.74 g (33.0 mmoles) of allyl isocyanate was added. The mixture was stirred at a temperature of from 25° to 30° C. for 12 hours. The crystals precipitated in the reaction solution were collected by filtration and washed with hexane, whereby, 3.96 g of the desired product was obtained as light yellow crystals (yield: 51%).

Melting point: 130°-131° C. (decomposed)

Mass spectrum (FD Method): m/z 260 (molecular ion peak)

IR spectrum (KBr tablet, cm−1): 3320, 3240, 1660, 1640, 1570, 1468, 1253, 1223, 1083, 1067, 995, 915, 898, 868, 802

1H-NMR spectrum ($CDCl_3$ solution, ppm)

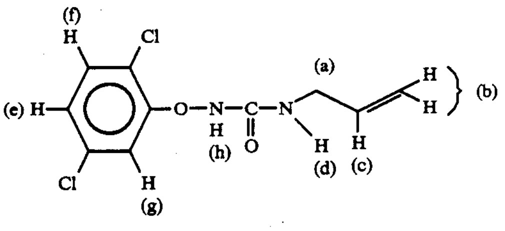

(a) 3.94 (2H, m) (a) 3.94 (2H, m)
(b) 5.0-5.4 (2H, m)
(c) and (d) 5.7-6.1 (2H, m)
(e) 7.04 (1H, dd, J=8, 2 Hz)
(f) 7.30 (1H, d, J=8 Hz)
(g) 7.50 (1H, d, J=2 Hz)
(h) 8.33 (1H, br.s)

REFERENCE EXAMPLE 1

N-(2,3-dichlorophenoxy)carbamic acid phenyl ester 9.10 g (51.1 mmole) of 2,3-dichlorophenoxyamine was dissolved in 7.5 ml of pyridine and 70 ml of dichloromethane, and the solution was cooled to −10° C. Then, 30 ml of a dichloromethane solution containing 7.28 g (46.5 mmole) of phenyl chloroformate was dropwise added thereto over a period of 1 hour, and the mixture was stirred at a temperature of from −10° to 25° C. for 6 hours. The solvent was distilled off under reduced pressure, and 300 ml of ethyl acetate was added. The mixture was washed with water and a saturated sodium chloride aqueous solution, and dried over anhydrous magnesium sulfate. Ethyl acetate was distilled off under reduced pressure, and the residue thereby obtained was recrystallized from toluene/hexane, whereby 11.5 g of the desired product was obtained as light brown crystals (yield: 83%)

Melting point: 114°-115° C. (decomposed)

Mass spectrum (FD Method): m/z 297 (Molecular ion peak)

IR spectrum (KBr tablet, $cm^{-1}$): 3240, 1736, 1573, 1463, 1265, 1230, 768

$^1H$-NMR spectrum ($CDCl_3$ solution, ppm)

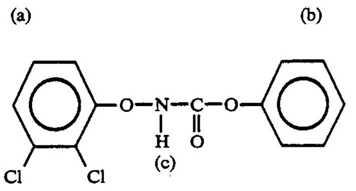

(a) and (b) 7.1-7.5 (8H, m)
(c) 8.36 (1H, br.s)

EXAMPLE 249

1-Cyclohexyl-3-(2,3-dichlorophenoxy) urea (Compound No. 262)

4.00 g (13.4 mmole) of N-(2,3-dichlorophenoxy)carbamic acid phenyl ester synthesized in Reference Example 1 was dissolved in 60 ml of ethyl acetate. 3.32 g (33.5 mmole) of cyclohexylamine as added thereto, and the mixture was reacted at 60° C. for 12 hours, the reaction mixture was cooled to room temperature, and after an addition of 100 ml of ethyl acetate, it was washed with a 3% sodium hydroxide aqueous solution and then with a saturated sodium chloride solution, and then dried over anhydrous magnesium sulfate. Ethyl acetate was distilled off under reduced pressure, and the residue was recrystallized from ethyl acetate-hexane, whereby 2.84 g of the desired product was obtained as light brown crystals (yield: 70%).

Melting point: 136°-138° C. (decomposed)

Mass spectrum (FD Method): m/Z 302 (Molecular ion peak)

IR spectrum (KBr tablet, $cm^{-1}$): 3320, 1650, 1555, 1445, 1425, 1240, 1225, 1185, 765

$^1H$-NMR spectrum ($CDCl_3$ solution, ppm)

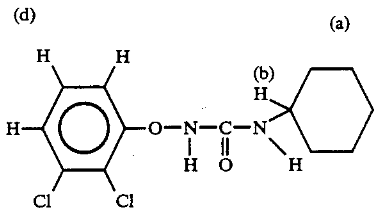

(a) 1.0-2.2 (10H, m)
(b) 3.70 (1H, m)
(c) 5.72 (1H, m)
(d) 7.1-7.3 (3H, m)
(e) 8.18 (1H, br.x)

EXAMPLES 250-329

Compound Nos. 263-442 listed in Table 3 were synthesized in the same manner as the processes of examples 247-249. The results are shown in Table 4. Processes A, B and C in Table 4 correspond to the processes of Examples 247, 248 and 249, respectively.

TABLE 4

| Compound No. | Process | Yield (%) | Melting point (°C.) | IR spectrum ($cm^{-1}$) ν(C=O) | νN—H | Other characteristic absorption | $^1$H-MNR spectrum ($CDCl_3$, ppm) |
|---|---|---|---|---|---|---|---|
| 263 | A | 78 | 132–133 (decomposed) | 1663 | 3160 | | |
| 264 | A | 55 | 131–133 (decomposed) | 1670 | 3120 | | |
| 265 | A | 75 | 121–123 (decomposed) | 1660 | 3120 | | |
| 266 | A | 39 | 137–138 (decomposed) | 1657 | 3110 | | |
| 267 | A | 48 | 106–107 | 1660 | 3140 | | |
| 268 | A | 72 | liquid | 1660 | 3210 | 3290 (υ≡C—H) 2210 (υC≡C) | |
| 269 | A | 50 | 73–74 | 1660 | 3140 | | |
| 270 | A | 70 | 56–57 | 1665 | 3200 | | 1.2(6H, t, J = 7 Hz), 3.24 (4H, q, J = 7 Hz), 6.8–7.3 (4H, m), 8.32 (1H, br.s) |
| 271 | A | 51 | liquid | 1655 | 3190 | | |
| 272 | A | 43 | liquid | 1660 | 3200 | | 3.92 (4H, d, J = 5 Hz), 5.08–5.50 (4H, m), 5.60–6.08 (2H, m), 6.90–7.32 (4H, m) 7.72 (1H, br.s) |
| 273 | A | 46 | 128–129 | 1650 | 3210 | | |
| 274 | A | 78 | 116–117 | 1650 | 3130 | | 1.57 (6H, br.s) 3.33 (4H, br.s), 6.80–7.28 (4H, m), 8.10 (1H, s) |
| 275 | A | 45 | 112–113 | 1650 | 3110 | | |
| 276 | A | 47 | 94–95 | 1650 | 3130 | | |
| 277 | A | 38 | 114–115 | 1655 | 3145 | | |
| 278 | A | 50 | 75–76 | 1649 | 3200 | | 0.87 (3H, t, J = 8 Hz), 1.40–1.60 (8H, m), 6.90–7.30 (3H, m), 7.75 (1H, s) |
| 279 | A | 35 | 91–92 | 1650 | 3170 | | |
| 280 | A | 56 | 115–116 | 1653 | 3280 | | |
| 281 | A | 77 | 148–149 | 1645 | 3270 | | 1.69 (8H, m), 2.03 (2H, br.s), 3.53 (4H, d, J = 4 Hz), 6.88–7.31 (4H, m), 8.08 (1H, s) |
| 282 | C | 45 | 106–108 | 1652 | 3300, 3250 | | |
| 283 | C | 61 | 138–140 (decomposed) | 1650 | 3290, 3260 | | 1.20–2.20 (8H, m), 4.18 (1H, m), (decom-5.74 (1H, d, J = 7 Hz, 7.10–7.28 (3H, m), 8.00 (1H, br.s) |
| 284 | C | 79 | 128–130 (decomposed) | 1658 | 3440, 3220 | | 1.00–2.00 (8H, m), 2.24 (2H, br.s), 3.66 (1H, dd, J = 4, 8 Hz), 5.62 (1H, d, J = 8 Hz), 7.14–7.43 (3H, m), 8.63 (1H, s) |
| 285 | A | 32 | 111–112 | 1650 | 3100 | | |
| 286 | A | 34 | 108–109.5 | 1655 | 3100 | | 0.89 (6H, m), 1.62 (4H, m), 3.18 (4H, m), 7.06–7.26 (3H, m), 7.77 (1H, s) |
| 287 | A | 47 | 145–147 | 1657 | 3150 | | 1.88 (4H, m), 3.38 (4H, m), 7.08–7.36 (3H, m), 7.89 (1H, s) |
| 288 | A | 55 | 130–132 (decomposed) | 1650 | 3185 | | |
| 289 | A | 45 | 137–139 | 1660 | 3220 | | |
| 290 | B | 69 | 135–136 (decomposed) | 1655 | 3310, 3230 | | |
| 291 | B | 45 | 141–142 (decomposed) | 1660 | 3280, 3220 | | |
| 292 | B | 67 | 107–108 (decomposed) | 1660 | 3310, 3225 | | |
| 293 | B | 62 | 135–136 (decomposed) | 1655 | 3300, 3250 | | 1.20 (6H, d, J = 7 Hz), 4.02 (1H, m), 5.60 (1H, m), 7.02 (1H, dd, J = 8, 2 Hz), 7.28 (1H, d, J = 8 Hz, 7.48 (1H, d, J = 2 Hz), 8.36 (1H, br.s) |
| 294 | C | 70 | 131–132 (decomposed) | 1660 | 3290, 3260 | | |

TABLE 4-continued

| Compound No. | Process | Yield (%) | Melting point (°C.) | IR spectrum (cm$^{-1}$) ν(C=O) | νN—H | Other characteristic absorption | $^1$H-MNR spectrum ($CDCl_3$, ppm) |
|---|---|---|---|---|---|---|---|
| 295 | C | 64 | 151-152 (decomposed) | 1659 | 3290, 3240 | 3320 (ν≡C—H) | |
| 296 | C | 72 | 135-136 (decomposed) | 1660 | 3300, 3100 | | |
| 297 | B | 47 | 99-100 (decomposed) | 1658 | 3300, 3240 | | 0.92 (3H, m), 1.2-1.8 (4H, m), 3.32 (2H, m), = 5.78 (1H, m), 7.04 (1H, dd, J = 8, 2 Hz), 7.28 (1H, d, J = 8 Hz), 7.50 (1H, d, J = 2 Hz), 8.24 (1H, br.s) |
| 298 | C | 69 | 130-131 (decomposed) | 1657 | 3300, 3250 | | |
| 299 | C | 85 | 131-132 (decomposed) | 1663 | 3350, 3250 | | |
| 300 | C | 69 | 113-115 (decomposed) | 1665 | 3420, 3080 | | 1.39 (9H, s), 5.73 (1H, s), 7.00 (1H, dd, J = 8 Hz), 7.30 (1H, d, J = 8 Hz), 7.47 (1H, d, J = 2 Hz), 7.93 (1H, s) |
| 301 | C | 65 | 120-121 (decomposed) | 1655 | 3280, 3080 | | |
| 302 | C | 69 | 122-123 | 1645 | 3250, 3090 | | |
| 303 | C | 71 | 132-133 (decomposed) | 1655 | 3290, 3090 | | |
| 304 | C | 55 | 83-85 (decomposed) | 1678 | 3435, 3180 | | |
| 305 | C | 43 | 125-126 (decomposed) | 1670 | 3420, 3170 | 3280 (ν≡C—H) 2140 (νc≡c) | |
| 306 | C | 79 | 139-140 (decomposed) | 1650 | 3300, 3100 | | |
| 307 | C | 80 | 136-138 (decomposed) | 1652 | 3410, 3160 | | |
| 308 | C | 53 | 130-132 (decomposed) | 1650 | 3300, 3200 | | |
| 309 | C | 70 | 141.5-142.5 (decomposed) | 1665 | 3420, 3100 | | |
| 310 | C | 33 | 133-134 (decomposed) | 1655 | 3300, 3250 | | |
| 311 | B | 30 | 149-150.5 (decomposed) | 1650 | 3300, 3240 | | |
| 312 | C | 58 | 138-139 (decomposed) | 1657 | 3320, 3230 | | |
| 313 | C | 43 | 158-159 (decomposed) | 1665 | 3420, 3150 | | |
| 314 | C | 58 | 150-152 (decomposed) | 1670 | 3420, 3160 | | |
| 315 | C | 86 | 231-233.5 (decomposed) | 1668 | 3430, 3140 | | 1.00-2.00 (8H, m), 2.52 (2H, br.s), 3.66 (1H, dt, J = 4, 8 Hz), 5.64 (1H, d, J = 8 Hz), 7.00 (1H, dd, J =8, 2 Hz), 7.30 (1H, d, J = 8 Hz), 7.44 (1H, d, J = 2 Hz), 8.10 (1H, br.s) |
| 316 | C | 82 | 146-147 (decomposed) | 1669 | 3415, 3140 | | |
| 317 | C | 74 | 161-163 (decomposed) | 1673 | 3415, 3140 | | |
| 318 | A | 51 | 113-114 (decomposed) | 1663 | 3100 | | |
| 319 | A | 53 | 128-129 | 1655 | 3100 | | |

TABLE 4-continued

| Compound No. | Process | Yield (%) | Melting point (°C.) | IR spectrum ($cm^{-1}$) ν(C=O) | νN—H | Other characteristic absorption | $^1$H-MNR spectrum ($CDCl_3$, ppm) |
|---|---|---|---|---|---|---|---|
| | | | (decom-posed) | | | | |
| 320 | A | 66 | 102–103 | 1655 | 3100 | | |
| 321 | A | 42 | 133–134 (decom-posed) | 1650 | 3090 | | |
| 322 | A | 65 | 105–106 | 1660 | 3110 | 1640 (νC═C) | |
| 323 | A | 88 | 70–72 (decom-posed) | 1663 | 3200 | 3280 (ν≡C—H) 2120 (νC≡C) | 2.33 (1H, t, J = 2 Hz), 3.00 (3H, s), 4.13 (2H, d, J = 2 Hz), 6.92 (1H, dd, J = 8, 2 Hz), 7.22 (1H, d, J = 8 Hz), 7.30 (1H, d, J = 2 Hz), 8.26 (1H, br.s) |
| 324 | A | 74 | 116–117 | 1660 | 3130 | | |
| 325 | A | 64 | 90.5–92 (decom-posed) | 1658 | 3120 | | |
| 326 | A | 34 | 124–125 (decom-posed) | 1645 | 3130 | | |
| 327 | A | 72 | 117–118 | 1665 | 3180 | | |
| 328 | A | 46 | 114–115 | 1649 | 3120 | | |
| 329 | A | 87 | 122–123 (decom-posed) | 1645 | 3110 | 3280 (ν≡C—H) | |
| 330 | A | 68 | 111–112 | 1660 | 3190 | | |
| 331 | A | 50 | 121–122 (decom-posed) | 1660 | 3220 | | |
| 332 | A | 47 | 106–107 | 1659 | 3180 | | |
| 333 | A | 62 | 113–114 (decom-posed) | 1662 | 3220 | | |
| 334 | A | 38 | 120–121 | 1659 | 3220 | | |
| 335 | A | 48 | 104–105 | 1655 | 3110 | | |
| 336 | A | 29 | 135–137 (decom-posed) | 1645 | 3130 | | |
| 337 | A | 33 | 99–100 | 1668 | 3140 | | |
| 338 | A | 37 | 101–102 (decom-posed) | 1665 | 3210 | | |
| 339 | A | 74 | 70–71 | 1655 | 3110 | 1640 (νC═C) | 3.92 (4H, d, J = 7 Hz), 5.20 (2H, m), 5.32 (2H, m), 5.8 (2H, m), 6.96 (1H, dd, J = 8, 2 Hz), 7.22 (1H, d, J = 8 Hz), 7.28 (1H, d, J = 2 Hz), 7.83 (1H, br.s) |
| 340 | A | 46 | 122–123 (decom-posed) | 1650 | 3120 | 3290 (ν≡C—H) 2120 (νC≡C) | |
| 341 | A | 69 | 131–132 (decom-posed) | 1645 | 3120 | | |
| 342 | A | 50 | 111–113 (decom-posed) | 1645 | 3140 | | |
| 343 | A | 48 | 135–136 (decom-posed) | 1650 | 3140 | | |
| 344 | A | 20 | 120–122 (decom-posed) | 1645 | 3180 | | |
| 345 | A | 60 | 144–145 (decom-posed) | 1660 | 3180 | | |
| 346 | A | 35 | 131.5–133.5 (decom-posed) | 1650 | 3140 | | |
| 347 | A | 22 | 136–137 (decom-posed) | 1650 | 3140 | | |
| 348 | A | 54 | 135–136 (decom-posed) | 1660 | 3200 | | 3.53 (2H, t, J = 6 Hz), 4.05 (2H, t, J = 6 Hz), 4.92 (2H, s), 7.00 (1H, dd, J = 8, 2 Hz), 7.28 (1H, d, J = 8 Hz), 7.44 (1H, d,) J = 2 Hz), 7.80 (1H, br.s) |
| 349 | A | 55 | 139–140 (decom- | 1660 | 3120 | | |

TABLE 4-continued

| Compound No. | Process | Yield (%) | Melting point (°C.) | IR spectrum (cm⁻¹) ν(C═O) | νN—H | Other characteristic absorption | $^1$H-MNR spectrum ($CDCl_3$, ppm) |
|---|---|---|---|---|---|---|---|
| | | | posed) | | | | |
| 350 | A | 75 | 140–141 (decomposed) | 1660 | 3090 | 1642 (νC=C) | 2.17 (2H, m), 3.50 (2H, t, J = 6 Hz), 3.87 (2H, m), 5.64 (1H, m), 5.84 (1H, m), 6.95 (1H, dd, J = 8, 2 Hz), 7.23 (1H, d, J = 8 Hz), 7.34 (1H, d, J = 2 Hz), 8.32 (1H, s) 1.22 |
| 351 | | 47 | 123–124 (decomposed) | 1652 | 3100 | | 1.22 (3H, d, J = 7 Hz), 1.62 (6H, m), 3.00 (1H, m), 3.76 (1H, m), 4.28 (1H, m), 6.94 (1H, dd, J = 8, 2 Hz), 7.24 (1H, d, J = 8 Hz), 7.34 (1H, d, J = 2 Hz), 7.90 (1H, s) |
| 352 | A | 76 | 135–136 (decomposed) | 1655 | 3120 | | |
| 353 | A | 79 | 129–130 (decomposed) | 1654 | 3100 | | |
| 354 | A | 57 | 126–127 (decomposed) | 1645 | 3120 | | |
| 355 | A | 27 | 118–120 (decomposed) | 1640 | 3100 | | |
| 356 | A | 66 | 129–130 (decomposed) | 1652 | 3120 | | |
| 357 | A | 49 | 141–142 (decomposed) | 1660 | 3200 | | 1.80 (4H, m), 3.72 (2H, m), 4.05 (2H, m), 6.96 (1H, dd, J = 8, 2 Hz), 7.24 (1H, d, J = 8 Hz), 7.37 (1H, d, J = 2 Hz), 8.64 (1H, br.s) |
| 358 | A | 73 | 117–118 (decomposed) | 1660 | 3250 | | |
| 359 | A | 52 | 140–141 (decomposed) | 1650 | 3120 | | 3.44 (4H, m), 3.68 (4H, m), 6.96 (1H, dd, J = 8, 2 Hz), 7.22 (1H, d, J =8 Hz), 7.30 (1H, d, J = 2 Hz), 7.72 (1H, br.s) |
| 360 | A | 72 | 124–125 (decomposed) | 1645 | 3120 | | |
| 361 | A | 40 | 131–132 (decomposed) | 1655 | 3100 | | 1.65 (8H, m), 3.44 (4H, m), 6.92 (1H, dd, J = 8, 2 Hz), 7.22 (1H, d, J = 8 Hz), 7.32 (1H, d, (J = 2 Hz), 7.76 (1H, br.s) |
| 362 | A | 48 | 152–154 (decomposed) | 1632 | 3250 | | |
| 363 | A | 30 | 129–130.5 (decomposed) | 1645 | 3100 | | |
| 364 | A | 33 | 156–157 (decomposed) | 1655 | 3250 | | |
| 365 | A | 26 | 145–146 (decomposed) | 1655 | 3180 | | |
| 366 | B | 53 | 163–164 (decomposed) | 1635 | 3360, 3170 | | |
| 367 | C | 56 | 115–116 | 1670 | 3360, 3230 | | |
| 368 | C | 71 | 107–108 | 1670 | 3370, 3160 | | |
| 369 | C | 56 | 138–139.5 (decomposed) | 1670 | 3360, 3320 | 3270 (ν≡C—H) 2100 (νC≡C) | 1.67 (6H, s), 2.37 (1H, s), 5.60 (1H, br.s), 7.10 (3HY, m), 7.80 (1H, br.s) |
| 370 | C | 90 | 160–161 (decomposed) | 1639 | 3350, 3190 | | 1.20–2.20 (8H, m), 4.18 (1H, m), 5.38 (1H, d, J = 7 Hz), 7.10 (3H, m), 8.08 (1H, br.s) |
| 371 | C | 69 | 146–148 (decomposed) | 1635 | 3340, 3180 | | |
| 372 | A | 58 | 133.5–135 | 1655 | 3120 | | 0.09 (3H, t, J = 7 Hz), 1.58 (2H, m), 2.92 (3H, s), 3.22 (2H, t, J = 7 Hz), 7.01 (3H, s), 7.93 (1H, br.s) |
| 373 | A | 56 | 121–122 | 1660 | 3100 | | |

TABLE 4-continued

| Compound No. | Process | Yield (%) | Melting point (°C.) | IR spectrum (cm$^{-1}$) ν(C=O) | νN—H | Other characteristic absorption | $^1$H-MNR spectrum (CDCl$_3$, ppm) |
|---|---|---|---|---|---|---|---|
| 374 | A | 88 | 115–116 | 1655 | 3090 | | |
| 375 | A | 70 | 95–96 | 1660 | 3120 | 3290 (υ≡C—H) 2110 (υC≡C) | |
| 376 | A | 83 | 115–116 | 1655 | 3120 | | |
| 377 | A | 89 | 87–88 | 1660 | 3130 | 1645 (υC=C) | |
| 378 | A | 79 | 97–98 | 1665 | 3120 | | |
| 379 | A | 60 | 114–115 | 1655 | 3110 | | |
| 380 | A | 81 | 71–72 | 1650 | 3140 | | |
| 381 | A | 51 | 97–98 | 1657 | 3120 | | |
| 382 | A | 83 | 98–99 | 1665 | 3100 | | |
| 383 | A | 93 | 122–123 (decomposed) | 1650 | 3120 | 3260 (υ≡C—H) | |
| 384 | A | 68 | 117–118 | 1660 | 3150 | | |
| 385 | A | 92 | liquid | 1660 | 3150 | | |
| 386 | A | 52 | 96–97 | 1660 | 3150 | | |
| 387 | A | 51 | 111–112 | 1650 | 3100 | | |
| 388 | A | 50 | 98.5–100.5 | 1657 | 3130 | | |
| 389 | A | 42 | 121–123 | 1648 | 3100 | | |
| 390 | A | 48 | 101–102 | 1655 | 3120 | | |
| 391 | A | 79 | 84–86 | 1658 | 3155 | | 3.90 (4H, d, J = 5 Hz), 5.02–5.40 (4H, m), 5.52–6.02 (2H, m), 7.00 (3H, s), 8.10 (1H, s), |
| 392 | A | 80 | 133–134 (decomposed) | 1650 | 3150 | 3290 (υ≡C—H) 2110 (υC≡C) | |
| 393 | A | 74 | 140–141 | 1665 | 3210 | | |
| 394 | A | 77 | 157–158 | 1655 | 3140 | | |
| 395 | A | 70 | 138–140 | 1662 | 3190 | | |
| 396 | A | 85 | 107–108 | 1650 | 3150 | | |
| 397 | A | 50 | 129–130.5 | 1650 | 3120 | | |
| 398 | A | 92 | 138.5–140.5 | 1650 | 3125 | | |
| 399 | A | 83 | 133–134 | 1660 | 3250 | | |
| 400 | A | 65 | 146–148 | 1645 | 3120 | | |
| 401 | A | 53 | 117–119 | 1650 | 3140 | | |
| 402 | A | 79 | 138–141 | 1653 | 3140 | | |
| 403 | A | 56 | 118–121 | 1655 | 3118 | | 0.88 (3H, t, J = 7 Hz), 1.20–1.90 (8H, m), 3.76 (2H, m), 3.96 (1H, s), and 6.99 (3H, s), 8.00 (1H, br.s) |
| 404 | A | 91 | 127–128 | 1650 | 3130 | | |
| 405 | A | 44 | 125–126 | 1658 | 3230 | | 1.60 (8H, m), 3.38 (4H, m), 6.98 (3H, m), 8.30 (1H, br.s) |
| 406 | A | 54 | 161–162 | 1653 | 3215 | | |
| 407 | A | 39 | 152–153 (decomposed) | 1650 | 3240 | | |
| 408 | A | 40 | 172–173 (decomposed) | 1658 | 3170 | | |
| 409 | C | 59 | 103–104 | 1650 | 3300, 3250 | | |
| 410 | A | 52 | 89–90 | 1655 | 3220 | | |
| 411 | A | 61 | 75–76 | 1660 | 3140 | | |
| 412 | A | 66 | 95–96 | 1656 | 3160 | 3295 (υ≡C—H) 2115 (υC≡C) | |
| 413 | A | 62 | 66–67 | 1661 | 3200 | | |
| 414 | A | 58 | 70–71 | 1660 | 3210 | 1639 (υC=C) | |
| 415 | A | 64 | 76–77 | 1660 | 3140 | | |
| 416 | A | 43 | 75–76 | 1660 | 3180 | | |
| 417 | A | 61 | 73–74 | 1665 | 3190 | | |
| 418 | A | 48 | 81–82 | 1657 | 3230 | | |
| 419 | A | 59 | 69–70 | 1665 | 3200 | 1650 (υC=C) | |
| 420 | A | 47 | 90–91 | 1660 | 3250 | 3290 (υ≡C—H) | |
| 421 | A | 66 | 127–128 | 1650 | 3210 | | |
| 422 | A | 79 | 92–93 | 1660 | 3190 | | |
| 423 | A | 60 | 109–110 | 1655 | 3180 | | |
| 424 | A | 60 | 76–77 | 1656 | 3180 | | |
| 425 | A | 63 | 95–96 | 1660 | 3140 | | |
| 426 | A | 50 | 58–60 | 1650 | 3140 | | 1.12 (6H, t, J = 7 Hz), 3.24 (4H, q, J = 7 Hz), 7.26 (4H, m), 8.28 (1H, br.s) |
| 427 | A | 50 | liquid | 1660 | 3200 | | 0.87 (3H, t, J = 8 Hz), 1.15 (3H, t, J = 7 Hz), 1.40–1.88 (2H, m), 3.26 (2H, q, J = 8 Hz), 3.34 (2H, q, J = 7 Hz), 7.27 (4H, m), 8.00 (1H, br.s) |
| 428 | A | 68 | 118–119 | 1660 | 3190 | | |

TABLE 4-continued

| Compound No. | Process | Yield (%) | Melting point (°C.) | IR spectrum ($cm^{-1}$) ν(C=O) | νN—H | Other characteristic absorption | $^1$H-MNR spectrum ($CDCl_3$, ppm) |
|---|---|---|---|---|---|---|---|
| 429 | A | 43 | 122-123 | 1655 | 3220 | | |
| 430 | A | 70 | 111-112 | 1660 | 3150 | | |
| 431 | A | 54 | 79-80.5 | 1650 | 3140 | | |
| 432 | A | 57 | 88-91 | 1655 | 3120 | | 0.97 (3H, d, J = 7 Hz), 1.10-1.96 (5H, m), 2.33-3.00 (2H, m), 3.83 (2H, m), 7.32 (4H, m), 7.96 (1H, br.s) |
| 433 | A | 40 | 107-109 | 1656 | 3260 | | |
| 434 | A | 45 | 126-127 | 1640 | 3160 | | |
| 435 | A | 45 | 111-113 | 1645 | 3160 | | |
| 436 | A | 57 | 103-104 | 1650 | 3210 | | |
| 437 | A | 54 | 121-122 | 1660 | 3240 | | |
| 438 | A | 50 | 100.5-101.5 | 1656 | 3280 | | |
| 439 | A | 54 | 154-155 | 1650 | 3270 | | |
| 440 | A | 43 | 150-151 (decomposed) | 1650 | 3300 | | |
| 441 | C | 80 | 125-126 | 1665 | 3300, 3090 | | |
| 442 | A | 30 | liquid | 1655 | 3170 | | |

EXAMPLE 330

3-(3,5-Dichlorophenoxy)-1,1-dimethyl urea trichloroacetate (Compound No. 443)

2.25 g (9 mmole) of 3-(3,5-dichlorophenoxy)-1,1-dimethyl urea was dissolved in 300 ml of diethyl ether, and then 50 ml of a diethyl ether solution containing 1.47 g (9 mmole) of trichloroacetic acid was added. The mixture was stirred at a temperature of from 25° to 30° C. for 24 hours. Diethyl ether was distilled off and 100 ml of hexane was added. The crystals thereby precipitated were collected by filtration and dried, whereby 3.52 g of the desired product was obtained as colorless acicular crystals (yield: 95%).

Melting point: 120°-121° C.

Elemental analysis: C: 32.43%, H: 2.76%, H, 6.74%. Calculated values as $C_{11}H_{11}Cl_5N_2O_4$ C: 32.03%, H: 2.69% N: 6.79%.

IR spectrum (KBr tablet, $cm^{-1}$): 3180, 2680−2000 (broad), 1755, 1620, 1580, 1503, 1395, 1250, 1095, 1070, 1017, 920, 855, 842, 832, 778, 703, 678, 672

$^1$H-NMR spectrum ($CDCl_3$) solution, ppm: 3.00 (6H, s), 7.03 (3H, s), 8.33 (2H, br. s)

EXAMPLE 331

3-(2,5-Dichlorophenoxy)-1,1-dimethyl urea trichloroacetate (Compound No. 444)

3-(2,5-dichlorophenoxy)-1,1-dimethyl urea was synthesized in the same manner as in example 330 except that 3-(2,5-dichlorophenoxy)-1,1-dimethyl urea was used instead of 3-(3,5-dichlorophenoxy)-1,1-dimethyl urea (yield: 54%).

Colorless acicular crystals

Melting point: 110°-112° C. (Decomposed)

Elemental analysis: C: 32.42%, H: 2.75%, H, 6.68%. Calculated values as $C_{11}H_{11}Cl_5N_2O_4$ C: 32.03%, H: 2.69%, N: 6.79%.

IR spectrum (KBr tablet, $cm^{-1}$): 3160, 2680-2000 (broad), 1760, 1628, 1580, 1505, 1470, 1394, 1257, 1240, 1095, 900, 866, 833, 815, 703, 677

$^1$H-NMR spectrum (CDCl solution, ppm): 3.00 (6H, s), 7.00 (1H, dd, J=8, 2 Hz), 7.24 (1H, d, J=8 Hz), 7.36 (1H, d, J=2 Hz), 8.52 (2H, br.s)

EXAMPLE 332

3-(3,5-Dichlorophenoxy)-1-isopropyl-1-methyl urea trichloroacetate (Compound No. 445)

3-(3,5-dichlorophenoxy)-1-isopropyl-1-methyl urea was synthesized in the same manner as in example 184 except that 3-(3,5-dichlorophenoxy)-1-isopropyl-1-methyl urea was used instead of 3-(3,5-dichlorophenoxy)-1,1-dimethyl urea (yield: 57%).

Slightly yellow powder

Melting point: 74°-75° C.

IR spectrum (KBr tablet, $cm^{-1}$): 3310, 3290, 3050, 2950, 1727, 1579, 1495, 1428, 1387, 1264, 1091, 843, 827, 702, 675

EXAMPLES 333-387, 398 AND 399

Compound Nos. 446 to 500 listed in Table 3 were synthesized in the same manner as the processes of examples 247 to 249. The results are shown in Table 5. Processes A, B and C in Table 5 correspond to the processes of Examples 247, 248 and 249, respectively.

TABLE 5

| Compound No. | Process | Yield (%) | Melting point (°C.) | IR spectrum ($cm^{-1}$) νC=O | νN—H | Other characteristic absorption | $^1$H-NMR spectrum ($CDCl_3$, ppm) |
|---|---|---|---|---|---|---|---|
| 446 | A | 65 | 91-93 | 1652 | 3130 | | |
| 447 | A | 41 | 112-114 | 1661 | 3200 | | |
| 448 | A | 32 | 136-139 (decomposed) | 1660 | 3210 | | |
| 449 | A | 40 | 105-107 | 1660 | 3180 | | |
| 450 | A | 22 | 122-124 | 1655 | 3210 | | |

TABLE 5-continued

| Compound No. | Process | Yield (%) | Melting point (°C.) | IR spectrum (cm⁻¹) νC═O | νN—H | Other characteristic absorption | $^1$H-NMR spectrum ($CDCl_3$, ppm) |
|---|---|---|---|---|---|---|---|
| | | | (decomposed) | | | | |
| 451 | A | 41 | 145-143 (decomposed) | 1655 | 3240 | | |
| 452 | A | 39 | 138-140 (decomposed) | 1662 | 3140 | | |
| 453 | A | 52 | 132-133 (decomposed) | 1650 | 3130 | | |
| 454 | A | 28 | 128-130 (decomposed) | 1655 | 3200 | | |
| 455 | A | 70 | 116-117 (decomposed) | 1652 | 3130 | | |
| 456 | A | 26 | 120-122 (decomposed) | 1650 | 3200 | | |
| 457 | A | 64 | 162-163 (decomposed) | 1650 | 3180 | | |
| 458 | A | 74 | 101-103 | 1655 | 3120 | | |
| 459 | A | 57 | 93-94 | 1655 | 3130 | | |
| 460 | A | 40 | 77-78 | 1660 | 3120 | | |
| 461 | A | 53 | 143-144 | 1650 | 3130 | | |
| 462 | A | 54 | 123-124 | 1655 | 3120 | | |
| 463 | A | 61 | 83-85 | 1652 | 3120 | | |
| 464 | A | 52 | 95-96 | 1660 | 3150 | | |
| 465 | A | 67 | 168-170 (decomposed) | 1660 | 3130 | | |
| 466 | A | 78 | 137-138 | 1660 | 3140 | | |
| 467 | A | 70 | 159-161 | 1655 | 3270 | | 1.0 (6H, s), 1.35 (4H, m) 3.38 (4H, m), 6.93-7.08 (3H, m), 9.58 (1H, s) |
| 468 | A | 81 | 95-96 | 1650 | 3130 | | |
| 469 | A | 75 | 134-135 | 1655 | 3140 | | |
| 470 | A | 62 | 50-52 | 1655 | 3170 | | |
| 471 | A | 40 | 123-124 | 1656 | 3190 | | |
| 472 | A | 49 | 104-106 | 1655 | 3120 | | |
| 473 | A | 50 | 101-105 | 1652 | 3120 | | 0.8-2.3 (12H, m), 2.7-3.0 (1H, m), 3.3-3.75 (3H, m), 7.06 (3H, s), 7.81 (1H, s) |
| 474 | A | 51 | 141-142 | 1655 | 3140 | | |
| 475 | A | 46 | 113-114 | 1650 | 3130 | | |
| 476 | A | 44 | 134-136 | 1655 | 3140 | | |
| 477 | A | 72 | 144-146 | 1675 | 3220 | | |
| 478 | A | 60 | 167-168 (decomposed) | 1650 | 3120 | | 1.3-1.9 (8H, m), 4.2-4.4 (2H, m, 7.0-7.1 (2H, m), 7.1-7.2 (1H, m), 7.8 (1H, s) |
| 479 | A | 47 | 168-170 (decomposed) | 1660 | 3190 | | |
| 480 | A | 56 | 154-155 | 1665 | 3200 | | |
| 481 | A | 31 | 159-161 (decomposed) | 1655 | 3200 | | 1.4-2.2 (9H, m), 2.40 (2H, d, J=2Hz), 4.08 (1H, m), 7.1 (3H, m), 7.45 (1H, s) |
| 482 | A | 64 | 163-165 (decomposed) | 1655 | 3190 | | |
| 483 | A | 60 | 118-119 | 1653 | 3130 | | |
| 484 | A | 60 | 53-55 | 1655 | 3150 | | |
| 485 | A | 85 | liquid | 1658 | 3190 | | |
| 486 | A | 62 | 103-104 | 1650 | 3230 | | |
| 487 | A | 40 | 78-79 | 1660 | 3180 | | |
| 488 | A | 38 | 67-68 | 1655 | 3150 | | |
| 489 | A | 38 | 67-68 | 1655 | 3150 | | |
| 490 | A | 47 | 106-107 | 1655 | 3140 | | |
| 491 | A | 73 | 114-115 | 1645 | 3130 | | |
| 492 | A | 65 | 97-98 | 1655 | 3130 | | |
| 493 | A | 73 | 153-155 (decomposed) | 1650 | 3250 | | |
| 494 | A | 53 | 89-90 | 1653 | 3270 | | |
| 495 | A | 79 | 100-101 | 1675 | 3280 | | |
| 496 | A | 64 | 145-147 | 1645 | 3200 | | |

TABLE 5-continued

| Compound No. | Process | Yield (%) | Melting point (°C.) | IR spectrum ($cm^{-1}$) νC=O | νN—H | Other characteristic absorption | $^1$H-NMR spectrum ($CDCl_3$, ppm) |
|---|---|---|---|---|---|---|---|
| | | | (decomposed) | | | | |
| 497 | A | 72 | 159-162 (decomposed) | 1660 | 3220 | | |
| 498 | A | 43 | 163-164 (decomposed) | 1655 | 3230 | | |
| 499 | A | 86 | 154-156 (decomposed) | 1650 | 3260 | | |
| 500 | A | 40 | 124-125 | 1665 | 3130 | | |

EXAMPLE 388

3-(2,5-Dichlorophenoxy)-1-methoxy-1-methyl urea (Compound No. 501)

4.5 g (25 mmol) of 2,5-dichlorophenoxyamine was dissolved in 10 ml of pyridine, and then 5.6 g (38 mmol) of methoxymethylcarbamoyl chloride was added. The mixture was stirred at a temperature of from 25° to 30° C. for 12 hours. After an addition of 200 ml of water, the reaction mixture was extracted with ethyl acetate. The extract was washed with a saturated sodium chloride aqueous solution, and dried over anhydrous magnesium sulfate. Ethyl acetate was distilled off, and precipitated crystals were recrystallized from ethyl acetate-hexane, whereby 4.8 g of the desired product was obtained (yield: 72%).

White powder

Melting point: 119°-120° C. (decomposed)

Mass spectrum (FD Method): m/Z 264 (Molecular ion peak)

IR spectrum (KBr tablet, $cm^{-1}$): 3200 ($\nu_{N-H}$), 1685 ($\nu_{C=O}$)

$^1$H-NMR spectrum ($CDCl_3$ solution, ppm): 3.18 (3H, s), 3.76 (3H, s), 6.84 (1H, dd, J=2, 8 Hz), 7.16-7.36 (2H, m), 8.76 (1H, br. s)

EXAMPLE 389

3-(2,5-Dichlorophenoxy)-1-methoxyethyl urea (Compound No. 502)

4.5 g (25 mmole) of 2,5-dichlorophenoxyamine was dissolved in 30 ml of toluene, and then 70 ml of an ethyl acetate solution containing 3.8 g (38 mmol) of 2-methoxyethyl cyanate was added. The mixture was stirred at a temperature of from 2° to 30° C. for 12 hours. After distilling off the solvent under reduced pressure, the mixture was purified by silica gel column chromatography (developer: ethyl acetate/hexane =1/4), and recrystallized from ethyl acetate-hexane, whereby 3.2 g of the desired product was obtained (yield: 48%).

Slightly yellow powder

Melting point: 116°-118° C. (decomposed)

IR spectrum (KBr tablet, $cm^{-1}$): 3360 ($\nu_{N-H}$), 3160 ($\nu_{N-H}$), 1670 ($\nu_{C=O}$)

EXAMPLES 390-397

Compound Nos. 503 to 510 listed in Table 3 were synthesized in the same manner as in Example 388. The results are shown in Table 6.

Compound Nos. 511 to 512 listed in Table 3 were synthesized in the same manner as in Example 389. The results are shown in Table 6.

TABLE 6

| Compound No. | Yield (%) | Melting point (°C) | IR spectrum ($cm^{-1}$) uN − H | uC = 0 |
|---|---|---|---|---|
| 503 | 63 | 98-99 | 3290 | 1702 |
| 504 | 34 | 73-75 | 3220 | 1680 |
| 505 | 53 | 111-113 (decomposed) | 3200 | 1665 |
| 506 | 42 | 82-84 | 3070 | 1653 |
| 507 | 36 | 75-76 | 3140 | 1653 |
| 508 | 77 | 103-104 | 3140 | 1655 |
| 509 | 94 | liquid | 3190 | 1660 |
| 510 | 79 | 78-79 | 3230 | 1660 |
| 511 | 75 | 122-125 (decomposed) | 3340, 3190 | 1650 |
| 512 | 77 | 138-140 (decomposed) | 3290, 3200 | 1660 |

Examples of formulating the herbicide of this invention will now be given. In the following Formulation Examples, all percentages are by weight.

Formulation Example 1B (granules)

The compound of this invention (10%), 2% of a sodium salt of lauryl sulfate, 5% of sodium lignin-sulfonate, 2% of carboxymethyl cellulose and 81% of clay were uniformly mixed and pulverized.

Water (20 parts) wa added to 80 parts of the resulting mixture and they were kneaded. The kneaded mixture was molded into particles having a size of 14 to 32 mesh by an extrusion granulator, and then dried to form granules.

Formulation Example 2B (dust)

A sodium salt of lauryl sulfate (2%), 5% of sodium ligninsulfonate, 2% of carboxymethyl cellulose and 91% of a clay/montmorillonite mixture were uniformly mixed and pulverized. The mixture (78 parts) was kneaded with 22 parts of water, and the kneaded mixture was processed into particles having a size of 14 to 32 mesh by an extrusion granulator and then dried to form a base composition for adsorption. Twenty parts of a solution of 20% of the compound of this invention in 80% of polyethylene glycol was adsorbed uniformly on 80 parts of the base composition to form a dust.

Formulation Example 3B (wettable powder)

The compound of the invention (10%), 85% of diatomaceous earth, 2% of sodium dinaphthylmethanedisulfonate and 3% of sodium ligninsulfonate were uniformly mixed and pulverized to form a wettable powder.

Formulation Example 4B (emulsifiable concentrate)

The compound of this invention (30%), 20% of cyclohexanone, 11% of polyoxyethylene alkylaryl ether, 4% of calcium alkylbenzenesulfonate and 35% of methyl-naphthalene were dissolved uniformly to form an emulsifiable concentrate.

Formulation Example 5B (dust)

The compound of this invention (4%), 5% of diatomaceous earth and 91% of clay were uniformly mixed and pulverized to form a dust.

The efficacy of the herbicide of this invention will now be illustrated by the following Test Examples.

Test Example 1C (herbicidal test by soil treatment in a paddy

Porcelain pots, 10 cm in diameter, were filled with paddy soil, and after puddling, seeds of barnyardgrass, umbrella plant, monochoria and bulrush were sown. The pots were then watered to a depth of 3 cm. On the next day, a wettable powder prepared in accordance with Formulation Example 3B was diluted with water and dropped onto the water surface (amount applied: 4 kg per hectare as the active ingredient). The plants were then grown in a greenhouse, and 30 days after the treatment, the herbicidal activity of the compound of the invention was examined according to the standards given in Table 1C. The results are shown in Table 2C.

TABLE 1C

| Index | Herbicidal efficacy and phytotoxicity |
|---|---|
| 5 | Withered |
| 4.5 | Herbicidal efficacy of 90 to 99% (phytotoxic) |
| 4 | Herbicidal efficacy of 80 to 89% (phytotoxic) |
| 3.5 | Herbicidal efficacy of 70 to 79% (phytotoxic) |
| 3 | Herbicidal efficacy of 60 to 69% (phytotoxic) |
| 2.5 | Herbicidal efficacy of 50 to 59% (phytotoxic) |
| 2 | Herbicidal efficacy of 40 to 49% (phytotoxic) |
| 1.5 | Herbicidal efficacy of 30 to 39% (phytotoxic) |
| 1 | Herbicidal efficacy of 20 to 29% (phytotoxic) |
| 0.5 | Herbicidal efficacy of 19 to 1% (phytotoxic) |
| 0 | No herbicidal efficacy (no phytotoxicity) |

TABLE 2C

| Test compound No. | Herbicidal effect: barnyard-grass | umbrella plant | monochoria | bulrush |
|---|---|---|---|---|
| 1 | 5 | 5 | 5 | 5 |
| 2 | 5 | 5 | 5 | 5 |
| 3 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 4 | 4 | 5 | 4 |
| 10 | 5 | 5 | 5 | 5 |

TABLE 2C-continued

| Test compound No. | Herbicidal effect: barnyard-grass | umbrella plant | monochoria | bulrush |
|---|---|---|---|---|
| 14 | 5 | 5 | 5 | 5 |
| 16 | 5 | 5 | 5 | 5 |
| 17 | 5 | 5 | 5 | 5 |
| 18 | 5 | 5 | 5 | 5 |
| 19 | 5 | 5 | 5 | 5 |
| 21 | 5 | 5 | 5 | 5 |
| 22 | 5 | 5 | 5 | 5 |
| 23 | 5 | 5 | 5 | 5 |
| 24 | 5 | 5 | 4 | 5 |
| 25 | 5 | 5 | 5 | 5 |
| 26 | 5 | 5 | 5 | 5 |
| 28 | 5 | 5 | 5 | 5 |
| 30 | 5 | 5 | 5 | 5 |
| 32 | 5 | 5 | 5 | 5 |
| 33 | 5 | 5 | 5 | 5 |
| 34 | 5 | 5 | 5 | 5 |
| 35 | 5 | 5 | 5 | 5 |
| 36 | 5 | 5 | 5 | 5 |
| 37 | 5 | 5 | 5 | 5 |
| 38 | 5 | 5 | 5 | 5 |
| 39 | 5 | 5 | 5 | 5 |
| 40 | 5 | 5 | 5 | 5 |
| 41 | 5 | 5 | 5 | 5 |
| 42 | 5 | 5 | 5 | 5 |
| 43 | 5 | 5 | 5 | 5 |
| 44 | 5 | 5 | 5 | 5 |
| 45 | 5 | 4 | 2 | 4 |
| 46 | 5 | 5 | 5 | 3 |
| 48 | 5 | 5 | 5 | 5 |
| 49 | 5 | 5 | 5 | 4 |
| 51 | 5 | 5 | 5 | 5 |
| 53 | 5 | 5 | 5 | 5 |
| 55 | 5 | 5 | 5 | 5 |
| 56 | 5 | 5 | 4 | 5 |
| 59 | 5 | 5 | 5 | 5 |
| 60 | 5 | 5 | 5 | 5 |
| 61 | 5 | 5 | 5 | 5 |
| 62 | 5 | 5 | 5 | 5 |
| 63 | 5 | 5 | 4 | 5 |
| 64 | 5 | 5 | 5 | 5 |
| 65 | 5 | 5 | 5 | 5 |
| 66 | 5 | 5 | 5 | 5 |
| 67 | 5 | 5 | 5 | 5 |
| 68 | 5 | 5 | 5 | 5 |
| 69 | 5 | 5 | 5 | 5 |
| 70 | 5 | 5 | 5 | 5 |
| 71 | 5 | 5 | 5 | 4 |
| 72 | 5 | 5 | 5 | 5 |
| 73 | 5 | 5 | 5 | 5 |
| 74 | 5 | 5 | 5 | 5 |
| 75 | 5 | 5 | 5 | 5 |
| 76 | 5 | 5 | 5 | 5 |
| 77 | 5 | 5 | 5 | 5 |
| 78 | 5 | 5 | 3 | 5 |
| 79 | 5 | 5 | 5 | 5 |
| Comparison* | 0 | 0 | 0 | 0 |
| Comparison** | 2 | 1 | 2 | 0 |

*

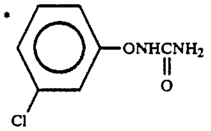

(The compound described in U.S. Pat. No. 3,332,975)

**

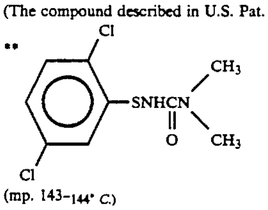

(mp. 143-144° C.)

Test Example 2C (selective herbicidal test between rice and barnyardgrass)

Paddy soil was filled into Wagner pots (1/5,000 a), and after puddling, seeds of barnyardgrass were sown and grown to the two-leaf stage in a greenhouse. The number of barnyardgrass plants in the two-leaf stage per pot was adjusted to 15. A predetermined amount of a wettable powder of each of the test compounds, prepared in accordance with Formulation Example 3B, was diluted with water, and dropped onto the water surface. Separately, rice seedlings in the two-leaf stage were transplanted in other Wagner pots (1/5,000 a). On the next day to the day of transplantation, the test compound was similarly dropped onto the water surface. After the treatment, the rice seedlings were grown for 30 days in a greenhouse. The herbicidal activity and phytotoxicity of the test compound were examined in accordance with the standards given in Table 1C. The results are shown in Table 3C.

TABLE 3C

| Test compound No. | Amount applied (kg/ha) | Herbicidal efficacy barnyardgrass in the 2-leaf stage | Phytotoxicity rice |
|---|---|---|---|
| 1 | 0.5 | 5 | 0 |
| | 0.25 | 5 | 0 |
| | 0.125 | 4 | 0 |
| 7 | 0.5 | 5 | 1 |
| | 0.25 | 5 | 0 |
| | 0.125 | 5 | 0 |
| 30 | 1 | 5 | 1 |
| | 0.5 | 5 | 0 |
| | 0.25 | 5 | 0 |
| 37 | 1 | 5 | 1 |
| | 0.5 | 4.5 | 0 |
| | 0.25 | 4 | 0 |
| 40 | 1 | 5 | 0 |
| | 0.5 | 5 | 0 |
| | 0.25 | 4.5 | 0 |
| 42 | 1 | 5 | 0 |
| | 0.5 | 4.5 | 0 |
| | 0.25 | 2.5 | 0 |
| 67 | 0.5 | 5 | 0 |
| | 0.25 | 5 | 0 |
| | 0.125 | 3.5 | 0 |

Test Example 3C (herbicidal test by soil treatment in an upland farm)

Upland farm soil was fixed in plastic pots (120 $cm^2$), and seeds of barnyardgrass, crabgrass, redroot pigweed and rice flatsedge were sown and covered with the soil. Each of the test compounds was formulated into a wettable powder in accordance with Formulation Example 3B. A predetermined amount of the wettable powder was diluted with water, and using a small-sized sprayer, was uniformly sprayed onto the soil surface at a rate of 1000 liters/hectare (the amount applied: 4 kg per hectare as the active ingredient). The plants were grown for 20 days in a greenhouse after the treatment, and the herbicidal efficacy and phytotoxicity were examined in accordance with the standards given in Table 1C. The results are shown in Table 4C.

TABLE 4C

| Test compound No. | Herbicidal efficacy barnyard-grass | crab-grass | redroot pigweed | rice flatsedge |
|---|---|---|---|---|
| 1 | 5 | 5 | 5 | 5 |
| 2 | 5 | 5 | 1 | 5 |
| 3 | 5 | 5 | 5 | 5 |
| 5 | 5 | 5 | 5 | 5 |
| 6 | 5 | 5 | 4 | 5 |
| 7 | 5 | 5 | 5 | 5 |
| 8 | 4 | 3 | 1 | 5 |
| 9 | 5 | 5 | 5 | 5 |
| 10 | 5 | 5 | 5 | 5 |
| 11 | 5 | 5 | 3 | 5 |
| 13 | 5 | 5 | 3 | 5 |
| 14 | 5 | 5 | 4 | 5 |
| 15 | 4 | 5 | 2.5 | 5 |
| 16 | 5 | 5 | 4 | 5 |
| 17 | 5 | 5 | 3 | 5 |
| 18 | 5 | 4 | 0 | 5 |
| 19 | 4 | 5 | 2 | 5 |
| 21 | 5 | 5 | 5 | 5 |
| 22 | 5 | 5 | 5 | 5 |
| 23 | 5 | 5 | 5 | 5 |
| 24 | 5 | 5 | 2 | 5 |
| 25 | 5 | 5 | 4 | 5 |
| 26 | 5 | 5 | 4 | 5 |
| 28 | 4 | 5 | 2 | 5 |
| 29 | 3 | 3 | 0 | 5 |
| 30 | 5 | 5 | 5 | 5 |
| 33 | 4 | 5 | 1 | 5 |
| 34 | 4 | 4 | 1 | 5 |
| 35 | 5 | 5 | 1 | 5 |
| 36 | 5 | 5 | 2 | 5 |
| 37 | 5 | 5 | 1 | 5 |
| 38 | 5 | 5 | 2 | 5 |
| 39 | 5 | 4 | 1 | 5 |
| 41 | 5 | 5 | 5 | 5 |
| 43 | 5 | 5 | 4 | 5 |
| 44 | 5 | 5 | 5 | 5 |
| 45 | 4 | 4 | 1 | 5 |
| 47 | 5 | 5 | 3 | 5 |
| 48 | 5 | 4 | 2 | 5 |
| 51 | 5 | 5 | 5 | 5 |
| 52 | 3 | 4 | 3 | 5 |
| 53 | 5 | 5 | 5 | 5 |
| 55 | 5 | 5 | 5 | 5 |
| 59 | 5 | 5 | 5 | 5 |
| 67 | 5 | 5 | 5 | 5 |
| 68 | 5 | 5 | 5 | 5 |
| 70 | 5 | 5 | 5 | 5 |
| 72 | 5 | 5 | 5 | 5 |
| 76 | 5 | 5 | 5 | 5 |
| 77 | 5 | 5 | 5 | 5 |
| 78 | 5 | 4 | 4 | 5 |
| 79 | 5 | 5 | 5 | 5 |

Test Example 4C (herbicidal efficacy and phytotoxicity by soil treatment in an upland farm)

Upland farm soil was filled in plastic vats (600 $cm^2$). Seeds of barnyardgrass, crabgrass, green foxtail, redroot pigweed, rice flatsedge, rice, wheat, corn, soybeans, cotton and sugar beet were sown and covered with the soil. Each of the test compounds was formulated into a wettable powder in accordance with Formulation Example 3B. A predetermined amount of the wettable powder was diluted with water and uniformly sprayed onto the soil surface by a small-sized sprayer at a rate of 1000 liters per hectare. The plants were grown in a greenhouse for 30 days after the treatment. The herbicidal efficacy and phytotoxicity were examined in accordance with the standards given in Table 1C. The results are shown in Table 5C.

TABLE 5C

| Test compound No. | Amount applied (kg/ha) | Herbicidal efficacy barnyard-grass | crab-grass | green foxtail | redroot pigweed | rice flats-edge | Phytotoxicity rice | wheat | corn | soy beans | cotton | sugar beet |
|---|---|---|---|---|---|---|---|---|---|---|---|---|
| 2 | 2 | 5 | 5 | 5 | 1 | 5 | 0 | 0 | 0 | 0 | 0 | 0 |
| | 1 | 5 | 5 | 5 | 0 | 5 | 0 | 0 | 0 | 0 | 0 | 0 |
| | 0.5 | 4.5 | 5 | 4 | 0 | 5 | 0 | 0 | 0 | 0 | 0 | 0 |
| 7 | 2 | 5 | 5 | 5 | 5 | 5 | 2 | 0.5 | 4 | 1 | 0 | 2 |
| | 1 | 5 | 5 | 5 | 5 | 5 | 2 | 0.5 | 4 | 0 | 0 | 1 |
| | 0.5 | 5 | 5 | 5 | 4 | 5 | 0.5 | 0 | 2 | 0 | 0 | 1 |
| 21 | 2 | 5 | 5 | 5 | 5 | 5 | 4.5 | 2.5 | 3.5 | 0 | 0 | 2 |
| | 1 | 5 | 5 | 5 | 5 | 5 | 2 | 2 | 1 | 0 | 0 | 0 |
| | 0.5 | 4.5 | 5 | 5 | 4 | 5 | 1 | 1 | 0 | 0 | 0 | 0 |
| 22 | 2 | 5 | 5 | 5 | 5 | 5 | 2 | 0.5 | 2.5 | 0 | 0 | 0 |
| | 1 | 5 | 5 | 5 | 5 | 5 | 1 | 0 | 2 | 0 | 0 | 0 |
| | 0.5 | 4.5 | 5 | 5 | 2 | 5 | 0 | 0 | 0.5 | 0 | 0 | 0 |
| 43 | 2 | 5 | 5 | 5 | 5 | 5 | 3 | 1.5 | 3 | 0 | 0 | 0 |
| | 1 | 5 | 5 | 5 | 5 | 5 | 1 | 0 | 3 | 0 | 0 | 0 |
| | 0.5 | 5 | 5 | 4 | 5 | 5 | 0.5 | 0 | 0 | 0 | 0 | 0 |

Test Example 5C (herbicidal test by foliar treatment in an upland farm)

Upland farm soil was filled in plastic pots (120 $cm^2$), and seeds of barnyardgrass, crabgrass, redroot pigweed and rice flatsedge were sown and grown in a greenhouse until the barnyardgrass reached a three-leaf stage. Each of the test compounds was formulated into a wettable powder in accordance with Formulation Example 3B. The wettable powder in an amount equivalent to 4 kg per hectare as the active ingredient was diluted with water, and sprayed over the foliage of the plants from above by a small-sized sprayer at a rate of 1000 liters per hectare. After the spraying, the plants were grown in a greenhouse for 20 days. The herbicidal efficacy was examined in accordance with the standards given in Table 1C, and the results are shown in Table 6C.

TABLE 6C

| Test compound No. | Herbicidal efficacy barnyard-grass | crab-grass | redroot pigweed | rice flatsedge |
|---|---|---|---|---|
| 1 | 4 | 5 | 0 | 4 |
| 2 | 4 | 5 | 2 | 5 |
| 3 | 5 | 5 | 3 | 5 |
| 7 | 5 | 5 | 2 | 3 |
| 9 | 5 | 5 | 4 | 5 |
| 11 | 4 | 3 | 1 | 5 |
| 17 | 4 | 4 | 4 | 5 |
| 18 | 3 | 3 | 3 | 5 |
| 19 | 4 | 4 | 5 | 5 |
| 21 | 5 | 5 | 4 | 5 |
| 22 | 5 | 5 | 3 | 5 |
| 23 | 5 | 5 | 4 | 5 |
| 24 | 4 | 4 | 4 | 5 |
| 30 | 4 | 4 | 1 | 4 |
| 35 | 4 | 3 | 0 | 5 |
| 36 | 4 | 3 | 2 | 4 |
| 37 | 4 | 2 | 1 | 4 |
| 41 | 4 | 4 | 2 | 5 |
| 43 | 4 | 4 | 2 | 5 |
| 44 | 5 | 5 | 4 | 5 |
| 47 | 3 | 3 | 5 | 5 |
| 59 | 5 | 4 | 2 | 5 |
| 67 | 5 | 4 | 3 | 4 |
| 68 | 5 | 4 | 4 | 4 |
| 70 | 5 | 5 | 2 | 5 |
| 72 | 5 | 4 | 3 | 5 |
| 74 | 5 | 4 | 2 | 5 |
| 76 | 5 | 4 | 3 | 5 |
| 77 | 4 | 4 | 2 | 4 |
| 79 | 5 | 4 | 1 | 5 |

Test Example 6C (herbicidal test by soil treatment in a paddy)

Porcelain pots, 10 cm in diameter, were filled with paddy soil, and after puddling, seeds of barnyardgrass, umbrella plant, monochoria and bulrush were sown. The pots were then watered to a depth of 3 cm. On the next day, a wettable powder prepared in accordance with Formulation Example 3B was diluted with water and dropped onto the water surface (amount applied: 4 kg per hectare as the active ingredient). The plants were then grown in a greenhouse, and 30 days after the treatment, the herbicidal activity of the compound of the invention was examined according to the standards given in Table 1C. The results are shown in Table 7C.

TABLE 7C

| Test Compound No. | Herbicidal efficacy barn yard-grass | umbrella plant | monochoria | bulrush |
|---|---|---|---|---|
| 4 | 5 | 5 | 5 | 5 |
| 82 | 5 | 5 | 5 | 5 |
| 83 | 5 | 5 | 5 | 4 |
| 84 | 5 | 5 | 5 | 5 |

Test Example 7C (herbicidal test by soil treatment in an upland farm)

Upland farm soil was filled in plastic pots (120 $cm^2$), and seeds of barnyard grass, crabgrass, redroot pigweed and rice flatsedge were sown and covered with the soil. Each of the test compounds was formulated into a wettable powder in accordance with formulation Example 3B. A predetermined amount of the wettable powder was diluted with water, and by a small-sized sprayer, uniformly sprayed onto the soil surface at a rate of 1000 liters/hectare (the amount applied: 4 kg per hectare as the active ingredient). The plants were grown for 20 days in a greenhouse after the treatment, and the herbicidal efficacy and phytotoxicity were examined in accordance with the standards given in Table 1C. The results are shown in Table 8C.

TABLE 8C

| Test Compound No. | Herbicidal efficacy barnyard-grass | crab-grass | redroot pigweed | rice flats-edge |
|---|---|---|---|---|
| 4 | 5 | 5 | 4 | 5 |
| 82 | 5 | 5 | 5 | 5 |
| 83 | 5 | 2 | 5 | 5 |
| 84 | 5 | 5 | 5 | 5 |

Test Example 8C (herbicidal efficacy and phytotoxicity by soil treatment in an upland farm)

Upland farm soil was filled in plastic vats (600 $cm^2$). Seeds of barnyardgrass, crabgrass, green foxtail, redroot pigweed, rice flatsedge, rice, wheat, corn, soybeans, cotton and sugar beet were sown and covered with the soil. Each of the test compounds was formulated into a wettable powder in accordance with Formulation Example 3B. A predetermined amount of the wettable powder was diluted with water and uniformly sprayed onto the soil surface by a small-sized sprayer at a rate of 1000 liters per hectare. The plants were grown in a greenhouse for 30 days after the treatment. The herbicidal efficacy and phytotoxicity were examined in accordance with the standards given in Table 1C. The results are shown in Table 9C.

TABLE 9C

| Test Compound No. | Amount applied (kg/ha) | Herbicidal efficacy barnyard-grass | crab-grass | green foxtail | redroot pigweed | rice flatsedge | Phytotoxicity rice | wheat | corn | soy beans | cotton | sugar beet |
|---|---|---|---|---|---|---|---|---|---|---|---|---|
| 84 | 1 | 5 | 5 | 5 | 5 | 5 | 3 | 5 | 5 | 1.5 | 3.5 | 2 |
| | 0.5 | 5 | 5 | 5 | 5 | 5 | 2 | 3 | 2 | 0.5 | 1.5 | 1 |
| | 0.25 | 5 | 5 | 5 | 4 | 5 | 1 | 0.5 | 0 | 0 | 0 | 1 |

Test Example 9C (herbicidal test by soil treatment in a paddy)

Porcelain pots, 10 cm in diameter, were filled with paddy soil, and after puddling, seeds of barnyardgrass, umbrella plant, monochoria and bulrush were sown. The pots were then watered to a depth of 3 cm. On the next day a wettable powder prepared in accordance with Formulation Example 3B was diluted with water and dropped onto the water surface (amount applied: 4 kg per hectare as the active ingredient). The plants were then grown in a greenhouse, and 30 days after the treatment, the herbicidal activity of the compound of the invention was examined according to the standards given in Table 1C. The results are shown in Table 10C.

TABLE 10C

| Test Compound No. | Herbicidal efficacy barn-yard-grass | umbrella plant | monochoria | bulrush |
|---|---|---|---|---|
| 85 | 0 | 0 | 5 | 0 |
| 86 | 5 | 5 | 5 | 5 |
| 87 | 5 | 5 | 5 | 5 |
| 88 | 5 | 5 | 5 | 5 |
| 90 | 1 | 5 | 5 | 4 |
| 91 | 5 | 5 | 5 | 5 |

TABLE 10C-continued

| Test Compound No. | Herbicidal efficacy barn-yard-grass | umbrella plant | monochoria | bulrush |
|---|---|---|---|---|
| 93 | 4 | 5 | 4 | 4 |

Test Example 10C (herbicidal test by soil treatment in an upland farm)

Upland farm soil was filled in plastic pots (120 $cm^2$), and seeds of barnyardgrass, crabgrass, redroot pigweed and rice flatsedge were sown and covered with the soil. Each of the test compounds was formulated into a wettable powder in accordance with Formulation Example 3B. A predetermined amount of the wettable powder was diluted with water, and by a small-sized sprayer, uniformly sprayed onto the soil surface at a rate of 1000 liters/hectare (the amount applied: 4 kg per hectare as the active ingredient). The plants were grown for 20 days in a greenhouse after the treatment, and the herbicidal efficacy and phytotoxicity were examined in accordance with the standards given in Table 1C. The results are shown in Table 11C.

TABLE 11C

| Test Compound No. | Herbicidal efficacy barn-yard-grass | crab-grass | redroot pigweed | rice flats edge |
|---|---|---|---|---|
| 86 | 5 | 5 | 4 | 5 |
| 87 | 5 | 5 | 5 | 5 |
| 88 | 5 | 5 | 5 | 5 |
| 89 | 0 | 1 | 0 | 5 |
| 90 | 3 | 5 | 5 | 5 |
| 91 | 5 | 5 | 5 | 5 |
| 92 | 0 | 0 | 2 | 5 |
| 93 | 5 | 5 | 5 | 5 |

Test Example 11C (herbicidal efficacy and phytotoxicity by soil treatment in an upland farm)

Upland farm soil was filled in plastic vats (600 $cm^2$). Seeds of barnyardgrass, crabgrass, green foxtail, redroot pigweed, rice flatsedge, rice, wheat, corn, soybeans, cotton and sugar beet were sown and covered with the soil. Each of the test compounds was formulated into a wettable powder in accordance with formulation Example 3B. A predetermined amount of the wettable powder was diluted with water and uniformly sprayed onto the soil surface by a small-sized sprayer at a rate of 1000 liters per hectare. The plants were grown in a greenhouse for 30 days after the treatment. The herbicidal efficacy and phytotoxicity were examined in accordance with the standards given in Table 1C. The results are shown in Table 12C.

TABLE 12

| Test Compound No. | Amount applied (kg/ha) | Herbicidal efficacy: barnyard-grass | crabgrass | green foxtail | redroot pigweed | rice flatsedge | Phytotoxicity: rice | wheat | corn | soybeans | cotton | sugar beet |
|---|---|---|---|---|---|---|---|---|---|---|---|---|
| 86 | 1 | 5 | 5 | 5 | 5 | 5 | 4.5 | 1 | 4.5 | 0.5 | 4 | 2 |
| | 0.5 | 5 | 5 | 5 | 5 | 5 | 4.5 | 0.5 | 4.5 | 0 | 4 | 1.5 |
| | 0.25 | 5 | 5 | 5 | 4.5 | 5 | 4 | 0 | 4.5 | 0 | 4 | 1.5 |
| 87 | 1 | 5 | 5 | 5 | 5 | 5 | 0 | 0.5 | 1.5 | 0 | 1 | 2 |
| | 0.5 | 5 | 5 | 5 | 5 | 5 | 0 | 0 | 1 | 0 | 0 | 1 |
| | 0.25 | 5 | 5 | 5 | 5 | 5 | 0 | 0 | 0 | 0 | 0 | 0 |
| 88 | 1 | 5 | 5 | 5 | 4.5 | 5 | 0.5 | 0.5 | 2 | 1 | 0 | 5 |
| | 0.5 | 5 | 5 | 5 | 3 | 5 | 0 | 0 | 2 | 0.5 | 0 | 2 |
| | 0.25 | 5 | 5 | 5 | 2 | 5 | 0 | 0 | 1.5 | 0.5 | 0 | 0 |
| 93 | 2 | 5 | 5 | 5 | 2 | 5 | 0 | 0 | 0 | 0 | 0 | 0 |
| | 1 | 5 | 5 | 5 | 0 | 5 | 0 | 0 | 0 | 0 | 0 | 0 |
| | 0.5 | 3 | 4 | 4.5 | 0 | 4.5 | 0 | 0 | 0 | 0 | 0 | 0 |
| Comparison* | 1 | 2.5 | 4.5 | 4 | 5 | 5 | 1 | 1 | 2 | 1 | 0 | 5 |
| | 0.5 | 1 | 3.5 | 3 | 5 | 5 | 0.5 | 0.5 | 1.5 | 0 | 0 | 5 |
| | 0.25 | 0 | 1 | 1 | 4 | 1 | 0 | 0 | 0 | 0 | 0 | 4.5 |

*fluomethuron

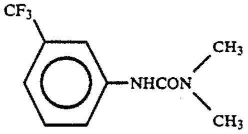

TABLE 2C (continued)

| Test Compound No. | Herbicidal effect: barnyard-grass | umbrella plant | monochoria | bulrush |
|---|---|---|---|---|
| 94 | 5 | 5 | 5 | 5 |
| 95 | 5 | 5 | 5 | 5 |
| 96 | 5 | 5 | 5 | 5 |
| 97 | 5 | 5 | 5 | 5 |
| 98 | 5 | 5 | 5 | 5 |
| 99 | 5 | 5 | 5 | 5 |
| 100 | 5 | 5 | 5 | 5 |
| 101 | 5 | 5 | 5 | 5 |
| 102 | 5 | 4.5 | 5 | 5 |
| 103 | 5 | 5 | 5 | 5 |
| 104 | 5 | 5 | 5 | 5 |
| 105 | 5 | 5 | 5 | 5 |
| 106 | 5 | 5 | 5 | 5 |
| 107 | 5 | 5 | 5 | 5 |
| 108 | 5 | 5 | 5 | 5 |
| 109 | 5 | 5 | 5 | 5 |
| 110 | 5 | 5 | 5 | 5 |
| 111 | 5 | 5 | 5 | 5 |
| 112 | 5 | 5 | 5 | 5 |
| 113 | 5 | 5 | 5 | 5 |
| 114 | 5 | 5 | 5 | 5 |
| 115 | 5 | 5 | 5 | 5 |
| 116 | 5 | 5 | 5 | 5 |
| 117 | 5 | 5 | 5 | 5 |
| 118 | 5 | 5 | 5 | 5 |
| 119 | 5 | 5 | 5 | 5 |
| 120 | 5 | 5 | 5 | 5 |
| 121 | 5 | 5 | 5 | 5 |
| 122 | 5 | 5 | 5 | 5 |
| 123 | 5 | 5 | 5 | 5 |
| 124 | 5 | 5 | 5 | 5 |
| 125 | 5 | 5 | 5 | 5 |
| 126 | 5 | 5 | 5 | 5 |
| 127 | 5 | 5 | 5 | 5 |
| 128 | 5 | 5 | 5 | 5 |
| 129 | 5 | 5 | 5 | 5 |
| 130 | 5 | 5 | 5 | 5 |
| 131 | 5 | 5 | 5 | 5 |
| 132 | 5 | 5 | 5 | 5 |
| 133 | 5 | 5 | 5 | 5 |
| 134 | 5 | 5 | 5 | 5 |
| 135 | 5 | 5 | 5 | 5 |
| 136 | 5 | 5 | 5 | 5 |
| 137 | 5 | 5 | 5 | 5 |
| 138 | 5 | 5 | 5 | 5 |
| 139 | 5 | 5 | 5 | 5 |
| 140 | 5 | 5 | 5 | 5 |
| 141 | 5 | 5 | 5 | 5 |

TABLE 2C (continued)-continued

| Test Compound No. | Herbicidal effect: barnyard-grass | umbrella plant | monochoria | bulrush |
|---|---|---|---|---|
| 142 | 5 | 5 | 5 | 5 |
| 143 | 5 | 5 | 5 | 5 |
| 144 | 5 | 5 | 5 | 5 |
| 145 | 5 | 5 | 5 | 5 |
| 146 | 5 | 5 | 5 | 5 |
| 147 | 5 | 5 | 5 | 5 |
| 148 | 5 | 5 | 5 | 5 |
| 149 | 5 | 5 | 5 | 5 |
| 150 | 5 | 5 | 5 | 5 |
| 151 | 5 | 5 | 5 | 5 |
| 152 | 5 | 5 | 5 | 5 |
| 153 | 5 | 5 | 5 | 5 |
| 154 | 5 | 5 | 5 | 5 |
| 155 | 5 | 5 | 5 | 5 |
| 156 | 5 | 5 | 5 | 5 |
| 157 | 5 | 5 | 5 | 5 |
| 158 | 5 | 5 | 5 | 5 |
| 159 | 5 | 5 | 5 | 5 |
| 160 | 5 | 5 | 5 | 5 |
| 161 | 5 | 5 | 5 | 5 |
| 162 | 5 | 5 | 5 | 5 |
| 163 | 5 | 5 | 5 | 4 |
| 164 | 5 | 5 | 5 | 5 |
| 165 | 5 | 5 | 5 | 2.5 |
| 166 | 5 | 5 | 5 | 5 |
| 167 | 5 | 5 | 5 | 5 |
| 168 | 5 | 5 | 5 | 5 |
| 169 | 5 | 5 | 5 | 5 |
| 170 | 5 | 5 | 5 | 5 |
| 171 | 5 | 5 | 5 | 5 |
| 172 | 5 | 5 | 5 | 5 |
| 173 | 5 | 5 | 5 | 5 |
| 174 | 5 | 5 | 5 | 5 |
| Comparison** | 0 | 0 | 0 | 0 |

*

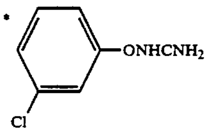

(the compound described in U.S. Pat. No. 3,332,975)

Test Example 2C (selective herbicidal test between rice and barnyardgrass)

Paddy soil was filled into Wagner pots (1/5,000 a), and after puddling, seeds of barnyardgrass were sown and grown to the two-leaf stage in a greenhouse. The number of barnyardgrass plants in the two-leaf stage per pot was adjusted to 15. A predetermined amount of a wettable powder of each of the test compounds, prepared in accordance with Formulation Example 3B, was diluted with water, and dropped onto the water surface. Separately, rice seedlings in the two-leaf stage were transplanted in other Wagner pots (1/5,000 a). On the next day to the day of transplantation, the test compound was similarly dropped onto the water surface. After the treatment, the rice seedlings were grown for 30 days in a greenhouse. The herbicidal activity and phytotoxicity of the test compound were examined in accordance with the standards given in Table 1C. The results are shown in Table 3C.

TABLE 3C

| Test Compound No. | Amount applied (kg/ha) | Herbicidal efficacy barnyardgrass in the 2-leaf stage | Phytotoxicity rice |
|---|---|---|---|
| 95 | 0.5 | 5 | 1 |
| | 0.25 | 5 | 1 |
| | 0.125 | 5 | 0 |
| 96 | 0.5 | 5 | 2 |
| | 0.25 | 5 | 0 |
| | 0.125 | 5 | 0 |
| 98 | 0.5 | 5 | 1 |
| | 0.25 | 5 | 1 |
| | 0.12 | 5 | 0 |
| 100 | 1 | 5 | 0 |
| | 0.5 | 5 | 0 |
| | 0.25 | 3.5 | 0 |
| 106 | 0.5 | 5 | 2 |
| | 0.25 | 5 | 0 |
| | 0.125 | 5 | 0 |
| 114 | 0.5 | 5 | 0 |
| | 0.25 | 5 | 0 |
| | 0.125 | 5 | 0 |
| 116 | 0.5 | 5 | 0 |
| | 0.25 | 5 | 0 |
| | 0.125 | 5 | 0 |
| 126 | 0.5 | 5 | 0 |
| | 0.25 | 5 | 0 |
| | 0.125 | 5 | 0 |
| 127 | 0.5 | 5 | 3 |
| | 0.25 | 5 | 1 |
| | 0.125 | 5 | 0 |
| 132 | 0.5 | 5 | 1 |
| | 0.25 | 5 | 0 |
| | 0.125 | 5 | 0 |
| 133 | 0.5 | 5 | 1 |
| | 0.25 | 5 | 0 |
| | 0.125 | 5 | 0 |
| 135 | 0.5 | 5 | 2 |
| | 0.25 | 5 | 1 |
| | 0.125 | 5 | 0 |
| 136 | 0.5 | 5 | 1 |
| | 0.25 | 5 | 1 |
| | 0.125 | 5 | 0 |
| 138 | 0.5 | 5 | 0 |
| | 0.25 | 5 | 0 |
| | 0.125 | 5 | 0 |
| 139 | 0.5 | 5 | 1 |
| | 0.25 | 5 | 1 |
| | 0.125 | 5 | 0 |
| 140 | 0.5 | 5 | 0 |
| | 0.25 | 5 | 0 |
| | 0.125 | 5 | 0 |
| 146 | 0.5 | 5 | 2 |
| | 0.25 | 5 | 1 |
| | 0.125 | 5 | 1 |
| 147 | 0.5 | 5 | 1 |
| | 0.25 | 5 | 0 |
| | 0.125 | 5 | 0 |
| 148 | 0.5 | 5 | 0 |
| | 0.25 | 5 | 0 |

TABLE 3C -continued

| Test Compound No. | Amount applied (kg/ha) | Herbicidal efficacy barnyardgrass in the 2-leaf stage | Phytotoxicity rice |
|---|---|---|---|
| | 0.125 | 5 | 0 |
| 149 | 0.5 | 5 | 0 |
| | 0.25 | 5 | 0 |
| | 0.125 | 5 | 0 |
| 150 | 0.5 | 5 | 1 |
| | 0.25 | 5 | 1 |
| | 0.125 | 5 | 0 |
| 151 | 0.5 | 5 | 0 |
| | 0.25 | 5 | 0 |
| | 0.125 | 5 | 0 |
| 152 | 0.5 | 5 | 1 |
| | 0.25 | 5 | 1 |
| | 0.125 | 5 | 1 |
| 153 | 0.5 | 5 | 2 |
| | 0.25 | 5 | 0 |
| | 0.125 | 5 | 0 |
| 154 | 0.5 | 5 | 2 |
| | 0.25 | 5 | 0 |
| | 0.125 | 5 | 0 |
| 155 | 0.5 | 5 | 2 |
| | 0.25 | 5 | 1 |
| | 0.125 | 5 | 1 |
| 158 | 0.5 | 5 | 3 |
| | 0.25 | 5 | 2 |
| | 0.125 | 5 | 0 |
| 160 | 0.5 | 5 | 3 |
| | 0.25 | 5 | 3 |
| | 0.125 | 5 | 1 |
| 161 | 0.5 | 5 | 3 |
| | 0.25 | 5 | 1 |
| | 0.125 | 5 | 1 |
| 169 | 0.5 | 5 | 1 |
| | 0.25 | 5 | 1 |
| | 0.125 | 2 | 0 |

Test Example 3C (herbicidal test by soil treatment in an upland farm)

Upland farm soil was filled in plastic pots (120 $cm^2$), and seeds of barnyardgrass, crabgrass, redroot pigweed and rice flatsedge were sown and covered with the soil. Each of the test compounds was formulated into a wettable powder in accordance with Formulation Example 3B. A predetermined amount of the wettable powder was diluted with water, and, using a small-sized sprayer, was uniformly sprayed onto the soil surface at a rate of 1000 liters/hectare (the amount applied: 4 kg per hectare as the active ingredient). The plants were grown for 20 days in a greenhouse after the treatment, and the herbicidal efficacy and phytotoxicity were examined in accordance with the standards given in Table 1C. The results are shown in Table 4C.

TABLE C

| Test Compound No. | Herbicidal effect barnyard-grass | crab-grass | redroot pigweed | rice flatsedge |
|---|---|---|---|---|
| 94 | 5 | 5 | 5 | 5 |
| 95 | 5 | 5 | 5 | 5 |
| 96 | 5 | 5 | 5 | 5 |
| 97 | 5 | 5 | 5 | 5 |
| 98 | 5 | 5 | 5 | 5 |
| 99 | 5 | 5 | 5 | 5 |
| 100 | 5 | 5 | 5 | 5 |
| 101 | 5 | 5 | 5 | 5 |
| 102 | 5 | 5 | 5 | 5 |
| 104 | 5 | 4 | 5 | 5 |
| 105 | 5 | 5 | 5 | 5 |
| 106 | 5 | 5 | 5 | 5 |

TABLE C -continued

| Test Compound No. | Herbicidal effect barnyard-grass | crab-grass | redroot pigweed | rice flatsedge |
|---|---|---|---|---|
| 107 | 5 | 5 | 5 | 5 |
| 108 | 5 | 5 | 5 | 5 |
| 109 | 5 | 5 | 5 | 5 |
| 110 | 5 | 5 | 5 | 5 |
| 111 | 5 | 5 | 5 | 5 |
| 112 | 5 | 5 | 5 | 5 |
| 113 | 5 | 4 | 2 | 5 |
| 114 | 5 | 5 | 5 | 5 |
| 115 | 5 | 5 | 5 | 5 |
| 116 | 5 | 5 | 1.5 | 5 |
| 117 | 5 | 5 | 5 | 5 |
| 118 | 5 | 5 | 3 | 5 |
| 119 | 5 | 5 | 0 | 5 |
| 120 | 5 | 4 | 0 | 5 |
| 122 | 5 | 5 | 4 | 5 |
| 123 | 5 | 5 | 5 | 5 |
| 124 | 5 | 5 | 2 | 5 |
| 125 | 4 | 5 | 4 | 5 |
| 126 | 5 | 5 | 5 | 5 |
| 127 | 5 | 5 | 5 | 5 |
| 129 | 3 | 5 | 0 | 5 |
| 130 | 5 | 5 | 1 | 5 |
| 132 | 5 | 5 | 4 | 5 |
| 133 | 5 | 5 | 4 | 5 |
| 135 | 5 | 5 | 5 | 5 |
| 136 | 5 | 5 | 5 | 5 |
| 138 | 5 | 5 | 2 | 5 |
| 139 | 5 | 5 | 5 | 5 |
| 140 | 5 | 5 | 5 | 5 |
| 142 | 5 | 5 | 5 | 5 |
| 143 | 5 | 5 | 2 | 5 |
| 144 | 5 | 3 | 1 | 5 |
| 145 | 5 | 5 | 2 | 5 |
| 146 | 5 | 5 | 5 | 5 |
| 147 | 5 | 5 | 5 | 5 |
| 148 | 5 | 5 | 5 | 5 |
| 149 | 5 | 5 | 3 | 5 |
| 150 | 5 | 5 | 5 | 5 |
| 151 | 5 | 5 | 5 | 5 |
| 152 | 5 | 5 | 5 | 5 |
| 153 | 5 | 5 | 5 | 5 |

TABLE C -continued

| Test Compound No. | Herbicidal effect barnyard-grass | crab-grass | redroot pigweed | rice flatsedge |
|---|---|---|---|---|
| 154 | 5 | 5 | 5 | 5 |
| 155 | 5 | 5 | 5 | 5 |
| 156 | 5 | 5 | 5 | 5 |
| 157 | 5 | 5 | 5 | 5 |
| 158 | 5 | 5 | 5 | 5 |
| 159 | 5 | 5 | 5 | 5 |
| 160 | 5 | 5 | 5 | 5 |
| 161 | 5 | 5 | 5 | 5 |
| 162 | 5 | 5 | 1 | 5 |
| 163 | 5 | 5 | 3 | 5 |
| 164 | 5 | 5 | 0 | 5 |
| 165 | 5 | 5 | 0 | 5 |
| 166 | 5 | 5 | 0 | 5 |
| 167 | 2 | 5 | 0 | 5 |
| 168 | 5 | 3 | 0 | 5 |
| 169 | 5 | 5 | 5 | 5 |
| 170 | 5 | 5 | 5 | 5 |
| 174 | 5 | 5 | 3 | 5 |

Test Example 4C (herbicidal efficacy and phytotoxicity by soil treatment in an upland farm)

Upland farm soil was filled in plastic vats (600 $cm^2$). Seeds of barnyardgrass, crabgrass, green foxtail, redroot pigweed, rice flatsedge, rice, wheat, corn, soybeans, cotton and sugarbeet were sown and covered with the soil. Each of the test compounds was formulated into a wettable powder in accordance with Formulation Example 3B. A predetermined amount of the wettable powder was diluted with water and uniformly sprayed onto the soil surface by a small-sized sprayer at a rate of 1000 liters per hectare. The plants were grown in a greenhouse for 30 days after the treatment. The herbicidal efficacy and phytotoxicity were examined in accordance with the standards given in Table 1C. The results are shown in Table 5C.

TABLE 5C

| Test Compound No. | Amount applied (kg/ha) | Herbicidal efficacy barnyard-grass | crab-grass | green foxtail | redroot pigweed | rice flatsedge | Phytotoxicity rice | wheat | corn | soy-beans | cotton | sugar beet |
|---|---|---|---|---|---|---|---|---|---|---|---|---|
| 95 | 2 | 5 | 5 | 5 | 5 | 5 | 0.5 | 1.5 | 3.5 | 0 | 0 | 1 |
| | 1 | 5 | 5 | 5 | 5 | 5 | 0 | 0.5 | 2.5 | 0 | 0 | 0.5 |
| | 0.5 | 4.5 | 5 | 5 | 5 | 5 | 0 | 0 | 2.5 | 0 | 0 | 0.5 |
| 96 | 2 | 5 | 5 | 5 | 5 | 5 | 1 | 3 | 5 | 0 | 0 | 2 |
| | 1 | 5 | 5 | 5 | 5 | 5 | 1 | 1 | 4 | 0 | 0 | 2 |
| | 0.5 | 5 | 5 | 1 | 5 | 5 | 0 | 0 | 2 | 0 | 0 | 2 |
| 98 | 2 | 5 | 5 | | 5 | 5 | 2 | 1 | 4 | 1 | | 1 |
| | 1 | 5 | 5 | | 5 | 5 | 1 | 1 | 2 | 0 | 1 | 0 |
| | 0.5 | 5 | 5 | | 5 | 5 | 0 | 1 | 1 | 0 | | 0 |
| 99 | 2 | 5 | 5 | | 5 | 5 | 0 | 0 | 3 | 0 | 0 | 1 |
| | 1 | 5 | 5 | | 5 | 5 | 0 | 0 | 1 | 0 | 0 | 1 |
| | 0.5 | 4 | 5 | | 5 | 5 | 0 | 0 | 0 | 0 | 0 | |
| 101 | 2 | 5 | 5 | 5 | 5 | 5 | 3.5 | 3 | 5 | 0 | 0 | 4.5 |
| | 1 | 5 | 5 | 5 | 5 | 5 | 1.5 | 2 | 3.5 | 0 | 0 | 3.5 |
| | 0.5 | 5 | 5 | 5 | 5 | 5 | 0 | 1 | 1 | 0 | 0 | 2.5 |
| 105 | 2 | 5 | 5 | 5 | 5 | 5 | 0.5 | 1 | 2 | 0 | 0 | 2 |
| | 1 | 2.5 | 5 | 4 | 5 | 5 | 0 | 0 | 0 | 0 | 0 | 1.5 |
| | 0.5 | 1 | 4 | 2.5 | 5 | 5 | 0 | 0 | 0 | 0 | 0 | 0.5 |
| 106 | 2 | 5 | 5 | 5 | 5 | 5 | 0 | 1 | 2 | 0 | 0 | 1 |
| | 1 | 5 | 5 | 5 | 5 | 5 | 0 | 1 | 1 | 0 | 0 | 1 |
| | 0.5 | 5 | 5 | 5 | 4 | 5 | 0 | 0 | 1 | 0 | 0 | 0 |
| 107 | 2 | 5 | 5 | | 5 | 5 | 4 | 3 | 4 | 0 | 0 | 2 |
| | 1 | 5 | 5 | | 5 | 5 | 1 | 1 | 3 | 0 | 0 | 2 |
| | 0.5 | 5 | 5 | | 5 | 5 | 0 | 0 | 2 | 0 | 0 | 1 |
| 108 | 2 | 5 | 5 | 5 | 5 | 5 | 1 | 1 | 2 | 1 | 1 | 2 |
| | 1 | 5 | 5 | 5 | 5 | 5 | 1 | 1 | 2 | 0 | 0 | 1 |
| | 0.5 | 5 | 5 | 5 | 5 | 5 | 0 | 0 | 0 | 0 | 0 | 0 |
| 114 | 2 | 5 | 5 | | 5 | 5 | 1 | 1 | 2 | 0 | | 1 |
| | 1 | 5 | 5 | | 5 | 5 | 0 | 1 | 2 | 0 | | 1 |
| | 0.5 | 5 | 5 | | 5 | 5 | 0 | 0 | 0 | 0 | | 1 |

TABLE 5C-continued

| Test | Amount | Herbicidal efficacy | | | | | Phytotoxicity | | | | | |
|---|---|---|---|---|---|---|---|---|---|---|---|---|
| Compound No. | applied (kg/ha) | barnyard-grass | crab-grass | green foxtail | redroot pigweed | rice flatsedge | rice | wheat | corn | soy-beans | cotton | sugar beet |
| 115 | 2 | 5 | 5 | | 5 | 5 | 0 | 0 | 2 | 0 | 0 | 1 |
| | 1 | 5 | 5 | | 5 | 5 | 0 | 0 | 0 | 0 | 0 | 0 |
| | 0.5 | 5 | 5 | | 5 | 5 | 0 | 0 | 0 | 0 | 0 | |
| 116 | 2 | 5 | 5 | | 5 | 5 | 1 | 0 | 0 | 0 | 0 | 0 |
| | 1 | 5 | 5 | | 5 | 5 | 0 | 0 | 0 | 0 | 0 | 0 |
| | 0.5 | 5 | 5 | | 5 | 5 | 0 | 0 | 0 | 0 | 0 | 0 |
| 117 | 2 | 5 | 5 | | 5 | 5 | 0 | 1 | 2 | 0 | 1 | 1 |
| | 1 | 5 | 5 | | 5 | 5 | 0 | 0 | 1 | 0 | | 1 |
| | 0.5 | 5 | 5 | | 5 | 5 | 0 | 0 | 0 | 0 | 0 | 0 |
| 118 | 2 | 5 | 5 | 5 | 2 | 5 | 0 | 0 | 1 | 0 | 0 | 0 |
| | 1 | 5 | 5 | 4.5 | 1 | 5 | 0 | 0 | 0.5 | 0 | 0 | 0 |
| | 0.5 | 4 | 5 | 4 | 0 | 5 | 0 | 0 | 0 | 0 | 0 | 0 |
| 126 | 2 | 5 | 5 | 5 | 5 | 5 | 2 | 3 | 4 | 0 | 1 | 3 |
| | 1 | 5 | 5 | 5 | 5 | 5 | 0 | 1 | 4 | 0 | 0 | 2 |
| | 0.5 | 5 | 5 | 5 | 5 | 5 | 0 | 1 | 3 | 0 | 0 | 0 |
| 127 | 2 | 5 | 5 | 5 | 5 | 5 | 3 | 4 | 5 | 0 | 0 | 3 |
| | 1 | 5 | 5 | 5 | 5 | 5 | 1 | 2 | 4 | 0 | 0 | 2 |
| | 0.5 | 5 | 5 | 5 | 5 | 5 | 0 | 0 | 3 | 0 | 0 | 1 |
| 132 | 2 | 5 | 5 | 5 | 3 | 5 | 4.5 | 3 | 5 | 0 | 0 | 3 |
| | 1 | 5 | 5 | 5 | 1 | 5 | 3.5 | 3 | 5 | 0 | 0 | 2.5 |
| | 0.5 | 5 | 5 | 5 | 0 | 5 | 3 | 1 | 3 | 0 | 0 | 1 |
| 133 | 2 | 5 | 5 | 5 | 3 | 5 | 4.5 | 3 | 5 | 0 | 0 | 1.5 |
| | 1 | 5 | 5 | 5 | 1 | 5 | 2.5 | 1.5 | 4.5 | 0 | 0 | 1 |
| | 0.5 | 5 | 5 | 5 | 0 | 5 | 2 | 1 | 4.5 | 0 | 0 | 0.5 |
| 135 | 2 | 5 | 5 | | 5 | 5 | 1 | 2 | 3 | 0 | | 1 |
| | 1 | 5 | 5 | | 5 | 5 | 1 | 1 | 2 | 0 | 0 | 1 |
| | 0.5 | 5 | 5 | | 5 | 5 | 0 | 0 | 1 | 0 | 0 | 0 |
| 136 | 2 | 5 | 5 | 5 | 5 | 5 | 0.5 | 1 | 2 | 0 | 0 | 1.5 |
| | 1 | 5 | 5 | 4.5 | 3 | 5 | 0 | 0.5 | 1.5 | 0 | 0 | 1 |
| | 0.5 | 3.5 | 5 | 4.5 | 4 | 5 | 0 | 0 | 1 | 0 | 0 | 0.5 |
| 138 | 2 | 5 | 5 | 5 | 2 | 5 | 1.5 | 1 | 3.5 | 0 | 0 | 1.5 |
| | 1 | 5 | 4.5 | 4.5 | 2 | 5 | 0.5 | 0.5 | 0.5 | 0 | 0 | 1 |
| | 0.5 | 3.5 | 4.5 | 4.5 | 1 | 5 | 0 | 0 | 0 | 0 | 0 | 0.5 |
| 146 | 2 | 5 | 5 | 5 | 5 | 5 | 2 | 2.5 | 5 | 1 | 1 | 2 |
| | 1 | 5 | 5 | 5 | 5 | 5 | 1.5 | 1.5 | 5 | 0 | 0.5 | 1.5 |
| | 0.5 | 5 | 5 | 5 | 0 | 5 | 1 | 1.5 | 5 | 0 | 0 | 1 |
| 151 | 2 | 5 | 5 | 5 | 5 | 5 | 0.5 | 0.5 | 1.5 | 0 | 0 | 1.5 |
| | 1 | 4.5 | 4.5 | 5 | 5 | 5 | 0 | 0 | 0.5 | 0 | 0 | 1 |
| | 0.5 | 2.5 | 4.5 | 4.5 | 5 | 5 | 0 | 0 | 0 | 0 | 0 | 0.5 |

Test Example 5C (herbicidal test by foliar treatment in an upland farm)

Upland farm soil was filled in plastic pots (120 $cm^2$), and seeds of barnyardgrass, crabgrass, redroot pigweed and rice flatsedge were sown and grown in a greenhouse until the barnyardgrass reached a three-leaf stage. Each of the test compounds was formulated into a wettable powder in accordance with Formulation Example 3B. The wettable powder in an amount equivalent to 4 kg per hectare as the active ingredient was diluted with water, and sprayed over the foliage of the plants from above by a small-sized sprayer at a rate of 1000 liters per hectare. After the spraying, the plants were grown in a greenhouse for 20 days. The herbicidal efficacy was examined in accordance with the standards given in Table 1C, and the results are shown in Table 6C.

TABLE 6C

| Test | Herbicidal efficacy | | | |
|---|---|---|---|---|
| Compound No. | barnyard-grass | crab-grass | redroot pigweed | rice flatsedge |
| 94 | 5 | 5 | 1 | 4 |
| 95 | 5 | 5 | 4 | 4 |
| 96 | 5 | 5 | 5 | 5 |
| 97 | 2 | 5 | 4 | 5 |
| 98 | 5 | 5 | 5 | 5 |
| 99 | 5 | 5 | 3 | 5 |
| 100 | 4 | 4 | 2 | 4 |
| 101 | 5 | 5 | 2 | 4 |
| 102 | 4 | 5 | 3 | 5 |

TABLE 6C-continued

| Test | Herbicidal efficacy | | | |
|---|---|---|---|---|
| Compound No. | barnyard-grass | crab-grass | redroot pigweed | rice flatsedge |
| 104 | 4 | 5 | 2 | 5 |
| 105 | 5 | 5 | 1 | 3 |
| 106 | 5 | 5 | 5 | 5 |
| 107 | 5 | 5 | 5 | 5 |
| 188 | 5 | 5 | 4 | 5 |
| 109 | 5 | 5 | 5 | 5 |
| 110 | 5 | 5 | 0 | 4 |
| 111 | 5 | 5 | 2 | 4 |
| 112 | 5 | 5 | 4 | 5 |
| 113 | 5 | 5 | 3 | 5 |
| 114 | 5 | 5 | 5 | 5 |
| 115 | 5 | 5 | 5 | 5 |
| 116 | 5 | 5 | 5 | 5 |
| 117 | 5 | 5 | 4 | 5 |
| 118 | 5 | 5 | 3 | 5 |
| 119 | 4 | 4 | 3 | 5 |
| 120 | 4 | 4 | 2 | 4 |
| 126 | 5 | 5 | 5 | 5 |
| 127 | 5 | 5 | 5 | 5 |
| 132 | 5 | 5 | 3 | 5 |
| 133 | 5 | 5 | 3 | 5 |
| 135 | 5 | 5 | 5 | 5 |
| 136 | 5 | 5 | 3 | 5 |
| 138 | 5 | 5 | 2 | 5 |
| 139 | 5 | 4 | 3 | 5 |
| 140 | 5 | 4 | 3 | 5 |
| 142 | 4 | 4 | 0 | 5 |
| 143 | 4 | 4 | 0 | 5 |
| 144 | 4 | 4 | 2 | 5 |
| 145 | 4 | 4 | 0 | 5 |
| 146 | 5 | 5 | 4 | 5 |
| 147 | 5 | 5 | 2 | 5 |

TABLE 6C-continued

| Test Compound No. | Herbicidal efficacy barnyard-grass | crab-grass | redroot pigweed | rice flatsedge |
|---|---|---|---|---|
| 148 | 5 | 5 | 3 | 5 |
| 149 | 5 | 5 | 3 | 5 |
| 150 | 5 | 5 | 4 | 5 |
| 151 | 5 | 5 | 2 | 5 |
| 152 | 5 | 5 | 4 | 5 |
| 153 | 5 | 5 | 3 | 5 |
| 154 | 5 | 5 | 2 | 5 |
| 155 | 5 | 5 | 4 | 5 |
| 156 | 5 | 4 | 3 | 5 |
| 158 | 5 | 5 | 2 | 5 |
| 159 | 5 | 5 | 2 | 5 |
| 160 | 5 | 5 | 2 | 5 |
| 161 | 5 | 5 | 2 | 5 |
| 166 | 5 | 3 | 3 | 5 |
| 169 | 5 | 5 | 4 | 5 |
| 170 | 5 | 5 | 2 | 5 |
| 174 | 5 | 5 | 4 | 5 |

Test Example 6C (herbicidal test by soil treatment in a paddy)

Porcelain pots, 10 cm in diameter, were filled with paddy soil, and after puddling, seeds of barnyardgrass, umbrella plant, monochoria and bulrush were sown. The pots were then watered to a depth of 3 cm. On the next day, a wettable powder prepared in accordance with Formulation Example 3B was diluted with water and dropped onto the water surface (amount applied: 4 kg per hectare as the active ingredient). The plants were then grown in a greenhouse, and 30 days after the treatment, the herbicidal activity of the compound of the invention was examined according to the standards given in Table 1C. The results are shown in Table 7C.

TABLE 7C

| Test Compound No. | Herbicidal efficacy barnyard-grass | umbrella plant | monochoria | bulrush |
|---|---|---|---|---|
| 175 | 5 | 5 | 5 | 5 |
| 176 | 5 | 3 | 5 | 3 |
| 177 | 5 | 5 | 5 | 5 |
| 178 | 2 | 2 | 0 | 1 |
| 179 | 5 | 5 | 5 | 5 |
| 180 | 5 | 5 | 5 | 5 |
| 181 | 5 | 5 | 5 | 5 |
| 182 | 5 | 5 | 5 | 5 |
| 183 | 5 | 5 | 5 | 5 |
| 184 | 5 | 5 | 5 | 5 |
| 185 | 5 | 5 | 5 | 5 |
| 186 | 5 | 5 | 5 | 5 |
| 187 | 5 | 5 | 5 | 5 |
| 188 | 2 | 5 | 5 | 2 |

Test Example 7C (herbicidal test by soil treatment in an upland farm)

Upland farm soil was filled in plastic pots (120 $cm^2$), and seeds of barnyardgrass, crabgrass, redroot pigweed and rice flatsedge were sown and covered with the soil. Each of the test compounds was formulated into a wettable powder in accordance with Formulation Example 3B. A predetermined amount of the wettable powder was diluted with water, and, by a small-sized sprayer, uniformly sprayed onto the soil surface at a rate of 1000 liters/hectare (the amount applied: 4 kg per hectare as the active ingredient). The plants were grown for 20 days in a greenhouse after the treatment, and the herbicidal efficacy and phytotoxicity were examined in accordance with the standards given in Table 1C. The results are shown in Table 8C.

TABLE 8C

| Test Compound No. | Herbicidal effect barnyard-grass | crab-grass | redroot pigweed | rice flatsedge |
|---|---|---|---|---|
| 175 | 5 | 5 | 3 | 5 |
| 176 | 1 | 4 | 2 | 5 |
| 177 | 5 | 5 | 2 | 5 |
| 178 | 1 | 2 | 2 | 5 |
| 179 | 5 | 5 | 5 | 5 |
| 180 | 5 | 5 | 5 | 5 |
| 181 | 5 | 5 | 4 | 5 |
| 182 | 5 | 5 | 5 | 5 |
| 183 | 5 | 5 | 5 | 5 |
| 184 | 0 | 3 | 2 | 5 |
| 185 | 5 | 5 | 5 | 5 |
| 186 | 5 | 5 | 5 | 5 |
| 187 | 5 | 5 | 3 | 5 |
| 188 | 1 | 1 | 2 | 3 |

Test Example 8C (herbicidal efficacy and phytotoxicity by soil treatment in an upland farm)

Upland farm soil was filled in plastic vats (600 $cm^2$). Seeds of barnyardgrass, crabgrass, green foxtail, redroot pigweed, rice flatsedge, rice, wheat, corn, soybeans, cotton and sugar beet were sown and covered with the soil. Each of the test compounds was formulated into a wettable powder in accordance with Formulation Example 3B. A predetermined amount of the wettable powder was diluted with water and uniformly sprayed onto the soil surface by a small-sized sprayer at a rate of 1000 liters per hectare. The plants were grown in a greenhouse for 30 days after the treatment. The herbicidal efficacy and phytotoxicity were examined in accordance with the standards given in Table 1C. The results are shown in Table 9C.

TABLE 9C

| Test Compound No. | Amount applied (kg/ha) | Herbicidal efficacy barnyard-grass | crab-grass | green foxtail | redroot pigweed | rice flatsedge | Phytotoxicity rice | wheat | corn | soy beans | cotton | sugar beet |
|---|---|---|---|---|---|---|---|---|---|---|---|---|
| 175 | 1 | 5 | 5 | 5 | — | 5 | 1 | 0 | 2 | 0.5 | 0 | 1 |
| | 0.5 | 5 | 5 | 5 | — | 5 | 0 | 0 | 2 | 0 | 0 | 0.5 |
| | 0.25 | 5 | 5 | 5 | — | 5 | 0 | 0 | 1.5 | 0 | 0 | 0.5 |
| 177 | 4 | 5 | 5 | 5 | — | 5 | 0.5 | 0.5 | 5 | 0.5 | 0.5 | 1 |
| | 2 | 5 | 5 | 5 | — | 5 | 0.5 | 0 | 3.5 | 0 | 0 | 0.5 |
| | 1 | 5 | 5 | 5 | — | 5 | 0 | 0 | 2 | 0 | 0 | 0.5 |
| 179 | 1 | 5 | 5 | 5 | 5 | 5 | 1 | 0.5 | 2 | 0 | 1 | 4 |
| | 0.5 | 5 | 5 | 5 | 5 | 5 | 0 | 0 | 1.5 | 0 | 0 | 4 |
| | 0.25 | 5 | 5 | 5 | 4.5 | 5 | 0 | 0 | 1.5 | 0 | 0 | 4 |
| 182 | 1 | 5 | 5 | 5 | 5 | 5 | 4.5 | 2.5 | 5 | 0 | 0 | 0.5 |

TABLE 9C-continued

| Test Compound No. | Amount applied (kg/ha) | Herbicidal efficacy barnyard-grass | crab-grass | green foxtail | redroot pigweed | rice flatsedge | Phytotoxicity rice | wheat | corn | soy beans | cotton | sugar beet |
|---|---|---|---|---|---|---|---|---|---|---|---|---|
| | 0.5 | 5 | 5 | 5 | 5 | 5 | 3 | 2 | 5 | 0 | 0 | 0 |
| | 0.25 | | 5 | 5 | 5 | 5 | 2 | 2 | 4.5 | 0 | 0 | 0 |
| 185 | 1 | 5 | 5 | 5 | 5 | 5 | 2.5 | 1 | 1.5 | 0 | 0 | 1.5 |
| | 0.5 | 5 | 5 | 5 | 4 | 5 | 2 | 0.5 | 1 | 0 | 0 | 1.5 |
| | 0.25 | 5 | 5 | 5 | 3 | 5 | 1 | 0 | 0 | 0 | 0 | 1.5 |
| 186 | 1 | 5 | 5 | 5 | 1 | 5 | 0 | 0 | 1.5 | 0.5 | 0 | 0 |
| | 0.5 | 5 | 5 | 5 | 1 | 5 | 0 | 0 | 1 | 0 | 0 | 0 |
| | 0.25 | 5 | 5 | 5 | 0 | 5 | 0 | 0 | 0 | 0 | 0 | 0 |
| 187 | 2 | 5 | 5 | 5 | 2 | 5 | 0 | 0.5 | 0.5 | 1 | 1 | 1.5 |
| | 1 | 5 | 5 | 5 | 1.5 | 5 | 0 | 0 | 0 | 0 | 0 | 0 |
| | 0.5 | 4.5 | 4.5 | 3.5 | 0.5 | 5 | 0 | 0 | 0 | 0 | 0 | 0 |

Test Example 9C (herbicidal test by soil treatment in a paddy)

Porcelain pots, 10 cm in diameter, were filled with paddy soil, and after puddling, seeds of barnyardgrass, umbrella plant, monochoria and bulrush were sown. The pots were then watered to a depth of 3 cm. On the next day, a wettable powder prepared in accordance with Formulation Example 3B was diluted with water and dropped onto the water surface (amount applied: 4 kg per hectare as the active ingredient). The plants were then grown in a greenhouse, and 30 days after the treatment, the herbicidal activity of the compound of the invention was examined according to the standards given in Table 1C. The results are shown in Table 10C.

TABLE 7C

| Test Compound No. | Herbicidal efficacy barnyard-grass | umbrella plant | monochoria | bulrush |
|---|---|---|---|---|
| 206 | 5 | 5 | 5 | 5 |
| 209 | 5 | 5 | 5 | 5 |
| 210 | 5 | 5 | 5 | 4 |
| 211 | 5 | 5 | 5 | 4 |
| 212 | 5 | 5 | 5 | 5 |
| 258 | 5 | 4 | 4 | 4 |
| 259 | 4 | 3 | 2 | 4 |

Test Example 10C (herbicidal test by soil treatment in an upland farm)

Upland farm soil was filled in plastic vats (600 $cm^2$). Seeds of barnyardgrass, crabgrass, green foxtail, redroot pigweed, rice flatsedge, rice, wheat, corn, soybeans, cotton and sugar beat were sown and covered with the soil. Each of the test compounds was formulated into a wettable powder in accordance with Formulation Example 3B. A predetermined amount of the wettable powder was diluted with water and uniformly sprayed onto the soil surface by a small-sized sprayer at a rate of 1000 liters per hectare. The plants were grown in a greenhouse for 30 days after the treatment. The herbicidal efficacy and phytotoxicity were examined in accordance with the standards given in Table 1C. The results are shown in Table 11C.

TABLE 11C

| Test Compound No. | Amount applied (kg/ha) | Herbicidal efficacy barnyard-grass | crab-grass | green foxtail | redroot pigweed | rice flatsedge | Phytotoxicity rice | wheat | corn | soy-beans | cotton | sugar beet |
|---|---|---|---|---|---|---|---|---|---|---|---|---|
| 212 | 1 | 5 | 5 | 5 | 5 | 5 | 0.5 | 0 | 4.5 | 0 | 3 | 3 |
| | 0.5 | 5 | 5 | 5 | 5 | 5 | 0 | 0 | 2 | 0 | 1 | 3 |
| | 0.25 | 5 | 5 | 5 | 5 | 5 | 0 | 0 | 0 | 0 | 0 | 2 |

Test Example 11 (herbicidal test by water treatment in a paddy field)

Into each porcelain pot having a diameter of 10 cm, paddy soil was filled and puddled, and seeds of barnyardgrass (*Echinochloa crus-galli* L.), small flower flatsedge, monochoria and Japanese bulrush were sown, and water was filled in a depth of 3 cm. One day later, a predetermined amount of the wettable powder prepared in Formulation Example 3 and diluted with water was dropwise applied to the surface of the water (dose of the active ingredient: 4 kg/hectare). Thereafter, they were grown in a greenhouse. Thirty days after the application, the herbicidal effects were evaluated in accordance with the standards as identified in Table 1C. The results thereby obtained are shown in Table 12.

TABLE 12

| Test Compound No. | Herbicidal effects barnyard-grass | small flower flatsedge | monochoria | Japanese bulrush |
|---|---|---|---|---|
| 260 | 5 | 5 | 5 | 5 |
| 261 | 5 | 5 | 5 | 5 |
| 262 | 5 | 5 | 5 | 5 |
| 263 | 5 | 5 | 5 | 5 |
| 264 | 5 | 5 | 5 | 5 |
| 265 | 5 | 5 | 5 | 5 |
| 266 | 5 | 5 | 5 | 5 |
| 267 | 5 | 5 | 5 | 5 |
| 268 | 5 | 5 | 5 | 5 |
| 269 | 5 | 5 | 5 | 5 |
| 270 | 5 | 5 | 5 | 5 |
| 271 | 5 | 5 | 5 | 5 |
| 272 | 5 | 5 | 5 | 5 |
| 273 | 5 | 5 | 5 | 5 |
| 274 | 5 | 5 | 5 | 5 |
| 275 | 5 | 5 | 5 | 5 |
| 276 | 5 | 5 | 5 | 5 |
| 277 | 5 | 5 | 5 | 5 |
| 278 | 5 | 5 | 5 | 5 |
| 279 | 5 | 5 | 5 | 5 |
| 280 | 5 | 5 | 5 | 5 |
| 281 | 5 | 5 | 5 | 5 |
| 282 | 5 | 5 | 5 | 5 |
| 283 | 5 | 5 | 5 | 5 |

TABLE 12-continued

| Test Compound No. | Herbicidal effects barnyard-grass | small flower flatsedge | monochoria | Japanese bulrush |
|---|---|---|---|---|
| 284 | 5 | 5 | 5 | 4 |
| 285 | 5 | 5 | 5 | 5 |
| 286 | 5 | 5 | 5 | 5 |
| 287 | 5 | 5 | 5 | 5 |
| 288 | 5 | 5 | 5 | 5 |
| 289 | 5 | 5 | 5 | 5 |
| 290 | 5 | 5 | 5 | 5 |
| 291 | 5 | 5 | 5 | 5 |
| 292 | 5 | 5 | 5 | 5 |
| 293 | 5 | 5 | 5 | 5 |
| 294 | 5 | 5 | 5 | 5 |
| 295 | 5 | 5 | 5 | 5 |
| 296 | 5 | 5 | 5 | 5 |
| 297 | 5 | 5 | 5 | 5 |
| 298 | 5 | 5 | 5 | 5 |
| 299 | 5 | 5 | 5 | 5 |
| 300 | 5 | 5 | 5 | 5 |
| 301 | 5 | 5 | 5 | 5 |
| 302 | 5 | 5 | 5 | 5 |
| 303 | 5 | 5 | 5 | 5 |
| 304 | 5 | 5 | 5 | 5 |
| 305 | 5 | 5 | 5 | 5 |
| 306 | 5 | 5 | 5 | 5 |
| 307 | 5 | 5 | 5 | 5 |
| 308 | 5 | 5 | 5 | 5 |
| 309 | 5 | 5 | 5 | 5 |
| 310 | 5 | 5 | 5 | 5 |
| 311 | 5 | 5 | 5 | 5 |
| 312 | 5 | 5 | 5 | 5 |
| 313 | 5 | 5 | 5 | 5 |
| 314 | 5 | 5 | 5 | 5 |
| 315 | 5 | 5 | 5 | 5 |
| 316 | 5 | 5 | 5 | 5 |
| 317 | 5 | 5 | 5 | 4 |
| 318 | 5 | 5 | 5 | 5 |
| 319 | 5 | 5 | 5 | 5 |
| 320 | 5 | 5 | 5 | 5 |
| 321 | 5 | 5 | 5 | 5 |
| 322 | 5 | 5 | 5 | 5 |
| 323 | 5 | 5 | 5 | 5 |
| 324 | 5 | 5 | 5 | 5 |
| 325 | 5 | 5 | 5 | 5 |
| 326 | 5 | 5 | 5 | 5 |
| 327 | 5 | 5 | 5 | 5 |
| 328 | 5 | 5 | 5 | 5 |
| 329 | 5 | 5 | 5 | 5 |
| 330 | 5 | 5 | 5 | 5 |
| 331 | 5 | 5 | 5 | 4 |
| 332 | 5 | 5 | 5 | 5 |
| 333 | 5 | 5 | 4 | 4 |
| 334 | 5 | 5 | 5 | 5 |
| 335 | 5 | 5 | 4 | 5 |
| 336 | 5 | 5 | 5 | 5 |
| 337 | 5 | 5 | 5 | 5 |
| 338 | 5 | 5 | 5 | 5 |
| 339 | 5 | 5 | 5 | 5 |
| 340 | 5 | 5 | 5 | 5 |
| 351 | 5 | 5 | 5 | 5 |
| 342 | 5 | 5 | 5 | 5 |
| 343 | 5 | 5 | 5 | 5 |
| 344 | 5 | 5 | 5 | 5 |
| 345 | 5 | 5 | 5 | 5 |
| 346 | 5 | 5 | 5 | 5 |
| 347 | 5 | 5 | 4 | 5 |
| 348 | 5 | 5 | 5 | 5 |
| 349 | 5 | 5 | 5 | 5 |
| 350 | 5 | 5 | 5 | 5 |
| 351 | 5 | 5 | 5 | 5 |
| 352 | 5 | 5 | 5 | 5 |
| 353 | 5 | 5 | 5 | 5 |
| 354 | 5 | 5 | 5 | 5 |
| 355 | 5 | 5 | 5 | 5 |
| 356 | 5 | 5 | 5 | 5 |
| 357 | 5 | 5 | 5 | 5 |
| 358 | 5 | 5 | 5 | 5 |
| 359 | 5 | 5 | 5 | 5 |
| 360 | 5 | 5 | 5 | 5 |
| 361 | 5 | 5 | 5 | 5 |

TABLE 12-continued

| Test Compound No. | Herbicidal effects barnyard-grass | small flower flatsedge | monochoria | Japanese bulrush |
|---|---|---|---|---|
| 362 | 5 | 5 | 5 | 5 |
| 363 | 5 | 5 | 5 | 5 |
| 364 | 5 | 5 | 5 | 4 |
| 365 | 5 | 5 | 5 | 4 |
| 366 | 5 | 4 | 4 | 4 |
| 367 | 5 | 5 | 5 | 5 |
| 368 | 5 | 5 | 5 | 5 |
| 369 | 5 | 5 | 5 | 5 |
| 370 | 5 | 5 | 5 | 5 |
| 371 | 4 | 5 | 5 | 5 |
| 372 | 5 | 5 | 5 | 5 |
| 373 | 5 | 5 | 5 | 5 |
| 374 | 5 | 5 | 5 | 5 |
| 375 | 5 | 5 | 5 | 5 |
| 376 | 5 | 5 | 5 | 5 |
| 377 | 5 | 5 | 5 | 5 |
| 378 | 5 | 5 | 5 | 5 |
| 379 | 5 | 5 | 5 | 5 |
| 380 | 5 | 5 | 5 | 5 |
| 381 | 5 | 5 | 5 | 5 |
| 382 | 5 | 5 | 5 | 5 |
| 383 | 5 | 5 | 5 | 5 |
| 384 | 5 | 5 | 4 | 4 |
| 385 | 5 | 5 | 5 | 5 |
| 386 | 5 | 5 | 5 | 4 |
| 387 | 5 | 5 | 5 | 5 |
| 388 | 5 | 5 | 5 | 5 |
| 389 | 5 | 5 | 5 | 5 |
| 390 | 5 | 5 | 5 | 5 |
| 391 | 5 | 5 | 5 | 5 |
| 392 | 5 | 5 | 5 | 5 |
| 393 | 5 | 5 | 5 | 5 |
| 394 | 5 | 5 | 5 | 5 |
| 395 | 5 | 5 | 5 | 5 |
| 396 | 5 | 5 | 5 | 5 |
| 397 | 5 | 5 | 5 | 5 |
| 398 | 5 | 5 | 5 | 5 |
| 399 | 5 | 5 | 5 | 5 |
| 400 | 5 | 5 | 5 | 5 |
| 401 | 5 | 5 | 5 | 5 |
| 402 | 5 | 5 | 5 | 5 |
| 403 | 5 | 5 | 5 | 5 |
| 404 | 5 | 5 | 5 | 5 |
| 405 | 5 | 5 | 5 | 5 |
| 406 | 5 | 5 | 5 | 5 |
| 407 | 5 | 5 | 5 | 5 |
| 408 | 5 | 5 | 5 | 5 |
| 409 | 5 | 5 | 4 | 4 |
| 410 | 5 | 5 | 5 | 5 |
| 411 | 5 | 5 | 5 | 5 |
| 412 | 5 | 5 | 5 | 5 |
| 413 | 5 | 4 | 4 | 4 |
| 414 | 5 | 5 | 5 | 5 |
| 415 | 5 | 5 | 5 | 5 |
| 416 | 5 | 5 | 5 | 5 |
| 417 | 5 | 5 | 5 | 5 |
| 418 | 5 | 5 | 5 | 4 |
| 419 | 5 | 5 | 5 | 5 |
| 420 | 5 | 5 | 5 | 5 |
| 421 | 5 | 5 | 4 | 4 |
| 422 | 5 | 5 | 5 | 4 |
| 423 | 5 | 5 | 5 | 4 |
| 424 | 5 | 5 | 5 | 5 |
| 425 | 5 | 5 | 4 | 4 |
| 426 | 5 | 5 | 5 | 5 |
| 427 | 5 | 5 | 5 | 5 |
| 428 | 5 | 5 | 5 | 5 |
| 429 | 5 | 5 | 5 | 5 |
| 430 | 5 | 5 | 5 | 5 |
| 431 | 5 | 5 | 5 | 5 |
| 432 | 5 | 5 | 5 | 5 |
| 433 | 5 | 5 | 5 | 5 |
| 434 | 5 | 5 | 5 | 5 |
| 435 | 5 | 5 | 5 | 4 |
| 436 | 5 | 5 | 5 | 5 |
| 437 | 5 | 5 | 5 | 5 |
| 438 | 5 | 5 | 5 | 5 |
| 439 | 5 | 5 | 5 | 5 |

TABLE 12-continued

| Test Compound No. | Herbicidal effects barnyard-grass | small flower flatsedge | monochoria | Japanese bulrush |
|---|---|---|---|---|
| 440 | 5 | 5 | 5 | 5 |
| 441 | 5 | 5 | 5 | 5 |
| 442 | 5 | 5 | 5 | 5 |
| 443 | 5 | 5 | 5 | 5 |
| 444 | 5 | 5 | 5 | 5 |
| 445 | 5 | 5 | 5 | 5 |
| 446 | 5 | 5 | 5 | 5 |
| 447 | 5 | 5 | 5 | 5 |
| 448 | 5 | 5 | 5 | 5 |
| 449 | 5 | 5 | 5 | 5 |
| 450 | 5 | 5 | 5 | 5 |
| 451 | 5 | 4 | 5 | 2 |
| 452 | 5 | 5 | 5 | 5 |
| 453 | 5 | 5 | 5 | 5 |
| 454 | 5 | 5 | 5 | 5 |
| 455 | 5 | 5 | 5 | 5 |
| 456 | 5 | 5 | 5 | 5 |
| 457 | 5 | 5 | 5 | 5 |
| 458 | 5 | 5 | 5 | 5 |
| 459 | 5 | 5 | 5 | 5 |
| 460 | 5 | 5 | 5 | 5 |
| 461 | 5 | 5 | 5 | 5 |
| 462 | 5 | 5 | 5 | 5 |
| 463 | 5 | 5 | 5 | 5 |
| 464 | 5 | 5 | 5 | 5 |
| 465 | 5 | 5 | 5 | 5 |
| 466 | 5 | 5 | 5 | 5 |
| 467 | 5 | 5 | 5 | 5 |
| 468 | 5 | 5 | 5 | 5 |
| 469 | 5 | 5 | 5 | 5 |
| 472 | 5 | 5 | 5 | 5 |
| 473 | 5 | 5 | 5 | 5 |
| 475 | 5 | 5 | 5 | 5 |
| 476 | 5 | 5 | 5 | 5 |
| 477 | 5 | 5 | 5 | 5 |
| 478 | 5 | 5 | 5 | 5 |
| 479 | 5 | 5 | 5 | 5 |
| 481 | 5 | 5 | 5 | 5 |
| 482 | 5 | 5 | 5 | 5 |
| 484 | 5 | 5 | 5 | 5 |
| 485 | 5 | 5 | 5 | 5 |
| 486 | 5 | 5 | 5 | 5 |
| 487 | 5 | 5 | 5 | 5 |
| 488 | 5 | 5 | 5 | 5 |
| 489 | 5 | 5 | 5 | 5 |
| 490 | 5 | 5 | 5 | 5 |
| 491 | 5 | 5 | 5 | 5 |
| 492 | 5 | 5 | 5 | 5 |
| 493 | 5 | 5 | 5 | 5 |

TABLE 12-continued

| Test Compound No. | Herbicidal effects barnyard-grass | small flower flatsedge | monochoria | Japanese bulrush |
|---|---|---|---|---|
| 494 | 5 | 5 | 5 | 5 |
| 495 | 5 | 5 | 5 | 5 |
| 496 | 5 | 5 | 5 | 5 |
| 497 | 5 | 5 | 5 | 5 |
| 498 | 5 | 5 | 5 | 5 |
| 499 | 5 | 5 | 5 | 5 |
| 500 | 5 | 5 | 5 | 5 |
| 501 | 5 | 5 | 5 | 5 |
| 502 | 5 | 5 | 5 | 5 |
| 503 | 5 | 5 | 5 | 5 |
| 504 | 5 | 5 | 5 | 5 |
| 505 | 5 | 5 | 5 | 5 |
| 506 | 5 | 5 | 5 | 5 |
| 507 | 5 | 5 | 5 | 5 |
| 508 | 5 | 5 | 5 | 5 |
| 509 | 5 | 5 | 5 | 5 |
| Comparative* Compound | 0 | 0 | 0 | 0 |

*

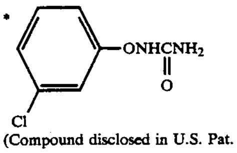

(Compound disclosed in U.S. Pat. No. 3,332,975)

Test Example 12 (herbicidal test for selectivity between rice and barnyardgrass)

Into each 1/5000 Wagner pot, paddy soil was filled and puddled, then seeds of barnyardgrass were sown and grown until they reached the two-leaf stage. The barnyardgrass of two-leaf stage was thinned out to adjust the number of barnyardgrass to fifteen per pot, and rice seedlings of two-leaf stage were transplanted in the same pot. One day after the transplant, a predetermined amount of the wettable powder prepared from the test compound in accordance with Formulation Example 3 and diluted with water, was dropwise applied to the surface of the water. Thereafter, they were grown an a greenhouse, and thirty days after the application, the herbicidal effects and phytotoxicity were evaluated in accordance with the standards as identified in Table 1C. The results thereby obtained are shown in Table 13.

TABLE 13

| Test Compound | Dose kg/Ha | Herbicidal effects Barnyard grass | Phyto-toxicity Paddy rice | Test Compound | Dose kg/Ha | Herbicidal effects Barnyard grass | Phyto-toxicity Paddy rice |
|---|---|---|---|---|---|---|---|
| 260 | 1 | 5 | 1 | 297 | 1 | 5 | 0 |
| | 0.5 | 5 | 0 | | 0.5 | 5 | 0 |
| | 0.25 | 5 | 0 | | 0.25 | 5 | 0 |
| 261 | 1 | 5 | 1 | 298 | 0.5 | 5 | 0 |
| | 0.5 | 5 | 0 | | 0.25 | 5 | 0 |
| 264 | 1 | 5 | 1 | 299 | 1 | 5 | 0 |
| | 0.5 | 5 | 0 | | 0.5 | 5 | 0 |
| | 0.25 | 5 | 0 | | 0.25 | 5 | 0 |
| 265 | 1 | 5 | 0 | 300 | 1 | 5 | 1.5 |
| | 0.5 | 5 | 0 | | 0.5 | 5 | 0 |
| | 0.25 | 5 | 0 | | 0.25 | 4 | 0 |
| 275 | 0.5 | 5 | 0 | 301 | 1 | 5 | 0 |
| | 0.25 | 5 | 0 | | 0.25 | 5 | 0 |
| | | | | | 0.25 | 5 | 0 |
| 280 | 0.5 | 5 | 1 | 302 | 1 | 5 | 0.5 |
| | 0.25 | 5 | 0 | | 0.5 | 5 | 0 |
| 285 | 1 | 5 | 0 | 303 | 1 | 5 | 0 |
| | 0.5 | 5 | 0 | | 0.5 | 5 | 0 |
| 286 | 1 | 5 | 0 | 304 | 1 | 5 | 0 |
| | 0.5 | 5 | 0 | | 0.5 | 5 | 0 |
| | | | | | 0.25 | 4.5 | 0 |

TABLE 13-continued

| Test Compound | Dose kg/Ha | Herbicidal effects Barnyard grass | Phyto-toxicity Paddy rice | Test Compound | Dose kg/Ha | Herbicidal effects Barnyard grass | Phyto-toxicity Paddy rice |
|---|---|---|---|---|---|---|---|
| 287 | 1 | 5 | 1 | 306 | 1 | 5 | 1 |
| | 0.5 | 5 | 0 | | 0.5 | 5 | 1 |
| | 0.25 | 5 | 0 | | 0.2 | 5 | 0 |
| 288 | 1 | 5 | 0 | 308 | 1 | 5 | 0 |
| | 0.5 | 5 | 0 | | 0.5 | 5 | 0 |
| | 0.25 | | 0 | | | | |
| 289 | 1 | 5 | 0 | 309 | 1 | 5 | 0 |
| | 0.5 | 4.5 | 0 | | 0.5 | 5 | 0 |
| | | | | | 0.25 | 5 | 0 |
| 290 | 1 | 5 | 0 | 310 | 1 | 5 | 0 |
| | 0.5 | 4 | 0 | | 0.5 | 5 | 0 |
| | | | | | 0.25 | 4.5 | 0 |
| 292 | 1 | 5 | 0 | 311 | 1 | 5 | 0 |
| | 0.5 | 5 | 0 | | 0.5 | 5 | 0 |
| | 0.25 | 5 | 0 | | 0.25 | 4 | 0 |
| 293 | 1 | 5 | 1 | 314 | 1 | 5 | 0 |
| | 0.5 | 5 | 0 | | 0.5 | 4.5 | 0 |
| | 0.25 | 5 | 0 | | | | |
| 316 | 1 | 5 | 0 | 346 | 1 | 5 | 0 |
| | 0.5 | 5 | 0 | | 0.5 | 5 | 0 |
| | 0.25 | 5 | 0 | | 0.25 | 5 | 0 |
| 318 | 1 | 5 | 1 | 348 | 1 | 5 | 1 |
| | 0.5 | 5 | 0.5 | | 0.5 | 5 | 1 |
| | 0.25 | 5 | 0 | | 0.25 | | 0 |
| 319 | 1 | 5 | 0 | 351 | 1 | 5 | 0 |
| | 0.5 | 5 | 0 | | 0.5 | 5 | 0 |
| | 0.25 | 5 | 0 | | | | |
| 320 | 1 | 5 | 1 | 357 | 1 | 5 | 2 |
| | 0.5 | 5 | 1 | | 0.5 | 5 | 0 |
| | 0.25 | 3 | 0 | | | | |
| 321 | 1 | 5 | 0 | 359 | 1 | 5 | 0 |
| | 0.5 | 4.5 | 0 | | 0.5 | 4.5 | 0 |
| | 0.25 | 4.5 | 0 | | | | |
| 326 | 1 | 5 | 0 | 360 | 1 | 5 | 1 |
| | 0.5 | 4 | 0 | | 0.5 | 5 | 0 |
| | 0.25 | 4 | 0 | | | | |
| 327 | 1 | 5 | 1 | 362 | 1 | 5 | 0 |
| | 0.5 | 5 | 0 | | 0.5 | 5 | 0 |
| | 0.25 | 5 | 0 | | | | |
| 335 | 1 | 5 | 0 | 364 | 1 | 5 | 0 |
| | 0.5 | 4 | 0 | | 0.5 | 4.5 | 0 |
| | 0.25 | | | | 0.25 | 4 | 0 |
| 336 | 1 | 5 | 0 | 377 | 0.5 | 5 | 0 |
| | 0.5 | 5 | 0 | | 0.25 | 5 | 0 |
| 338 | 1 | 5 | 1 | 387 | 0.5 | 5 | 0 |
| | 0.5 | 5 | 0 | | 0.25 | 5 | 0 |
| | 0.25 | 5 | 0 | | | | |
| 339 | 1 | 5 | 2 | 405 | 1 | 5 | 1 |
| | 0.5 | 4 | 0 | | 0.5 | 5 | 1 |
| | 0.25 | 4 | 0 | | 0.25 | 5 | 0 |
| 343 | 1 | 5 | 0 | 430 | 1 | 5 | 1 |
| | 0.5 | 5 | 0 | | 0.5 | 5 | 0 |
| | 0.25 | 4.5 | | | 0.25 | 5 | 0 |
| 345 | 1 | 5 | 1 | 431 | 0.5 | 5 | 1 |
| | 0.5 | 5 | 0 | | 0.25 | 5 | 0 |
| | | | | 438 | 0.5 | 5 | 1 |
| | | | | | 0.25 | 5 | 0.5 |
| | | | | 441 | 1 | 5 | 0 |
| | | | | | 0.5 | 5 | 0 |
| 442 | 1 | 5 | 1 | 459 | 1 | 5 | 1.5 |
| | 0.5 | 5 | 0 | | 0.5 | 5 | 1.5 |
| | 0.25 | 5 | 0 | | 0.25 | 5 | 0 |
| 445 | 0.5 | 5 | 1 | 460 | 1 | 5 | 3 |
| | 0.25 | 5 | 0 | | 0.5 | 5 | 0 |
| | | | | | 0.25 | 5 | 0 |
| 446 | 1 | 5 | 1 | 461 | 1 | 5 | 3 |
| | 0.5 | 5 | 0 | | 0.5 | 5 | 3 |
| | 0.25 | 5 | 0 | | 0.25 | 5 | 0 |
| 447 | 1 | 5 | 1.5 | 462 | 0.5 | 5 | 3 |
| | 0.5 | 5 | 0 | | 0.25 | 5 | 0 |
| | 0.25 | 4 | 0 | | | | |
| 448 | 1 | 5 | 1 | 463 | 1 | 5 | 0 |
| | 0.5 | 5 | 1 | | 0.5 | 5 | 0 |
| | 0.25 | 5 | 0 | | 0.25 | 5 | 0 |
| 449 | 1 | 5 | 1 | 464 | 1 | 5 | 0 |
| | 0.5 | 5 | 1 | | 0.5 | 4.5 | 0 |
| | 0.25 | 5 | 0 | | 0.25 | 3 | 0 |
| 450 | 1 | 5 | 3 | 465 | 1 | 5 | 3 |

TABLE 13-continued

| Test Compound | Dose kg/Ha | Herbicidal effects Barnyard grass | Phyto-toxicity Paddy rice | Test Compound | Dose kg/Ha | Herbicidal effects Barnyard grass | Phyto-toxicity Paddy rice |
|---|---|---|---|---|---|---|---|
| | 0.5 | 5 | 1.5 | | 0.5 | 5 | 1 |
| | 0.25 | 5 | 1 | | 0.25 | 5 | 0 |
| 452 | 1 | 5 | 3 | 466 | 1 | 5 | 0 |
| | 0.5 | 5 | 1 | | 0.5 | 5 | 0 |
| | 0.25 | 5 | 1 | | 0.25 | 5 | 0 |
| 453 | 1 | 5 | 0.5 | 467 | 1 | 5 | 0.5 |
| | 0.5 | 5 | 0 | | 0.5 | 5 | 0 |
| | 0.25 | 5 | 0 | | 0.25 | 5 | 0 |
| 454 | 1 | 5 | 0 | 468 | 1 | 5 | 0 |
| | 0.5 | 5 | 0 | | 0.5 | 5 | 0 |
| | 0.25 | 5 | 0 | | 0.25 | 4.5 | 0 |
| 455 | 1 | 5 | 0 | 469 | 1 | 5 | 0 |
| | 0.5 | 4 | 0 | | 0.5 | 5 | 0 |
| | 0.25 | 2 | 0 | | 0.25 | 5 | 0 |
| 456 | 1 | 5 | 0 | 472 | 1 | 5 | 1 |
| | 0.5 | 5 | 0 | | 0.5 | 5 | 1 |
| | 0.25 | 5 | 0 | | 0.25 | 5 | 1 |
| 458 | 1 | 5 | 2 | 473 | 1 | 5 | 0 |
| | 0.5 | 5 | 1 | | 0.5 | 5 | 0 |
| | 0.25 | 4 | 0 | | 0.25 | 4 | 0 |
| 475 | 1 | 5 | 0 | 492 | 1 | 5 | 2 |
| | 0.5 | 4 | 0 | | 0.5 | 5 | 0 |
| | 0.25 | 4 | 0 | | 0.25 | 4.5 | 0 |
| 477 | 1 | 5 | 0 | 493 | 1 | 5 | 0 |
| | 0.5 | 5 | 0 | | 0.5 | 5 | 0 |
| | 0.25 | 4 | 0 | | 0.25 | 4.5 | 0 |
| 478 | 0.25 | 5 | 0 | 494 | 0.25 | 5 | 0 |
| 479 | 1 | 5 | 1 | 496 | 0.5 | 5 | 0 |
| | 0.5 | 5 | 1 | | 0.25 | 5 | 0 |
| | 0.25 | 5 | 0 | | | | |
| 481 | 1 | 5 | 1 | 497 | 1 | 5 | 0 |
| | 0.5 | 5 | 0 | | 0.5 | 5 | 0 |
| | 0.25 | 5 | 0 | | 0.25 | 5 | 0 |
| 482 | 1 | 5 | 2 | 498 | 1 | 5 | 0 |
| | 0.5 | 5 | 0 | | 0.5 | 5 | 0 |
| | 0.25 | 5 | 0 | | 0.25 | 5 | 0 |
| 485 | 1 | 5 | 2 | 499 | 1 | 5 | 2 |
| | 0.5 | 5 | 0 | | 0.5 | 5 | 2 |
| | 0.25 | 5 | 0 | | 0.25 | 5 | 0 |
| 486 | 1 | 5 | 3 | 503 | 1 | | 0 |
| | 0.5 | 5 | 1 | | 0.5 | | 0 |
| | 0.25 | 5 | 0 | | 0.25 | | 0 |
| 487 | 0.5 | 5 | 1 | 504 | 1 | | 0 |
| | 0.25 | 5 | 0 | | 0.5 | | 0 |
| | | | | | 0.25 | | 0 |
| 488 | 1 | 5 | 1 | 505 | 1 | 5 | 0 |
| | 0.5 | 5 | 0 | | 0.5 | 5 | 0 |
| | 0.25 | 4 | 0 | | 0.25 | 3 | 0 |
| 489 | 1 | 5 | 1.5 | 506 | 1 | | 0 |
| | 0.5 | 5 | 1.5 | | 0.5 | | 0 |
| | 0.25 | 5 | 1 | | 0.25 | | 0 |
| 490 | 1 | 5 | 0 | 507 | 1 | 5 | 0 |
| | 0.5 | 5 | 0 | | 0.5 | 5 | 0 |
| | 0.25 | 5 | 0 | | 0.25 | 2 | 0 |
| 491 | 1 | 5 | 1 | 508 | 0.5 | 5 | 0 |
| | 0.5 | 5 | 0 | | 0.25 | 5 | 0 |
| | 0.25 | 4 | 0 | | | | |
| 510 | 1 | 5 | 3.5 | 509 | 1 | 5 | 0 |
| | 0.5 | 4 | 0 | | 0.5 | 5 | 0 |
| | 0.25 | 3.5 | 0 | | 0.25 | 4 | 0 |
| DCMU (Comparative Compound) | 1 | 5 | 5 | | | | |
| | 0.5 | 5 | 4 | | | | |
| | 0.25 | 3 | 2 | | | | |

Test Example 13 (herbicidal test by upland soil treatment)

Into each plastic pot of 600 $cm^2$, upland soil was filled, then seeds of barnyardgrass, crabgrass, green foxtail, redroot pigweed, rice flatsedge, rice, wheat, maize, soybean, cotton and sugar beet were sown, and they were covered with soil. A predetermined amount of the wettable powder prepared from the test compound in accordance with Formulation Example 3 and diluted with water was uniformly applied to the surface of the soil at an application rate of 1000 liter/hectare by means of a small-size sprayer. They were grown in a greenhouse, and twenty days after the application, the herbicidal effects and phytotoxicity were evaluated in accordance with the standards as identified in Table 1C. The results thereby obtained are shown in Table 14.

TABLE 14

| Test Compound | Dose kg/Ha | Herbicidal effects: Barnyard-grass | Crab-grass | Green foxtail | Redroot pigweed | Rice flatsedge | Phytotoxicity: Rice | Wheat | Maize | Soy-bean | Cotton | Sugar beet |
|---|---|---|---|---|---|---|---|---|---|---|---|---|
| 260 | 4 | 5 | 5 | 5 | 5 | 5 | 0 | 0 | 0 | 0 | 0 | 3 |
| | 1 | 5 | 5 | 5 | 5 | 5 | 0 | 0 | 0 | 0 | 0 | 2 |
| 264 | 4 | 5 | 5 | 5 | 5 | 5 | 0 | 0 | 0 | 0 | 0 | 3 |
| | 1 | 5 | 5 | 5 | 5 | 5 | 0 | 0 | 0 | 0 | 0 | 2 |
| 266 | 4 | 5 | 5 | 5 | 5 | 5 | 2 | 0.5 | 4 | 0 | 0 | 1 |
| | 1 | 5 | 4 | 5 | 3 | 5 | 0 | 0 | 0.5 | 0 | 0 | 0.5 |
| 280 | 4 | 5 | 5 | 5 | 5 | 5 | 4.5 | 4.5 | 5 | 4 | 0.5 | 2.5 |
| | 1 | 5 | 5 | 5 | 5 | 5 | 5 | 3 | 5 | 1.5 | 0 | 2 |
| 285 | 4 | 5 | 5 | 5 | 3 | 5 | 5 | 2 | 4.5 | 0 | 0 | 1.5 |
| | 1 | 5 | 5 | 5 | 1 | 5 | 4 | 0.5 | 4 | 0 | 0 | 1 |
| 286 | 4 | 5 | 5 | 5 | 1 | 5 | 2.5 | 2 | 4 | 0 | 0 | 0.5 |
| | 1 | 5 | 5 | 5 | 0 | 5 | 0.5 | 0 | 2 | 0 | 0 | 0 |
| 289 | 4 | 5 | 5 | 5 | 5 | 5 | 3.5 | | 3.5 | 0 | 0 | — |
| | 1 | 5 | 5 | 5 | 5 | 5 | 1 | 0 | 0 | 0 | 0 | — |
| 318 | 4 | 5 | 5 | 5 | 5 | 5 | 4.5 | 2.5 | 4.5 | 2 | 1 | 1.5 |
| | 1 | 5 | 5 | 5 | 5 | 5 | 0 | 0 | 1.5 | 0 | 0.5 | 0.5 |
| 319 | 4 | 5 | 5 | 5 | 5 | 5 | 0 | 0.5 | 3.5 | 0 | 0 | 0 |
| | 1 | 5 | 5 | 5 | 5 | 5 | 0 | 0 | 4 | 0 | 0 | 0 |
| 320 | 4 | 5 | 5 | 5 | 5 | 5 | 3.5 | 2.5 | 4 | 0 | 0 | 0.5 |
| | 1 | 5 | 5 | 5 | 5 | 5 | 0.5 | 0 | 3.5 | 0 | 0 | 0 |
| 321 | 4 | 5 | 5 | 5 | 5 | 5 | 3 | 1.5 | 4 | 0 | 0 | 0 |
| | 1 | 5 | 5 | 5 | 5 | 5 | 1 | 0 | 3 | 0 | 0 | 0 |
| 325 | 4 | 5 | 5 | 5 | 5 | 5 | 0 | 1.5 | 3 | 0 | 0 | 0 |
| | 1 | 5 | 5 | 5 | 1 | 5 | 0 | 0.5 | 0.5 | 0 | 0 | 0 |
| 326 | 4 | 5 | 5 | 5 | 4 | 5 | 3 | 3 | 4 | 0 | 0 | 0 |
| | 1 | 5 | 5 | 5 | 4 | 5 | 3 | 3 | 4 | 0 | 0 | 0 |
| 327 | 4 | 5 | 5 | 5 | 5 | 5 | 1.5 | 1.5 | 4 | 0 | 0 | 0 |
| | 1 | 5 | 5 | 5 | 4.5 | 5 | 0.5 | 1 | 3 | 0 | 0 | 0 |
| 335 | 4 | 5 | 5 | 5 | 5 | 5 | 2 | 2 | 2.5 | 0 | 0 | 0.5 |
| | 1 | 5 | 4.5 | 5 | 4 | 5 | 0 | 1 | 0 | 0 | 0 | 0 |
| 339 | 4 | 5 | 5 | 4.5 | 5 | 5 | 0 | 1 | 1 | 0 | 0 | 0.5 |
| | 1 | 5 | 5 | 5 | 5 | 5 | 0 | 0 | 0 | 0 | 0 | 0 |
| 340 | 4 | 5 | 5 | 5 | 5 | 5 | 0.5 | 0 | 3.5 | 0 | 0 | 0 |
| | 1 | 5 | 4 | 5 | 4 | 4 | 0 | 0 | 0 | 0 | 0 | 0 |
| 345 | 4 | 5 | 5 | 5 | 5 | 5 | 0 | 0.5 | 3.5 | 0 | 0 | 1 |
| | 1 | 5 | 5 | 5 | 5 | 5 | 0 | 0.5 | 2.5 | 0 | 0 | 0.5 |
| 350 | 4 | 5 | 4 | 5 | 4 | 5 | 0 | 0.5 | 0 | 0 | 0 | 0.5 |
| | 1 | 5 | 3 | 4.5 | 4 | 5 | 0 | 0 | 0 | 0 | 0 | 0 |
| 359 | 4 | 5 | 5 | 5 | 5 | 5 | 0.5 | 0 | 3.5 | 0 | 0 | 1 |
| | 1 | 5 | 4.5 | 5 | 4.5 | 5 | 0 | 0 | 1.5 | 0 | 0 | 0 |
| 361 | 4 | 5 | 5 | 5 | 5 | 5 | 0 | 0.5 | 1.5 | 0 | 0 | 0 |
| | 1 | 5 | 5 | 5 | 5 | 5 | 0 | 0.5 | 1.5 | 0 | 0 | 0 |
| 363 | 4 | 5 | 5 | 5 | 0 | 5 | 0 | 0.5 | 0.5 | 0.5 | 0 | 0.5 |
| | 1 | 5 | 5 | 5 | 0 | 5 | 0 | 0.5 | 5 | 0 | 0 | 0 |
| 387 | 4 | 5 | 5 | 5 | 5 | 5 | 5 | 4.5 | 5 | 0.5 | 0 | 1.5 |
| | 1 | 5 | 5 | 5 | 4 | 5 | 1 | 1.5 | 3.5 | 0 | 0 | 0.5 |
| 405 | 4 | 5 | 5 | 5 | 5 | 5 | 1 | 1.5 | 4.5 | 1.5 | 1 | 1.5 |
| | 1 | 5 | 5 | 5 | 5 | 5 | 0 | 0.5 | 1 | 0 | 0 | 0.5 |
| 430 | 4 | 5 | 5 | 5 | 5 | 5 | 5 | 5 | 5 | 2.5 | 0.5 | 3.5 |
| | 1 | 5 | 5 | 5 | 5 | 5 | 1.5 | 2.5 | 5 | 0.5 | 0 | 2 |
| 431 | 4 | 5 | 5 | 5 | 5 | 5 | 2 | 3.5 | 4 | 0.5 | 0 | 2 |
| | 1 | 5 | 5 | 5 | 5 | 5 | 0 | 1 | 2.5 | 0 | 0 | 1 |
| 438 | 4 | 5 | 5 | 5 | 5 | 5 | 5 | 5 | 5 | 3 | 1 | 2 |
| | 1 | 5 | 5 | 5 | 5 | 5 | 5 | 4 | 5 | 0.5 | 0 | 1.5 |
| 441 | 4 | 5 | 5 | 5 | 5 | 5 | | | | | | |
| | 1 | 5 | 5 | 5 | 3 | 5 | | | | | | |
| 445 | 4 | 5 | 5 | | 5 | 5 | | | | | | |
| | 1 | 5 | 5 | | 5 | 5 | | | | | | |
| 446 | 4 | 5 | 5 | | 5 | 5 | | | | | | |
| | 1 | 5 | 4 | | 5 | 4 | | | | | | |
| 447 | 4 | 5 | 5 | 5 | 5 | 5 | | | | 0 | 0 | 0.5 |
| | 1 | 5 | 5 | 5 | 2 | 5 | | | | 0 | 0 | 0 |
| 448 | 4 | 5 | 5 | 5 | 3 | 5 | | | | 0 | 0 | 0 |
| | 1 | 5 | 5 | 5 | 2 | 5 | | | | 0 | 0 | 0 |
| 449 | 4 | 5 | 5 | 5 | 5 | 5 | | | | 0 | 0 | |
| | 1 | 5 | 5 | 5 | 5 | 5 | | | | 0 | 0 | |
| 450 | 4 | 5 | 5 | 5 | 5 | 5 | | | | 0 | 0 | |
| | 1 | 5 | 5 | 5 | 5 | 5 | | | | 0 | 0 | |
| 452 | 4 | 5 | 5 | 5 | 5 | 5 | | | | 1 | 1 | 1.5 |
| | 1 | 5 | 5 | 5 | 5 | 5 | | | | 0 | 0 | 0.5 |
| 453 | 4 | 5 | 5 | 5 | 3 | 5 | | | | 0 | 0 | 0.5 |
| | 1 | 5 | 5 | 5 | 1 | 5 | | | | 0 | 0 | 0.5 |
| 454 | 5 | 5 | 5 | 5 | 4 | 5 | | | | 0 | 0 | 1 |
| | 1 | 5 | 5 | 5 | 3 | 5 | | | | 0 | 0 | 0 |
| 455 | 4 | 5 | 5 | | 2 | 5 | | | | | | |
| | 1 | 4 | 4 | | 0 | 5 | | | | | | |
| 456 | 4 | 5 | 5 | 5 | 2 | 5 | | | | 0 | 0 | 0 |
| | 1 | 5 | 5 | 5 | 2 | 5 | | | | 0 | 0 | 0 |
| 457 | 4 | 5 | 5 | 5 | 5 | 5 | | | | 0 | 1 | 2.5 |

TABLE 14-continued

| Test Compound | Dose kg/Ha | Herbicidal effects Barnyard-grass | Crab-grass | Green foxtail | Redroot pigweed | Rice flatsedge | Phytotoxicity Rice | Wheat | Maize | Soy-bean | Cotton | Sugar beet |
|---|---|---|---|---|---|---|---|---|---|---|---|---|
| | 1 | 5 | 5 | 5 | 5 | 5 | | | | 0 | 0 | 2 |
| 458 | 4 | 5 | 5 | | 3 | 5 | | | | | | |
| | 1 | 5 | 4 | | 3 | 2 | | | | | | |
| 459 | 4 | 5 | 5 | 5 | 3 | 5 | | | | 0 | 0 | 1 |
| | 1 | 5 | 5 | 5 | 1 | 5 | | | | 0 | 0 | 0.5 |
| 460 | 4 | 5 | 5 | | 5 | 5 | | | | | | |
| | 1 | 5 | 5 | | 3 | 5 | | | | | | |
| 461 | 4 | 5 | 5 | 5 | 5 | 5 | | | | 0 | 0 | 1 |
| | 1 | 5 | 5 | 5 | 2 | 5 | | | | 0 | 0 | 0.5 |
| 462 | 4 | 5 | 5 | 5 | 5 | 5 | | | | 0 | 0.5 | 0.5 |
| | 1 | 5 | 5 | 5 | 3 | 5 | | | | 0 | 0 | 0 |
| 463 | 4 | 5 | 5 | | 3 | 5 | | | | | | |
| | 1 | 2 | 4 | | 0 | 5 | | | | | | |
| 464 | 4 | 5 | 5 | | 2 | 5 | | | | | | |
| | 1 | 2 | 4 | | 2 | 5 | | | | | | |
| 465 | 4 | 5 | 5 | 5 | 5 | 5 | | | | 2.5 | 0.5 | 3 |
| | 1 | 5 | 5 | 5 | 1 | 5 | | | | 0.5 | 0 | |
| 466 | 4 | 5 | 5 | 5 | 4 | 5 | | | | 0 | 0 | 1 |
| | 1 | 5 | 5 | 5 | 3 | 5 | | | | 0 | 0 | 1 |
| 467 | 4 | 5 | 5 | 5 | 4 | 5 | | | | 0 | 0 | 1 |
| | 1 | 5 | 5 | 5 | 1 | 5 | | | | 0 | 0 | 0.5 |
| 468 | 4 | 5 | 5 | | 3 | 5 | | | | | | |
| | 1 | 5 | 5 | | 0 | 5 | | | | | | |
| 469 | 4 | 5 | 5 | | 4 | 5 | | | | | | |
| | 1 | 5 | 5 | | 2 | 5 | | | | | | |
| 471 | 4 | 5 | 5 | 5 | 5 | 5 | | | | 0 | 1.5 | 1.5 |
| | 1 | 5 | 5 | 5 | 5 | | | | 0 | 0 | 0 | |
| 473 | 4 | 5 | 4 | | 2 | 5 | | | | | | |
| | 1 | 3 | 3 | | 0 | 5 | | | | | | |
| 476 | 4 | 5 | 5 | | 5 | 5 | | | | | | |
| | 1 | 4 | 5 | | 1 | 5 | | | | | | |
| 477 | 4 | 5 | 5 | | 1 | 5 | | | | | | |
| | 1 | 5 | 5 | | 0 | 5 | | | | | | |
| 478 | 4 | 5 | 5 | 5 | 5 | 5 | | | | 0.5 | 1 | 3.5 |
| | 1 | 5 | 5 | 5 | 5 | 5 | | | | 0 | 0 | 2 |
| 479 | 4 | 5 | 5 | | 5 | 5 | | | | | | |
| | 1 | 5 | 5 | | 3 | 5 | | | | | | |
| 481 | 4 | 5 | 5 | | 3 | 5 | | | | | | |
| | 1 | 5 | 5 | | 3 | 5 | | | | | | |
| 482 | 4 | 5 | 5 | 5 | 5 | 5 | | | | 0.5 | 0 | 1.5 |
| | 1 | 5 | 5 | 5 | 4 | 5 | | | | 0 | 0 | 0.5 |
| 484 | 4 | 5 | 5 | | 3 | 5 | | | | | | |
| | 1 | 5 | 4 | | 0 | 2 | | | | | | |
| 485 | 4 | 5 | 5 | | 3 | 5 | | | | | | |
| | 1 | 4 | 4 | | 1 | 5 | | | | | | |
| 486 | 4 | 5 | 5 | | 3 | 5 | | | | | | |
| | 1 | 5 | 5 | | 2 | 5 | | | | | | |
| 487 | 4 | 5 | 5 | | 5 | 5 | | | | | | |
| | 1 | 4 | 4 | | 0 | 5 | | | | | | |
| 488 | 4 | 5 | 5 | | 4 | 5 | | | | | | |
| | 1 | 3 | 4 | | 0 | 5 | | | | | | |
| 489 | 4 | 5 | 5 | 5 | 5 | 5 | | | | 2 | 1 | 3.5 |
| | 1 | 5 | 5 | 5 | 3 | 5 | | | | 1 | 0 | 2 |
| 490 | 4 | 5 | 5 | | 4 | 5 | | | | | | |
| | 1 | 3 | 5 | | 1 | 5 | | | | | | |
| 491 | 4 | 5 | 5 | | 3 | 5 | | | | | | |
| | 1 | 4 | 5 | | 0 | 5 | | | | | | |
| 492 | 4 | 5 | 5 | | 2 | 5 | | | | | | |
| | 1 | 4 | 4 | | 2 | 5 | | | | | | |
| 493 | 4 | 5 | 5 | | 4 | 5 | | | | | | |
| | 1 | 5 | 5 | | 3 | 5 | | | | | | |
| 494 | 4 | 5 | 5 | 5 | 5 | 5 | | | | 2 | 1 | 1.5 |
| | 1 | 5 | 5 | 5 | 2 | 5 | | | | 0 | 0 | 0.5 |
| 495 | 4 | 5 | 5 | | 0 | 5 | | | | | | |
| | 1 | 5 | 4 | | 0 | 5 | | | | | | |
| 496 | 4 | 5 | 5 | 5 | 5 | 5 | | | | 3.5 | 1.5 | 4 |
| | 1 | 5 | 5 | 5 | 5 | 5 | | | | 1 | 0 | 2 |
| 497 | 4 | 5 | 5 | | 4 | 5 | | | | | | |
| | 1 | 3 | 5 | | 0 | 5 | | | | | | |
| 498 | 4 | 5 | 5 | | 3 | 5 | | | | | | |
| | 1 | 5 | 5 | | 2 | 5 | | | | | | |
| 599 | 4 | 5 | 5 | | 5 | 5 | | | | | | |
| | 1 | 5 | 5 | | 1 | 5 | | | | | | |
| 501 | 4 | 5 | 5 | | 5 | 5 | | | | | | |
| | 1 | 5 | 5 | | 5 | 5 | | | | | | |
| 502 | 4 | 5 | 5 | | 5 | 5 | | | | | | |
| | 1 | 5 | 5 | | 5 | 5 | | | | | | |
| 503 | 4 | 5 | 5 | | 0 | 5 | | | | | | |
| | 1 | 3 | 2 | | 0 | 5 | | | | | | |

TABLE 14-continued

| Test Compound | Dose kg/Ha | Herbicidal effects: Barnyard-grass | Crab-grass | Green foxtail | Redroot pigweed | Rice flatsedge | Phytotoxicity: Rice | Wheat | Maize | Soy-bean | Cotton | Sugar beet |
|---|---|---|---|---|---|---|---|---|---|---|---|---|
| 504 | 4 | 5 | 5 | | 5 | 5 | | | | | | |
| | 1 | 4 | 4 | | 2 | 5 | | | | | | |
| 505 | 4 | 5 | 5 | | 4 | 5 | | | | | | |
| | 1 | 5 | 5 | | 4 | 5 | | | | | | |
| 506 | 4 | 5 | 5 | 5 | 2 | 5 | | | | 0 | 0 | 2 |
| | 1 | 5 | 5 | 5 | 2 | 5 | | | | 0 | 0 | 0.5 |
| 507 | 4 | 5 | 5 | | 5 | 5 | | | | | | |
| | 1 | 5 | 5 | | 3 | 5 | | | | | | |
| 508 | 4 | 5 | 5 | | 5 | 5 | | | | | | |
| | 1 | 5 | 5 | | 5 | 5 | | | | | | |
| 509 | 4 | 5 | 5 | | 0 | 5 | | | | | | |
| | 1 | 1 | 2 | | 0 | 4 | | | | | | |
| 510 | 4 | 5 | 5 | | 5 | 5 | | | | | | |
| | 1 | 5 | 5 | | 5 | 5 | | | | | | |

Test Example 14 (herbicidal test by upland foliage treatment)

Into each plastic port of 120 $cm^2$, upland soil was filled, then seeds of barnyardgrass, crabgrass, redroot pigweed and rice flatsedge were sown, and they were grown in a greenhouse until barnyardgrass reached three-leaf stage. Each wettable powder prepared from the test compound in accordance with Formulation Example 3 was diluted with water to give the amount of the active ingredient corresponding to 4 kg/hectare, and the diluted solution was uniformly sprayed at an application rate of 1000 liter/hectare from the top of plants by means of a small-size sprayer, when barnyardgrass was in the three-leaf stage. They were grown in a greenhouse, and twenty days after the application, the herbicidal effects were evaluated in accordance with the standards as identified in Table 1C. The results thereby obtained are shown in Table 15.

TABLE 15

| Test Compound | Herbicidal effects: Barnyard-grass | Crab-grass | Redroot pigweed | Rice flatsedge |
|---|---|---|---|---|
| 260 | 4 | 4 | 4 | 5 |
| 264 | 4 | 5 | 4 | 4 |
| 265 | 4 | 5 | 4 | 4 |
| 275 | 5 | 5 | 1 | 5 |
| 282 | 5 | 4 | 4 | 5 |
| 287 | 5 | 4 | 3 | 5 |
| 289 | 5 | 5 | 4 | 5 |
| 292 | 5 | 5 | 5 | 5 |
| 293 | 5 | 5 | 5 | 5 |
| 297 | 5 | 5 | 5 | 5 |
| 298 | 5 | 5 | 4 | 5 |
| 299 | 4 | 5 | 4 | 5 |
| 300 | 5 | 5 | 4 | 4 |
| 301 | 5 | 5 | 4 | 5 |
| 305 | 5 | 5 | 4 | 5 |
| 307 | 5 | 5 | 5 | 5 |
| 320 | 5 | 4 | 4 | 5 |
| 327 | 5 | 5 | 3 | 5 |
| 341 | 5 | 5 | 5 | 5 |
| 345 | 5 | 5 | 3 | 4 |
| 372 | 5 | 5 | 4 | 5 |
| 391 | 5 | 5 | 5 | 5 |
| 393 | 5 | 5 | 5 | 5 |
| 397 | 5 | 5 | 5 | 5 |
| 405 | 5 | 5 | 5 | 5 |
| 431 | 5 | 5 | 5 | 5 |
| 438 | 4 | 4 | 4 | 5 |
| 442 | 5 | 5 | 5 | 5 |
| 445 | 5 | 5 | 2 | 4 |
| 446 | 5 | 4 | 3 | 3 |
| 447 | 5 | 4 | 2 | 3 |

TABLE 15-continued

| Test Compound | Herbicidal effects: Barnyard-grass | Crab-grass | Redroot pigweed | Rice flatsedge |
|---|---|---|---|---|
| 448 | 4 | 5 | 2 | 3 |
| 449 | 5 | 5 | 4 | 2 |
| 450 | 5 | 4 | 2 | 4 |
| 452 | 5 | 5 | 2 | 3 |
| 453 | 4 | 3 | 2 | 3 |
| 454 | 5 | 5 | 2 | 3 |
| 455 | 3 | 2 | 3 | 4 |
| 456 | 4 | 4 | 5 | 3 |
| 457 | 5 | 5 | 1 | 3 |
| 458 | 5 | 5 | 5 | 3 |
| 459 | 5 | 4 | 4 | 3 |
| 460 | 5 | 5 | 3 | 5 |
| 461 | 4 | 4 | 3 | 2 |
| 462 | 3 | 4 | 2 | 2 |
| 463 | 3 | 3 | 3 | 1 |
| 464 | 2 | 1 | 4 | 2 |
| 465 | 5 | 5 | 3 | 3 |
| 466 | 5 | 5 | | 2 |
| 467 | 3 | 2 | 2 | 2 |
| 468 | 3 | 2 | 3 | 3 |
| 469 | 4 | 2 | 3 | 2 |
| 472 | 4 | 4 | 5 | 3 |
| 473 | 0 | 3 | 2 | 5 |
| 476 | 5 | 4 | 1 | 3 |
| 477 | 2 | 3 | 2 | 3 |
| 478 | 5 | 5 | 2 | 2 |
| 479 | 4 | 4 | 3 | 3 |
| 481 | 5 | 4 | 3 | 5 |
| 482 | 4 | 4 | 3 | 4 |
| 484 | 5 | 5 | 3 | 3 |
| 485 | 3 | 4 | 1 | 2 |
| 486 | 2 | 3 | 0 | 3 |
| 487 | 5 | 5 | | 4 |
| 488 | 5 | 5 | 2 | 3 |
| 490 | 5 | 5 | 4 | 4 |
| 491 | 5 | 5 | 4 | 4 |
| 492 | 5 | 5 | 2 | 3 |
| 493 | 3 | 5 | 2 | 3 |
| 494 | 5 | 5 | 5 | 4 |
| 496 | 4 | 4 | 0 | 2 |
| 497 | 4 | 4 | 2 | 4 |
| 498 | 4 | 4 | 2 | 4 |
| 499 | 4 | 4 | 2 | 4 |
| 501 | 4 | 5 | 3 | 5 |
| 502 | 5 | 4 | 4 | 5 |
| 503 | 5 | 5 | 1 | 5 |
| 504 | 4 | 3 | 2 | 5 |
| 505 | 5 | 4 | 3 | 4 |
| 506 | 4 | 5 | 2 | 5 |
| 507 | 5 | 4 | 1 | 4 |
| 508 | 5 | 5 | 2 | 3 |
| 510 | 4 | 5 | 2 | 3 |

What is claimed and desired to be secured by Letters Patent in the United States is:

1. A substituted phenoxy urea having the formula:

Embodiment C:

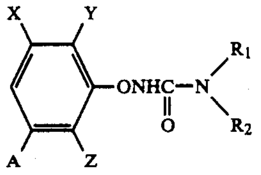

(XX)

wherein A is a halogen atom or a trifluoromethyl group, each of X, Y and Z is a hydrogen atom, a halogen atom or a trifluoromethyl group $R_1$ and $R_2$ form, together with carbon and the nitrogen atom to which they are bonded, a 3-8 membered monocyclic ring which may have a double bond within said ring and may have one or more lower alkyl branches.

2. The urea according to claim 1, wherein A is a chlorine atom, and each of X, Y and Z is a hydrogen atom or a chlorine atom.

3. The urea and the 3-8 membered ring formed by $R_1$ and $R_2$ together with the nitrogen atom to which they are bonded, is

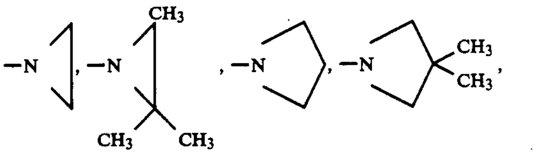

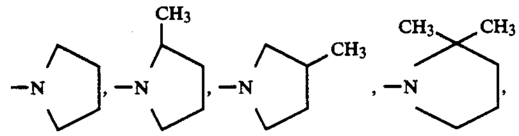

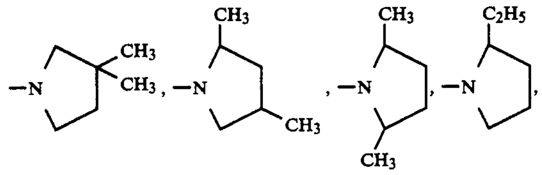

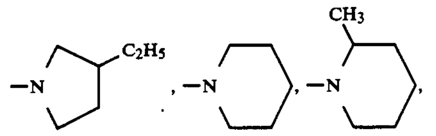

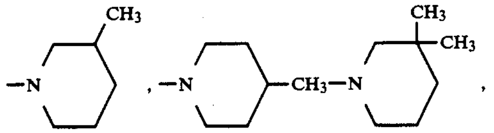

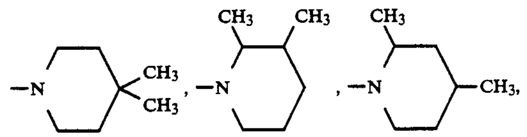

-continued

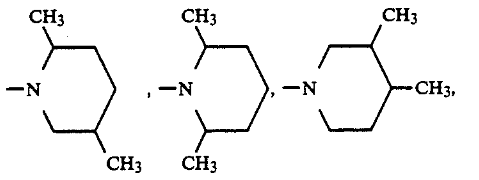

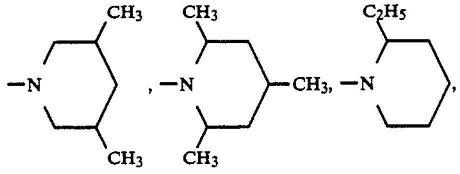

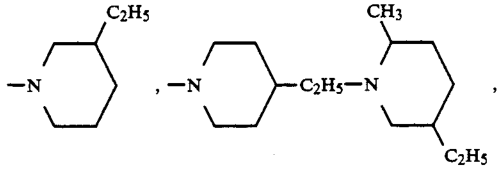

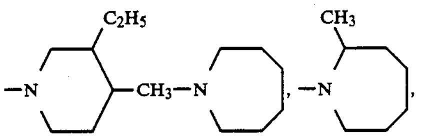

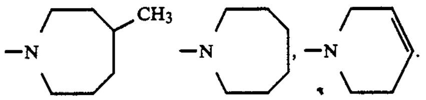

4. The urea according to claim 1, wherein the aryl moiety of the formula:

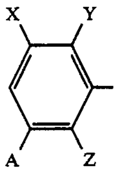

in the formula I, is 3-chlorophenyl, 2,3-dichlorophenyl, 3,5-dichlorophenyl, 2,5-dichlorophenyl, 2,5-difluorophenyl, 2,3,5-trichlorophenyl, 2,3,6-trichlorophenyl, 2,3,5,6-tetrachlorophenyl, 3-trifluoromethylphenyl, 3,5-di(trifluoromethyl)phenyl, 2,3-di(trifluoromethyl)phenyl, 2,5-di(trifluoromethyl)phenyl, 2-chloro-3-trifluoromethylphenyl, 3-chloro-2-trifluoromethylphenyl, (5-chloro-2-trifluoromethylphenyl) 2-chloro-5-trifluoromethylphenyl, 5-chloro-2-trifluoromethylphenyl or 3-chloro-5-trifluoromethylphenyl.

5. The urea according to claim 1, which has the formula:

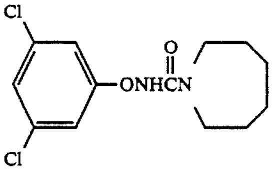
6. A herbicide comprising a herbicidally effective amount of a substituted phenoxy urea having the formula (XX) according to claim 1, and a carrier.
7. The urea according to claim 1, which has the formula:
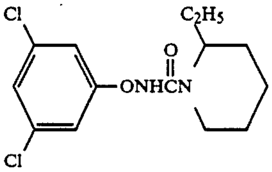
* * * * *